(12) United States Patent
Yaniv et al.

(10) Patent No.: US 10,912,663 B2
(45) Date of Patent: Feb. 9, 2021

(54) SHAPE CHANGE STRUCTURE FOR TREATMENT OF NASAL CONDITIONS INCLUDING SINUSITIS

(71) Applicant: S.T.S. Medical Ltd., Misgav Business Park (IL)

(72) Inventors: Eitan Yaniv, Hod-HaSharon (IL); Gady Har-El, Hollis, NY (US); Gregory Frenklach, Modiln (IL); Joseph Flomenblit, Petach-Tikva (IL); Lena Shlossberg, Petach-Tikva (IL)

(73) Assignee: S.T.S. Medical Ltd., Doar-Na Misgav (IL)

( * ) Notice: Subject to any disclaimer, the term of this patent is extended or adjusted under 35 U.S.C. 154(b) by 320 days.

(21) Appl. No.: 15/529,551

(22) PCT Filed: Nov. 26, 2015

(86) PCT No.: PCT/IL2015/051153
§ 371 (c)(1),
(2) Date: May 25, 2017

(87) PCT Pub. No.: WO2016/084087
PCT Pub. Date: Jun. 2, 2016

(65) Prior Publication Data
US 2018/0360626 A1    Dec. 20, 2018

Related U.S. Application Data

(60) Provisional application No. 62/084,831, filed on Nov. 26, 2014.

(51) Int. Cl.
*A61F 2/86* (2013.01)
*A61L 31/16* (2006.01)
(Continued)

(52) U.S. Cl.
CPC .......... *A61F 2/86* (2013.01); *A61F 2/186* (2013.01); *A61F 2/958* (2013.01); *A61L 31/14* (2013.01);
(Continued)

(58) Field of Classification Search
CPC .......... A61F 2/18–186; A61F 2/82–45; A61F 2/02–07; A61F 2/95–97;
(Continued)

(56) References Cited

U.S. PATENT DOCUMENTS 5,197,978 A * 3/1993 Hess ................. A61F 2/82
606/194
5,336,163 A   8/1994 DeMane et al.
(Continued)

FOREIGN PATENT DOCUMENTS

CN   1210021   3/1999
CN   1252258   5/2000
(Continued)

OTHER PUBLICATIONS

Communication Pursuant to Article 94(3) EPC dated Mar. 22, 2018 From the European Patent Office Re. Application No. 14738907.6. (7 Pages).
(Continued)

*Primary Examiner* — Sarah A Simpson

(57) ABSTRACT

A method of treatment of nasal conditions comprising: delivering an expandable structure in a crimped configuration to a nasal lumen; expanding the expandable structure within the nasal lumen to a stable expanded configuration; removing the structure from the nasal lumen, after a time period, where removing comprises causing the structure to self-crimp. The expandable structure optionally comprises: a first shape memory (SM) portion which is in a strain-induced state; and a second portion which resists expansion
(Continued)

of said structure due to said first portion, over a plurality of different expansion states of said first portion. Optionally, the properties of the second portion vary over its cross section. For example an outer surface and/or peripheral layer may have desirable environmental resistance properties and/or a frame may have desirable mechanical properties, for example a high creep resistance.

37 Claims, 46 Drawing Sheets

(51) Int. Cl.
  *A61F 2/18*     (2006.01)
  *A61F 2/958*    (2013.01)
  *A61L 31/14*    (2006.01)

(52) U.S. Cl.
  CPC ....... *A61L 31/16* (2013.01); *A61F 2250/0059* (2013.01)

(58) Field of Classification Search
  CPC .................. A61F 2002/821–91591; A61F 2002/041–077; A61F 2002/9505–9586; A61F 5/08; A61F 5/56
  See application file for complete search history.

(56) References Cited

U.S. PATENT DOCUMENTS

| | | | |
|---|---|---|---|
| 5,441,515 A | 8/1995 | Khosravi et al. | |
| 5,637,113 A | 6/1997 | Tartaglia et al. | |
| 5,693,065 A | 12/1997 | Rains, III | |
| 5,876,434 A | 3/1999 | Flomenblit et al. | |
| 5,882,444 A | 3/1999 | Flomenblit et al. | |
| 5,899,935 A | 5/1999 | Ding | |
| 5,964,770 A * | 10/1999 | Flomenblit | C22F 1/006 606/78 |
| 6,083,259 A | 7/2000 | Frantzen | |
| 6,086,610 A | 7/2000 | Duerig et al. | |
| 7,361,168 B2 | 4/2008 | Makower et al. | |
| 7,410,480 B2 | 8/2008 | Muni et al. | |
| 7,645,272 B2 | 1/2010 | Chang et al. | |
| 7,654,997 B2 | 2/2010 | Makower et al. | |
| 7,771,409 B2 | 8/2010 | Chang et al. | |
| 7,803,150 B2 | 9/2010 | Chang et al. | |
| 8,025,635 B2 | 9/2011 | Eaton et al. | |
| 8,585,731 B2 | 11/2013 | Abbate et al. | |
| 2001/0056296 A1 | 12/2001 | Sugita et al. | |
| 2002/0002400 A1 | 1/2002 | Drasler et al. | |
| 2003/0004563 A1 | 1/2003 | Jackson et al. | |
| 2003/0036792 A1* | 2/2003 | Richter | A61F 2/91 623/1.12 |
| 2003/0149472 A1 | 8/2003 | Pinchuk et al. | |
| 2005/0004647 A1 | 1/2005 | Bassoe | |
| 2005/0251193 A1 | 11/2005 | Lary | |
| 2006/0020324 A1 | 1/2006 | Schmid et al. | |
| 2006/0106361 A1 | 5/2006 | Muni et al. | |
| 2006/0184231 A1 | 8/2006 | Rucker | |
| 2008/0009936 A1 | 1/2008 | Kim et al. | |
| 2008/0077240 A1* | 3/2008 | Saidi | A61F 2/18 623/10 |
| 2008/0147164 A1 | 6/2008 | Gale et al. | |
| 2008/0188924 A1 | 8/2008 | Prabhu | |
| 2008/0200974 A1* | 8/2008 | Trauthen | A61F 2/91 623/1.2 |
| 2008/0300668 A1 | 12/2008 | Bonsignore | |
| 2009/0036968 A1* | 2/2009 | Hepworth | A61F 2/186 623/1.11 |
| 2009/0099639 A1 | 4/2009 | Sabaria | |
| 2009/0266365 A1 | 10/2009 | Oberle | |
| 2010/0010622 A1 | 1/2010 | Lowe et al. | |
| 2011/0112512 A1 | 5/2011 | Muni et al. | |
| 2012/0046756 A1* | 2/2012 | Wang | A61F 2/82 623/23.7 |
| 2013/0053946 A1 | 2/2013 | Stinson | |
| 2013/0096666 A1 | 4/2013 | Bregulla et al. | |
| 2014/0243950 A1 | 8/2014 | Weiner | |
| 2014/0277072 A1 | 9/2014 | Suehara | |
| 2014/0296957 A1 | 10/2014 | Janzten et al. | |
| 2016/0081826 A1* | 3/2016 | Fredrickson | C08L 75/04 623/23.7 |
| 2016/0101221 A1* | 4/2016 | Flomenblit | A61F 2/844 623/1.19 |

FOREIGN PATENT DOCUMENTS

| | | |
|---|---|---|
| CN | 1269845 | 10/2000 |
| CN | 101048526 | 10/2007 |
| CN | 101189016 | 5/2008 |
| CN | 101612074 | 12/2009 |
| CN | 102805676 | 12/2012 |
| CN | 102973340 | 3/2013 |
| DE | 10226734 | 11/2003 |
| EP | 2298317 | 3/2011 |
| EP | 2298318 | 3/2011 |
| EP | 2298319 | 3/2011 |
| EP | 2512578 | 10/2012 |
| GB | 2343119 | 5/2000 |
| JP | 2000-135290 | 5/2000 |
| JP | 2001-510084 | 7/2001 |
| JP | 2001-511666 | 8/2001 |
| JP | 2001-525013 | 12/2001 |
| JP | 2008-850349 | 3/2008 |
| JP | 2008-113958 | 5/2008 |
| JP | 2012-034896 | 2/2012 |
| WO | WO 95/26695 | 10/1995 |
| WO | WO 95/31945 | 11/1995 |
| WO | WO 98/28035 | 7/1998 |
| WO | WO 99/04053 | 1/1999 |
| WO | WO 99/16385 | 4/1999 |
| WO | WO 99/20205 | 4/1999 |
| WO | WO 00/10485 | 3/2000 |
| WO | WO 00/24338 | 5/2000 |
| WO | WO 00/32136 | 6/2000 |
| WO | WO 01/01888 | 1/2001 |
| WO | WO 01/85064 | 11/2001 |
| WO | WO 03/020175 | 3/2003 |
| WO | WO 03/034940 | 5/2003 |
| WO | WO 2005/053576 | 6/2005 |
| WO | WO 2005/096992 | 10/2005 |
| WO | WO 2006/014699 | 2/2006 |
| WO | WO 2006/107957 | 10/2006 |
| WO | WO 2007/054014 | 5/2007 |
| WO | WO 2010/107681 | 9/2010 |
| WO | WO 2010/120532 | 10/2010 |
| WO | WO 2011/127452 | 10/2011 |
| WO | WO 2012/011269 | 1/2012 |
| WO | WO 2012/173995 | 12/2012 |
| WO | WO 2013/032494 | 3/2013 |
| WO | WO 2014/188437 | 11/2014 |
| WO | WO 2016/084087 | 6/2016 |

OTHER PUBLICATIONS

Notification of Office Action dated Aug. 14, 2017 From the State Intellectual Property Office of the People's Republic of China Re. Application No. 201480041307.4 together with Its Summary in English.) (6 Pages).
Official Action dated May 10, 2019 From the US Patent and Trademark Office Re. U.S. Appl. No. 14/893,069. (26 pages).
Notification of Office Action and Search Report dated Feb. 27, 2018 From the State Intellectual Property Office of the People's Republic of China Re. Application No. 201480041307.4 and Its Translation of Office Action Into English. (6 Pages).
Official Action dated Mar. 7, 2018 From the US Patent and Trademark Office Re. U.S. Appl. No. 14/893,069. (38 pages).
Communication Relating to the Results of the Partial International Search dated Oct. 7, 2014 From the International Searching Authority Re. Application No. PCT/IL2014/050466.
Examination Report dated May 2, 2017 From the Australian Government, IP Australia Re. Application No. 2014269936. (3 Pages).

(56) References Cited

OTHER PUBLICATIONS

International Preliminary Report on Patentability dated Dec. 3, 2015 From the International Bureau of WIPO Re. Application No. PCT/IL2014/050466.
International Preliminary Report on Patentability dated Jun. 8, 2017 From the International Bureau of WIPO Re. Application No. PCT/IL2015/051153. (15 Pages).
International Search Report and the Written Opinion dated Feb. 3, 2015 From the International Searching Authority Re. Application No. PCT/IL2014/050466.
International Search Report and the Written Opinion dated Aug. 5, 2016 From the International Searching Authority Re. Application No. PCT/IL2015/051153.
Invitation to Pay Additional Fees dated May 20, 2016 From the International Searching Authority Re. Application No. PCT/IL2015/051153.
Notification of Office Action dated Jan. 20, 2017 From the State Intellectual Property Office of the People's Republic of China Re. Application No. 201480041307.4. (3 Pages).
Translation of Notification of Office Action dated Jan. 20, 2017 From the State Intellectual Property Office of the People's Republic of China Re. Application No. 201480041307.4. (1 Page).
Vermette et al. "Biomedical Degradation of Polyurethanes", Biomedical Applications of Polyurethanes, 6(Chap.5): 97-159, 2001.
Restriction Official Action dated Oct. 17, 2017 From the US Patent and Trademark Office Re. U.S. Appl. No. 14/893,069. (7 pages).
Communication Pursuant to Article 94(3) EPC dated Apr. 16, 2019 From the European Patent Office Re. Application No. 14738907.6. (8 Pages).
Applicant-Initiated Interview Summary dated May 15, 2018 From the US Patent and Trademark Office Re. U.S. Appl. No. 14/893,069. (3 pages).
Notice of Reason for Rejection dated Apr. 3, 2018 From the Japan Patent Office Re. Application No. 2016-514534 and Its Summary in English. (5 Pages).
Translation Dated Apr. 22, 2018 of Notice of Reason for Rejection dated Apr. 3, 2018 From the Japan Patent Office Re. Application No. 2016-514534. (4 Pages).
Notice of Reasons for Rejection dated Aug. 21, 2018 From the Japan Patent Office Re. Application No. 2016-514534. (3 Pages).
Translation of Notification of Office Action dated Aug. 14, 2017 From the State Intellectual Property Office of the People's Republic of China Re. Application No. 201480041307.4. (2 Pages).
Translation Dated Sep. 4, 2018 of Notice of Decision of Refusal dated Aug. 21, 2018 From the Japan Patent Office Re. Application No. 2016-514534. (3 Pages).
Official Action dated Sep. 7, 2018 From the US Patent and Trademark Office Re. U.S. Appl. No. 14/893,069. (23 pages).
Bansiddhi et al. "Shape-Memory NiTi-Nb Foams", Journal of Material Research 24(6):2107-2117, 2009.
Official Action dated Oct. 10, 2019 From the US Patent and Trademark Office Re. U.S. Appl. No. 14/893,069. (26 Pages).
Communication Pursuant to Article 94(3) EPC dated Feb. 21, 2020 From the European Patent Office Re. Application No. 14738907.6. (7 Pages).
Notice of Reason for Rejection dated Nov. 19, 2019 From the Japan Patent Office Re. Application No. 2014-513308 and a Summary in English. (5 Pages).
Translation Dated Dec. 5, 2019 of Notice of Reasons for Refusal dated Nov. 19, 2019 From the Japan Patent Office Re. Application No. 2014-513308. (5 Pages).
Official Action dated Mar. 5, 2020 From the US Patent and Trademark Office Re. U.S. Appl. No. 14/893,069. (20 pages).
Final Official Action dated Jul. 15, 2020 from the US Patent and Trademark Office Re. U.S. Appl. No. 14/893,069. (15 pages).
Notice of Decision of Refusal dated Aug. 4, 2020 From the Japan Patent Office Re. Application No. 2014-513308 and Its Translation Into English. (7 Pages).
Requisition by the Examiner dated Jun. 5, 2020 From the Innovation, Science and Economic Development Canada, Canadian Intellectual Property Office Re. Application No. 2,911,226.

* cited by examiner

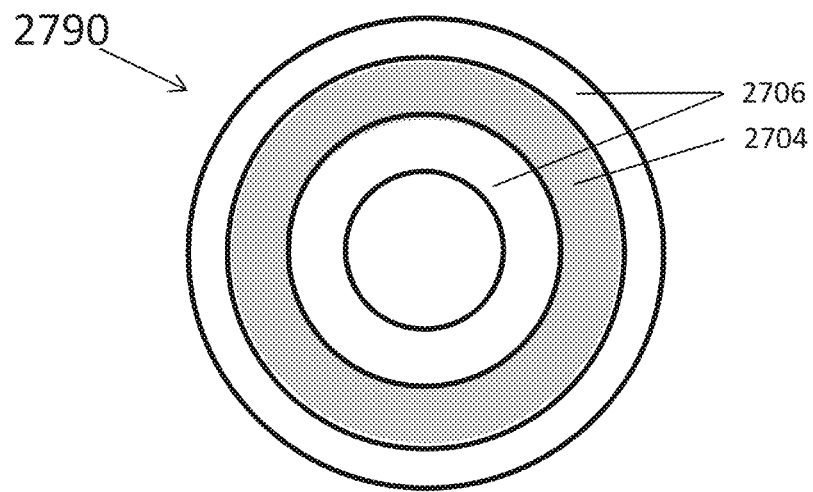
FIG. 27
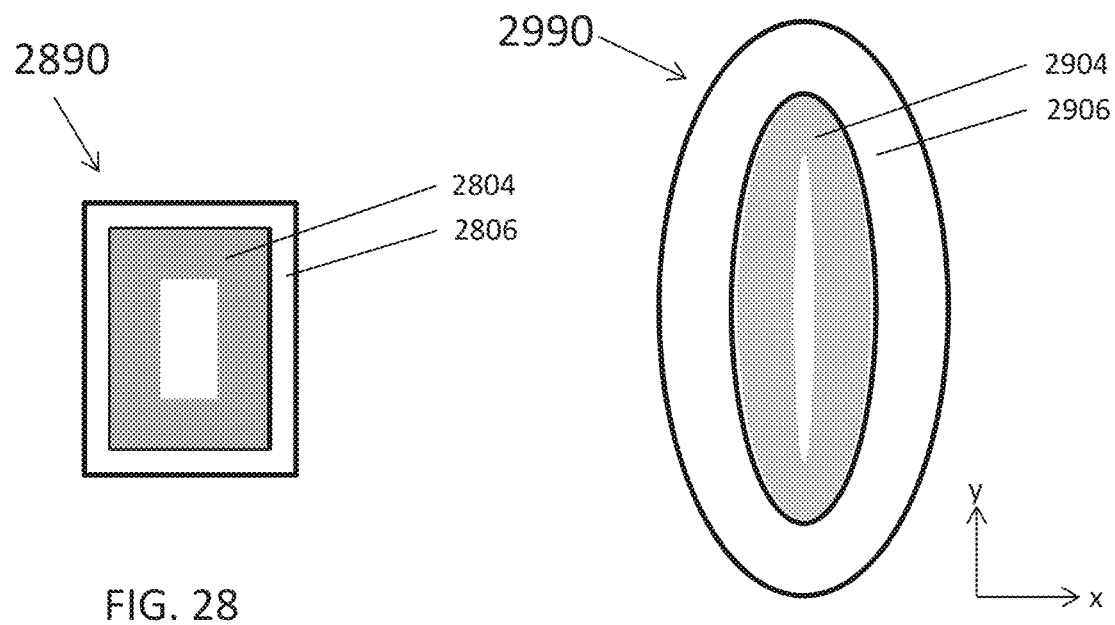
FIG. 28
FIG. 29

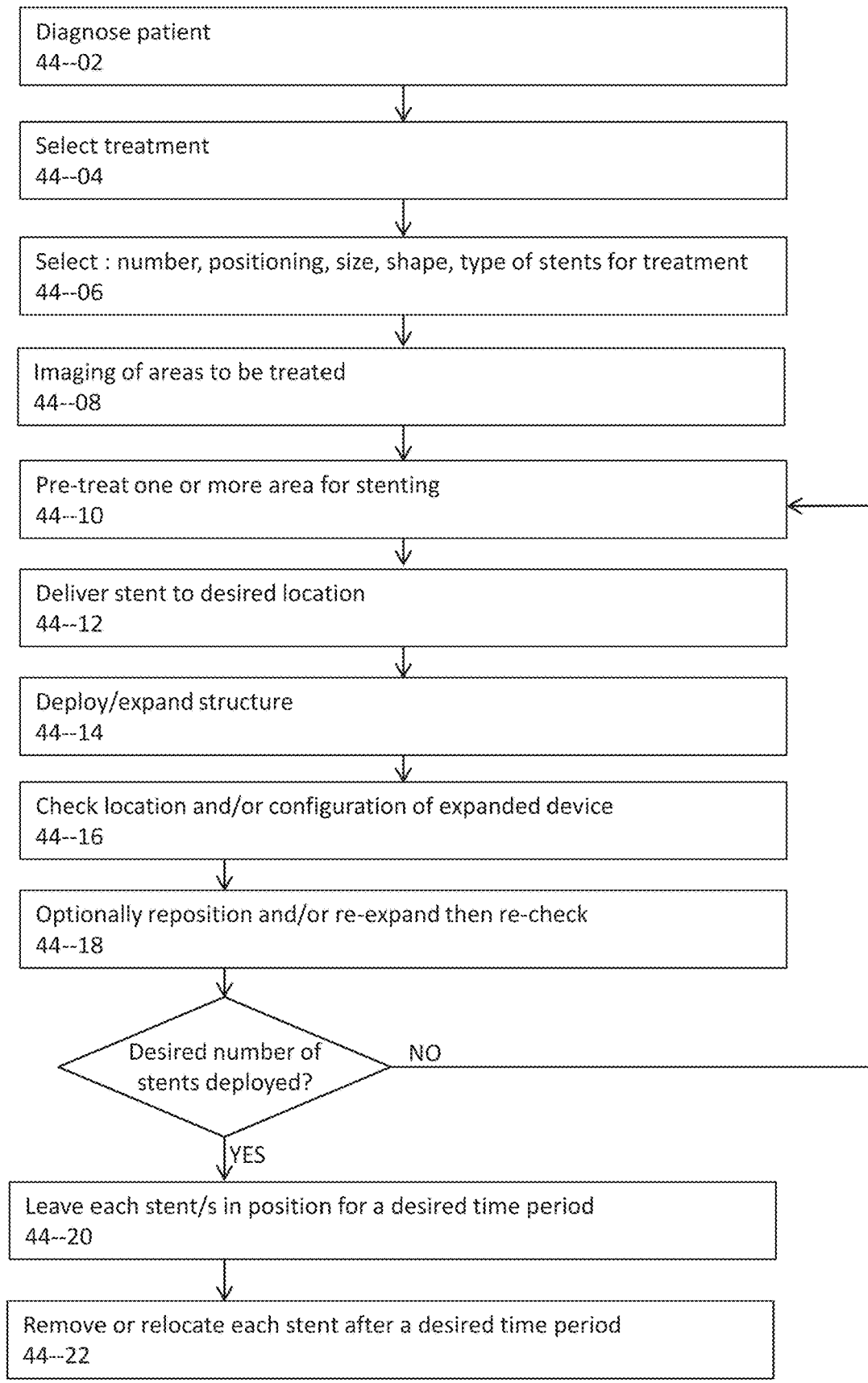
FIG. 44 - method of treatment

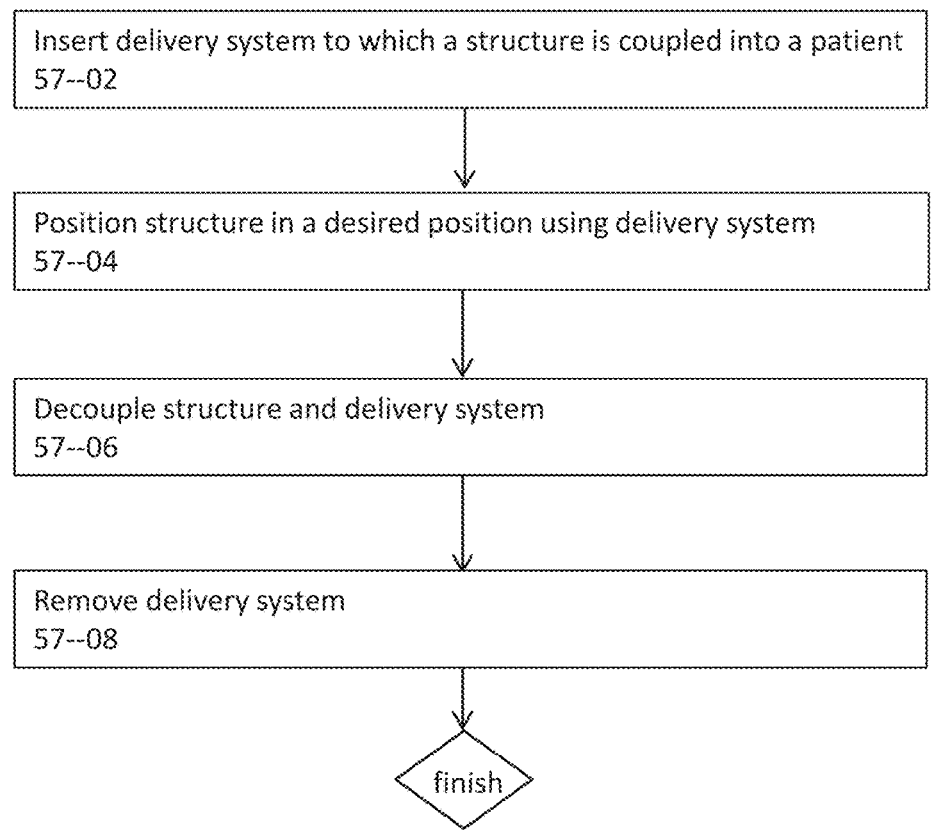
FIG. 57- method of delivery and deployment
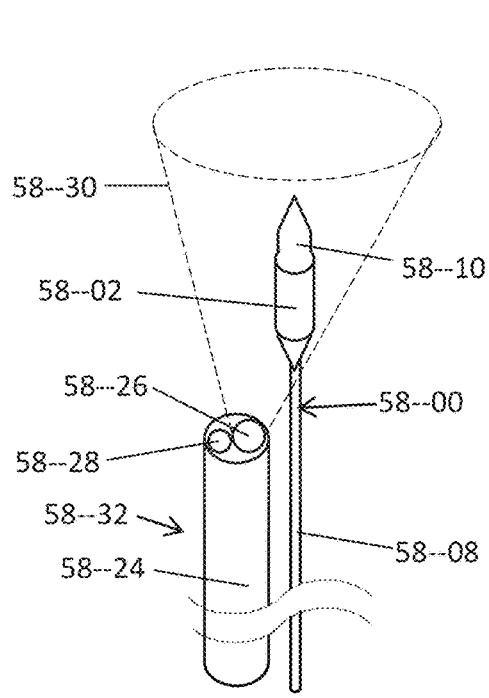
FIG. 58
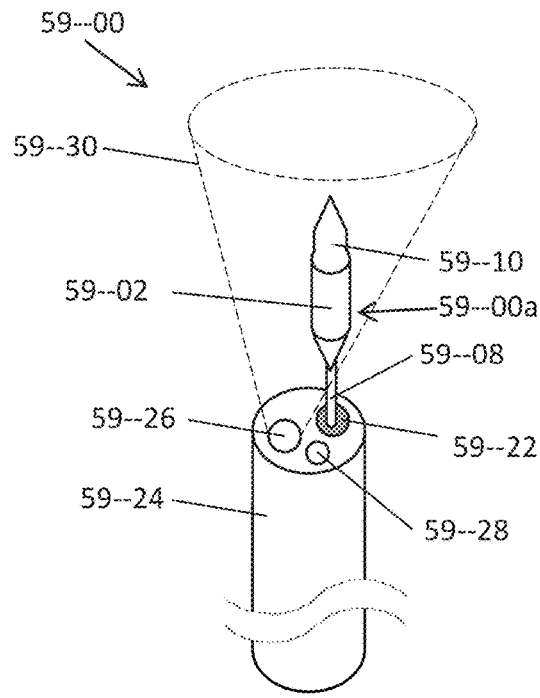
FIG. 59

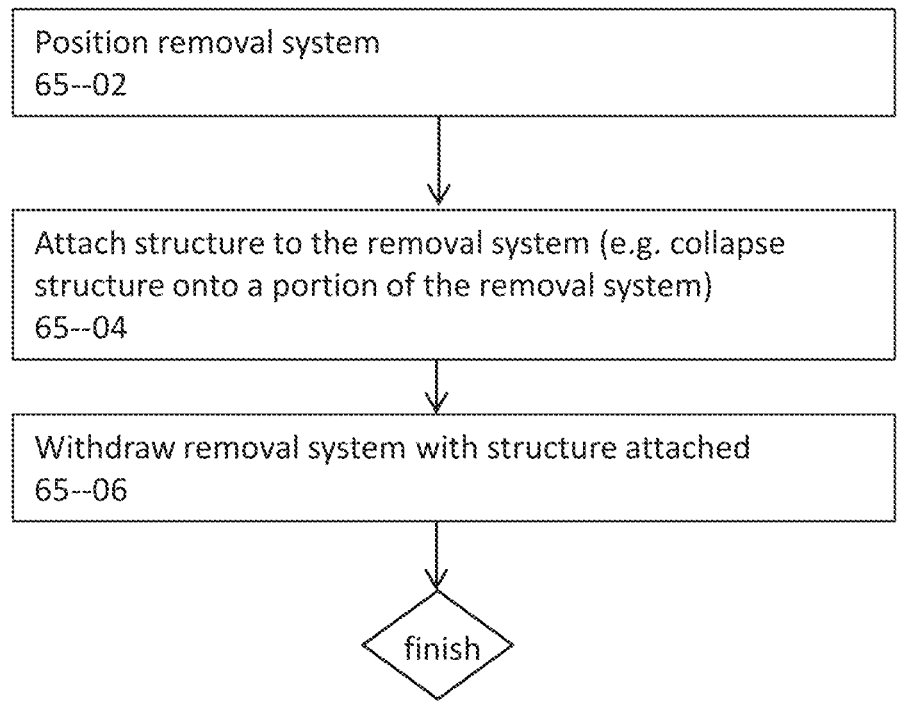
FIG. 65 - method of removal
FIG. 66

SHAPE CHANGE STRUCTURE FOR TREATMENT OF NASAL CONDITIONS INCLUDING SINUSITIS

RELATED APPLICATIONS

This application is a National Phase of PCT Patent Application No. PCT/IL2015/051153 having international filing date of Nov. 26, 2015, which claims the benefit of priority under 35 USC § 119(e) of U.S. Provisional Patent Application No. 62/084,831 filed Nov. 26, 2014. The contents of the above applications are all incorporated by reference as fully set herein in their entirety.

FIELD AND BACKGROUND OF THE INVENTION

The present invention, in some embodiments thereof, relates to structures and methods for treating nasal conditions and, more particularly, but not exclusively, to structures and methods for treating sinusitis.

The human head includes a number of hollow cavities called paranasal sinuses, which connect to the nasal cavity via small openings called "ostia" (singular "ostium"). Generally, the human head includes eight paranasal sinuses (two sets of four on each side), called the frontal, ethmoid, sphenoid and maxillary sinuses. The frontal sinuses are located in the forehead, the maxillary sinuses are in the cheeks, the ethmoid sinuses are under the eyes, and the sphenoid sinuses are further back in the head, near the pituitary gland. Paranasal sinuses are lined with mucous-producing epithelial tissue and have cilia to sweep mucous out of the sinuses and through the ostia into the nasal cavity.

Sinusitis is defined as an inflammation of the paranasal sinuses caused by one or more of infection, allergy, or structural issues such as blockage of the sinus ostia. Symptoms of sinusitis can include nasal congestion, facial discomfort, nasal discharge, headache, and fatigue. The disease is considered chronic when it lasts four months in a year or longer. Sinusitis affects 37 million people each year, making it one of the most common health problems in the U.S.

Typically, initial therapy is drug therapy involving anti-inflammatory agents to reduce inflammation and/or antibiotics to treat infection. A large number of patients, however, do not respond to drug therapy and seek a surgical option. The most common surgical procedure currently performed for chronic sinusitis treatment is Functional Endoscopic Sinus Surgery (FESS) where, for example, drainage pathways from the sinus to nasal cavity are established.

Common suboptimal surgery results include recurrent inflammation and/or polyposis and/or adhesion/synechiae (e.g. middle turbinate lateralization) and/or stenosis of the surgically enlarged ostia.

Controlling for these postoperative issues has been shown to lead to better long-term outcomes of surgery. Devices designed to counteract the tendency for scarring and synechiae formation include stents, packing, sponges, and gels.

U.S. Pat. No. 8,585,731 to Abbate et al. discloses "self-expanding devices and methods of using and making them. The devices may be useful in a variety of locations within the body, for a number of different uses. In some variations, the devices have a first compressed configuration enabling low profile delivery through a delivery device, a second expanded configuration for apposition against tissue, and comprise either a single continuous filament or at least two non-intersecting filaments. In some variations, the device is formed into a shape having a series of peaks and valleys. At least one of the peaks and valleys may have a loop at the end thereof. At least a portion of these devices may be capable of biodegrading over a predetermined period of time, and the devices may be configured for drug delivery. Methods of treating one or more sinus cavities are also described here."

U.S. Patent Application Publication No. US 2011/0112512 to Muni et al. discloses "Devices and methods are described for improving drainage and/or aeration of maxillary sinuses and for treating maxillary sinus disease. Spacer devices are implanted through natural or man-made openings in the maxillary sinus. In some embodiments, the spacer device is loaded with a therapeutic substance which then exits the device over a desired time period to treat maxillary sinus disease."

Other background art includes Patrick Vermette, Stéphane Lévesque, and Hans J. Griesser, Biomedical Degradation of Polyurethanes, Chapter 5 in BIOMEDICAL APPLICATIONS OF POLYURETHANES Tissue Engineering Intelligence Unit, Eurekah.Com, Landes Bioscience, Georgetown Tex. 2001.

SUMMARY OF THE INVENTION

According to an aspect of some embodiments of the present invention there is provided a method of treatment of nasal conditions comprising: delivering an expandable structure in a crimped configuration to a nasal lumen; expanding the expandable structure within the nasal lumen to a stable expanded configuration; removing the structure from the nasal lumen, after a time period, where removing comprises causing the structure to self-crimp.

According to some embodiments of the invention, causing comprises changing a temperature of the structure. According to some embodiments of the invention, expanding comprises expanding the structure to a stable expanded configuration where at least a portion of the structure matches a geometry of the nasal lumen. According to some embodiments of the invention, the structure substantially does not apply outwards pressure to the nasal lumen.

According to some embodiments of the invention, expanding is by inflating a balloon within the expandable structure. According to some embodiments of the invention, expanding is gradual. According to some embodiments of the invention, the method comprises checking one or more of a structure geometry and a structure position within the lumen. According to some embodiments of the invention, expanding comprises expanding the structure in more than one separate expansion.

According to some embodiments of the invention, the method comprises checking one or more of a structure geometry and a structure position within the lumen between the separate expansions.

According to some embodiments of the invention, the method comprises imaging the structure and/or the lumen to assist a user in one or more of the delivering, the expanding and the removing.

According to some embodiments of the invention, the lumen is a sinus ostium. According to some embodiments of the invention, the lumen is a portion of a nasal cavity between a turbinate and a septum. According to some embodiments of the invention, the lumen is a surgically created lumen. According to some embodiments of the invention, the lumen is an ethmoid sinus cavity surgically created during ethmoidectomy.

According to some embodiments of the invention, the method comprises pre-treating the lumen. According to some embodiments of the invention, the pre-treating includes surgical widening of the lumen.

According to some embodiments of the invention, the expanding comprises expanding at least a portion of the structure to a desired configuration which does not match a geometry of the lumen. According to some embodiments of the invention, the expanding comprises expanding the structure to widen at least a portion of the lumen.

According to some embodiments of the invention, the expanding is by application of a force to the expandable structure and the force is at most half of a force required to crush the structure in the expanded configuration.

According to some embodiments of the invention, the removing comprises changing a temperature of the structure which causes the structure to collapse.

According to some embodiments of the invention, the removing is carried out without general anesthetic. According to some embodiments of the invention, the delivering and the expanding are carried out without general anesthetic.

According to some embodiments of the invention, the method comprises repositioning the structure. According to some embodiments of the invention, the repositioning comprises: collapsing at least a portion of the structure to at least a size suitable for moving the structure within the lumen; delivering the structure to a desired position within the nasal lumen; expanding the structure.

According to some embodiments of the invention, the delivering includes inserting the structure through a nostril.

According to some embodiments of the invention, the structure releases medication into the lumen. According to some embodiments of the invention, the structure releases medication into the lumen gradually. According to some embodiments of the invention, the structure releases medication into the lumen over a time period. According to some embodiments of the invention, the medication comprises a steroid. According to some embodiments of the invention, the method comprises applying medication to the structure within the lumen. According to some embodiments of the invention, the applying is periodically after the expanding.

According to an aspect of some embodiments of the present invention there is provided an expandable structure for expansion inside an adult human nasal lumen comprising: a shape memory (SM) portion; and a polymer portion; wherein the structure is stable for a range of diameters and for a range of diameters along a structure length including: a range of crimped diameters suitable for inserting the structure into the nasal lumen; a range of deployed diameters suitable for supporting at least a portion of the nasal lumen.

According to some embodiments of the invention, the polymer portion has a non-uniform cross section including a peripheral layer composed at least 30% of a second polymer, and a frame composed at least 30% of a first polymer; said second polymer having a greater environmental durability than said second polymer and wherein said first polymer has a higher creep resistance than said second polymer.

According to some embodiments of the invention, open spaces within the structure include medication suitable for treating the nasal lumen.

According to some embodiments of the invention, the nasal lumen is a sinus ostium; wherein the crimped range of diameters is 3-5 mm; and wherein the deployed range of diameters is 5-12 mm. According to some embodiments of the invention, the nasal lumen is a nasal cavity; wherein the crimped range of diameters is 4-6 mm; and wherein the deployed range of diameters is 7-14 mm.

According to some embodiments of the invention, the nasal lumen is a nasal cavity; wherein the crimped range of diameters is 3-6 mm; and wherein the deployed range of diameters is 5-14 mm.

According to some embodiments of the invention, the structure in the deployed range of diameters has a resistance to a crimping force acting to radially crimp the structure equal to at least 100% of a force required to expand the structure from the crimped range of diameters to the deployed range of diameters.

According to some embodiments of the invention, the range of diameters along a structure length, corresponds to a structure cross section varying between a smallest expanded state diameter and a largest expanded state diameter which is double or more the smallest expanded state diameter.

According to some embodiments of the invention, the structure is radially elastically deformable, at least for the deployed range of diameters.

According to some embodiments of the invention, for the deployed range of diameters, the structure collapses, upon a temperature change, to a diameter within the crimped range of diameters.

According to an aspect of some embodiments of the present invention there is provided a system for insertion into a nasal cavity through a nostril comprising: a structure comprising a SM material portion and a polymer portion; an elastic element at least a part of which is located within the structure; a balloon, at least a part of which balloon is within the elastic element and within the structure; and an input pipe connected to the balloon wherein the balloon is inflated through the pipe; wherein the elastic element resists expansion of the balloon.

According to some embodiments of the invention, comprising: a second input pipe including an outlet, where fluid exiting the outlet irrigates a region adjacent to the balloon.

According to an aspect of some embodiments of the present invention there is provided an expandable structure for expansion inside an adult human nasal lumen comprising: a shape memory (SM) portion; and a polymer portion where the polymer portion resists expansion of the SM portion; wherein the structure is stable for a range of diameters and for varying diameters along a structure length; wherein open spaces within the structure include medication suitable for treating the nasal lumen.

According to an aspect of some embodiments of the present invention there is provided an expandable structure for expansion inside a body lumen comprising: a polymer portion which is elastic upon expansion of less than a minimum expansion time period; wherein, for an expansion to an expanded state for a time period of more than the minimum expansion time period, the structure remains in the expanded state.

According to some embodiments of the invention, said expanding is for at least a minimum time period. According to some embodiments of the invention, wherein said removing comprises heating said structure at least above body temperature.

According to some embodiments of the invention, the polymer portion has a non-uniform cross section including a peripheral layer composed at least 30% of a second polymer, and a frame composed at least 30% of a first polymer; the second polymer having a greater environmental durability than the second polymer and wherein the first polymer has a higher creep resistance than the second polymer.

According to an aspect of some embodiments of the invention, there is provided a polymer portion of an elastic tube comprising: a wall having a non-uniform cross section including: a peripheral layers of the non-uniform cross section; the peripheral layer composed at least 30% of a second polymer, and a frame of the non-uniform cross section, the frame composed at least 50% a first polymer; the second polymer having a greater environmental resistance than the first polymer and wherein the first polymer has a higher creep resistance than the second polymer.

According to an aspect of some embodiments of the invention, there is provided an expandable structure comprising: first shape memory SM portion configured to apply an expanding force; and a polymer portion configured to resist expansion of the SM portion; the polymer portion having a non-uniform cross section including a peripheral layer composed mostly of a second polymer and a frame composed mostly of a first polymer; the second polymer having a greater environmental durability than the second polymer and wherein the first polymer has a higher creep resistance than the second polymer; wherein the polymer portion is configured to apply a contracting force when the polymer portion is mechanically coupled to the SM portion; and wherein the SM portion is pre-treated to have a decrease in SM portion expansion force as a function of a strain applied to the SM portion and to display a strain induced martensite behavior.

According to some embodiments of the invention, the polymer portion is formed by multi-layer coextrusion of at least a first layer including the peripheral layer and a second layer including the frame.

According to some embodiments of the invention, the peripheral face includes a second polymer and the frame includes a first polymer and wherein the second polymer has melt flow index (MFI) less than ⅔ of an MFI of the first polymer.

According to some embodiments of the invention, at least one of the peripheral layer and the frame maintains elasticity with a maximum residual strain of 30% after a 300% full strain.

According to some embodiments of the invention, at least one of the peripheral layer and the frame is configured for retaining the residual strain over at least 5 expand-collapse cycles to the full strain.

According to some embodiments of the invention, the structure further comprises a second peripheral layer and wherein the frame is disposed between the peripheral layer and the second peripheral layer.

According to some embodiments of the invention, the peripheral layer is composed at least 50% of a polymer having a greater environmental durability than the second polymer.

According to some embodiments of the invention, the structure is stable, over a plurality of different expansion states.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 27 is a simplified schematic cross section of a structure with more than two portions, according to some embodiments of the invention;

FIG. 28 is a simplified schematic cross section of a structure, according to some embodiments of the invention;

FIG. 29 is a simplified schematic cross section of a structure, according to some embodiments of the invention;

FIG. 44 is a flow chart of an exemplary method of treatment including deploying a structure within a lumen, according to some embodiments of the invention;

FIG. 57 is a flow chart showing a method of delivery and deployment of a structure, according to some embodiments of the invention;

FIG. 58 is a simplified schematic side view of a delivery system guided by an endoscope, according to some embodiments of the invention;

FIG. 59 is a simplified schematic side view of an endoscope delivery system, according to some embodiments of the invention;

FIG. 65 is a flow chart of a method of structure removal, according to some embodiments of the invention;

FIG. 66 is a simplified schematic cross sectional view of a removal system, according to some embodiments of the invention;

DESCRIPTION OF SPECIFIC EMBODIMENTS OF THE INVENTION

Figure 1A:
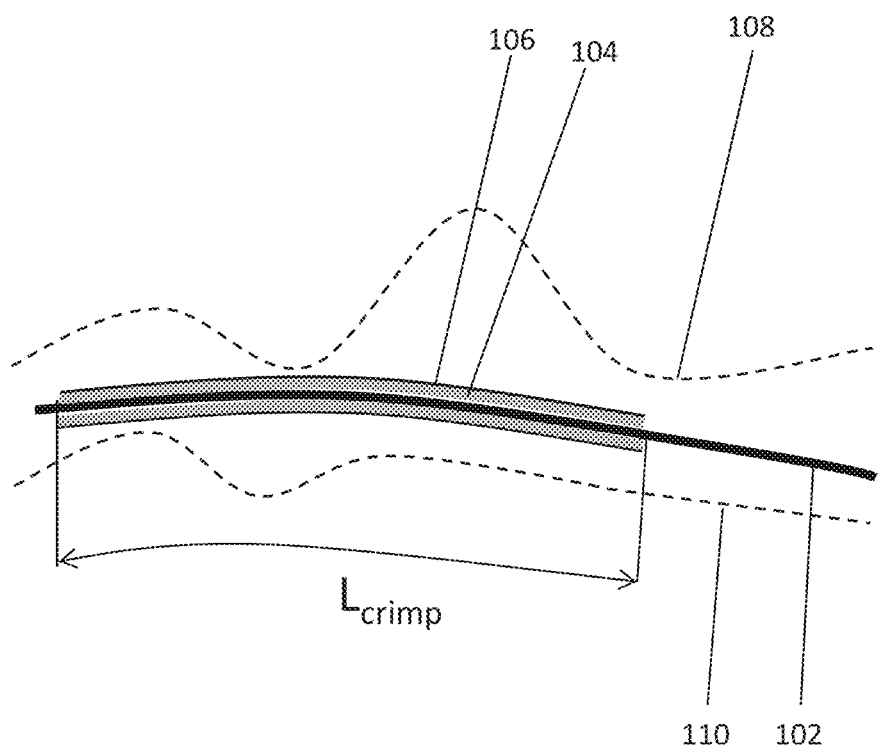
FIG. 1A is a simplified schematic cross sectional view of a structure in a crimped configuration within a lumen, according to some embodiments of the invention.

The present invention, in some embodiments thereof, relates to structures and methods for treating nasal conditions and, more particularly, but not exclusively, to structures and methods for treating sinusitis. Some embodiments are used for lumens other than nasal/sinus passages.

Overview

A broad aspect of some embodiments of the invention relates to treating nasal and/or sinus conditions by deploying a structure (e.g. a stent) within a lumen of the nasal cavity where the structure resists crushing and/or collapse, for example, holding the lumen open. In some embodiments, the structure is removed after a treatment time period.

In some embodiments, the structure is expanded within the lumen and the expanded structure maintains an expanded geometry, for example, withstanding pressure applied to the structure by the lumen. In some embodiments, the expanded structure is crush resistant, for example, returning to an expanded geometry after a dynamic change in pressure (e.g. during a sneeze). For example, in some embodiments, an expanded structure changes shape and/or partially collapses, e.g. due to swelling and/or inflammation of surrounding tissue, and upon reduction of swelling (e.g. due to healing), the structure returns to an expanded geometry.

In some embodiments, the structure is both deployable to a range of expanded geometries (the structure can be considered to be plastically deployable) and elastically resilient where the structure elastically returns to substantially an original geometry after being deformed (crush resistant) over this range of deployed geometries. For example, in some embodiments, In some embodiments, an extent to which an expanded structure conforms to a lumen geometry is selected. In some embodiments, the extent to which the expanded structure conforms to lumen geometry is controlled by selection of a suitable stent (e.g. materials, properties) and/or by an extent of deployment of the stent. In some embodiments, at least a portion of the structure (portion of a structure along a structure long axis) conforms to the lumen. For example, in some embodiments, the structure is expanded to a configuration within a sinus lumen which includes a varying cross-sectional area and/or shape along a structure length, matching a shape and/or size of the lumen. For example, in some embodiments, the structure bends to match a sinus lumen shape.

In some embodiments, a single expanded structure is expandable to a range of diameters where a largest expanded structure diameter is up to 10% or up to 50% or up to 100% or up to 200%, or up to 500%, or smaller, or larger, or intermediate percentages, larger than a smallest expanded structure diameter. A potential benefit of is the ability to expand the structure to a geometry which conforms to the lumen geometry. In an exemplary embodiment, a structure is expandable to up to a range of diameters of 4-10 mm. In some embodiments, a range of diameters (e.g. as described herein) is achieved with a segmented structure, where segments optionally have different characteristics (e.g. crimped diameter, deployed range of diameters, materials, material treatment (e.g. heat treatment), thickness).

In some embodiments, a pressure between one or more portion of the structure and the lumen is selected (e.g. outwards pressure of the structure and/or reactive pressure of the lumen on the structure). In some embodiments, the pressure is selected by the extent to which the structure conforms to the lumen, e.g. a structure expanded to a geometry which matches a lumen geometry substantially does not apply pressure to the lumen, e.g. a structure expanded to a geometry which is larger than the lumen applies an outwards force on the lumen and generates a reactive force and/or pressure on the structure from the lumen. In some embodiments, a structure is expanded to a geometry which is smaller than the lumen at one or more point, potentially meaning that the structure applies pressure to the lumen only upon swelling and/or inflammation and/or collapse of the lumen.

In some embodiments, the structure conforms to lumen geometry in substantially all directions perpendicular to a structure long axis; the structure cross section matches a lumen cross section. In some embodiments, the structure conforms to lumen geometry for a range of angles, e.g. the structure conforms to the lumen for a portion of a lumen cross section perimeter.

In some embodiments, the selected pressure that the expanded structure applies outwards on the lumen is less than 10 kPa, less than 5 kPa, less than 2.5 kPa, less than 1 kPa, less than 0.5 kPa. Potential advantages include reducing and/or preventing tissue edema, and/or tissue inflammation and/or embedding of the structure within the lumen (e.g. due to granulation tissue growth).

In some embodiments, a force and/or pressure required to expand the structure to a desired geometry is at most half, or at most a quarter, or at most a tenth, of a force required to collapse and/or crush the expanded structure (e.g. to half an expanded diameter or less).

A broad aspect of some embodiments of the invention relates to a structure configured for insertion into and/or removal from and/or positioning within the lumen, a potential benefit being minimal discomfort to the patient and/or lack of trauma to tissue.

In some embodiments, a structure and/or delivery system and/or retrieval system cross section is small, potentially facilitating insertion and/or removal and/or repositioning of the structure. For example, in some embodiments, a largest cross sectional measurement of a structure on a delivery system and/or retrieval system is less than 20 mm, or less than 10 mm, or less than 7 mm, or less than 5 mm, or less than 3 mm.

In some embodiments, a removal and/or delivery system cross section is sized for insertion into the lumen with another device (optionally, side by side with another device), for example, an imager (e.g. endoscope) and/or a light source.

In some embodiments, the structure is expanded gradually (e.g. using balloon expansion), for example, over a time duration of more than 0.1 second, or more than 0.5 seconds, or more than 1 second, or more than 5 seconds, or more than 1 minute, potentially facilitating accurate positioning, for example, for a time duration of 0.1-0.5 second, 0.5-1 second, 1-5 seconds, or shorter, or intermediate, or longer time durations. In some embodiments, the structure is expanded in more than one discrete expansion. Optionally, a user checks the structure geometry between discrete expansions, potentially facilitating accurate positioning of the structure.

In some embodiments, a structure length does not substantially change during expansion (e.g. as described herein, for example, with reference to FIG. 24 and FIG. 31), potentially facilitating accurate positioning.

In some embodiments, the expanded structure is collapsible, for example, collapses (e.g. self crimps) upon a temperature change, potentially facilitating removal and/or repositioning.

In some embodiments, for example, as the structure is easily inserted and/or positioned, the structure is inserted and/or removed in doctor's office e.g. without general and/or local anesthesia. In some embodiments, self-crimping and/or collapse of structures upon a temperature change facilitate stent removal, for example, during an office procedure without general anesthesia. In some embodiments, stent insertion and/or removal and/or repositioning is non-traumatic and is performed, for example, without general and/or local anesthesia.

In some embodiments, the lumen is pre-treated before the structure is deployed. For example, in some embodiments, a lumen is surgically treated and/or widened (e.g. during FESS) and one or more structure is deployed into the lumen as part of a surgical and/or post-operative procedure. A potential benefit being; maintained drainage and/or aeration of a sinus through the ostium, e.g. despite post-operative swelling. In some embodiments, the structure prevents post-operative stenosis and/or synechiae of the sinus ostium.

In some embodiments, a structure supports a lumen, for example, keeping the structure open and/or maintaining a geometry of the lumen, for example, maintaining a geometry of an operatively created lumen during healing (e.g. an enlarged sinus cavity after ethmoidectomy).

In some embodiments, a desired lumen shape is selected and a one or more structure is expanded within the lumen to the desired shape, for example, the structure is expanded by a suitably selected non-compliant balloon.

In some embodiments, a structure, once delivered to a desired position within a sinus ostium, is expanded to widen and/or open the lumen and/or change the shape of the lumen (e.g. push away inflamed tissue). For example, in some embodiments, deployment of one or more structure into one or more sinus lumen is employed as an alternative to surgical treatment of ostia. In some embodiments, the structure is expanded to a desired geometry (e.g. which does not match a portion of the lumen geometry) for example, by inflating a balloon (e.g. compliant and/or non-compliant balloon) inside the structure.

In some embodiments, one or more structure is deployed as a preventative measure. For example in some embodiments one or more structure is deployed into one or more lumen during and/or after surgery, potentially preventing complications such as stenosis (e.g. due to post-operative swelling). For example, in some embodiments, one or more structure is deployed into one or more lumen after trauma.

In some embodiments, the structure, in a crimped state, is sized and shaped for insertion into a sinus ostium. In some embodiments, the structure is sized and shaped for insertion into a surgically enlarged ethmoid sinus cavity.

In some embodiments, the structure is sized and shaped for insertion into a portion of a nasal cavity, for example a portion of the nasal cavity between a turbinate and a septum (e.g. to treat turbinate hypertrophy). In some embodiments, the structure between the turbinate and septum is flared in shape where the geometry widens, for example, in one or more direction around the narrowest portion of the lumen between the turbinate and the septum, e.g. anchoring the structure in position. E.g. the cross section of the structure widens above and/or below the largest portion of the turbinate.

In some embodiments, the structure is sized and shaped for insertion into a nasal valve. In some embodiments, the structure is deployed to a flared geometry (where flared corresponds to e.g. expanding cross section which refers to cross sectional perimeter length increasing and/or cross sectional area of a space enclosed by the perimeter of the structure increasing) where flaring increases towards the nostril.

In some embodiments, for example, where the lumen to be treated includes a corresponding lumen on the other side of the nose and/or head e.g. left and right nostril, a structure is inserted in to each of the two lumens or into a lumen on one side only e.g. in some embodiments, both the left and right nasal valves are stented e.g. in a preventatively after facial surgery.

In some embodiments, the structure includes open spaces, for example, is and is a mesh or lattice with multiple apertures therein and a coverage percentage of, for example, between 1% and 70%, for example, between 10% and 50%, for example, between 15% and 25%, a potential benefit being ability of air to circulate through the structure. For example, in some embodiments, a structure deployed within the nasal cavity (e.g. between a turbinate and a septum) allows free movement of air within the nasal cavity.

An aspect of some embodiments of the invention relates to deployment of a structure (e.g. as described herein) into a body lumen. For example, in some embodiments, a structure is deployed inside an Eustachian tube, a blood vessel (e.g. during combined percutaneous transluminal angioplasty (PCTA) and stenting), a biliary duct, a urethra, a ureter, a fallopian tube, an esophagus, colon tracts.

In an exemplary embodiment, a structure e.g. as described herein, is deployed inside a urethra after prostate surgery (e.g. prostatectomy) for example, to hold the urethra open (e.g. despite post-operative swelling) and/or to provide scaffolding for tissue growth along the urethral channel. In some embodiments, after a recovery time period, the structure is removed. In some embodiments, a structure which acts as scaffolding includes a cylindrical shaped SM mesh or lattice which is restrained by a polymer portion (e.g. balloon-like in shape), in some embodiments, the expanded structure is collapsed upon a temperature change.

An aspect of some embodiments of the invention relates to systems for delivery and deployment within and/or repositioning within and/or removal of structures from (e.g. structures as described herein) a lumen. In some embodiments, a delivery system includes a balloon surrounded at least partially with an elastic element which balloon and elastic element are placed inside a structure (e.g. as described herein). The delivery element is used to transfer the structure to a desired location within a lumen and inflation of the balloon elastically expands the elastic element, which expands the structure. In some embodiments, the elastic element transfers a low compliance balloon into a high compliance balloon for expanding the structure to a geometry conforming to the lumen geometry. In some embodiments, the elastic element elastically relaxes, causing the balloon to deflate, once internal balloon pressure is reduced. In some embodiments, the system includes element/s for effecting a structure temperature change (e.g. pipe/s for applying cooled fluid to the structure).

In some embodiments, the structure is collapsed by inflating the balloon with cooled fluid, at sufficiently low pressure that collapse of the structure onto the balloon deflates the balloon and/or the balloon doesn't prevent collapse of the structure.

An aspect of some embodiments of the invention relates to a structure including polymer (e.g. only polymer) which is elastically expandable for short expansion times, but maintains an expanded state after a minimum expansion time period has been exceeded. A potential benefit is ease of positioning and/or repositioning of the structure. In some embodiments, the structure collapses from an expanded state upon experiencing a temperature change (e.g. of temperatures above body temperature).

An aspect of some embodiments of the current invention relates to a composite highly durable hollow body having high recoil and/or a low creep elastic wall and/or walls. For example, the wall may include a high recoil and/or low creep frame (for the sake of the current disclosure term frame may include a core for example of a filament and/or an inner layer of a wall, a layer of a wall, a collection of veins and/or filaments for example forming a skeleton of a wall, a substructure and/or a substratum). Optionally the wall may include a flexible environmentally resistant peripheral layer. Optionally the wall may have a layered structure for example including a high recoil and/or low creep elastic frame and an environmentally resistant flexible peripheral layer. The frame is optionally sandwiched between two peripheral layers. Alternatively or additionally the frame may form the inner surface of the hollow lumen of the body. Alternatively or additionally the wall may include filaments. Optionally a filament may be a simple and/or composite. For example, a composite filament optionally includes a high recoil and/or low creep elastic core and/or a flexible environmentally resistant peripheral layer. Optionally filaments may be formed into a layer in the wall. For example filaments may be woven together and/or formed into a lattice and/or a net and/or a grid. Alternatively or additionally, frame filaments may be embedded in peripheral layers. In some embodiments, the elastic body may be included in an elastic portion and/or a polymer portion of a shape changing structure for example an expandable structure. For example, the shape changing structure may include a stent and/or a catheter.

In some embodiments, the mechanical properties of the elastic body are tailored to a physical load and external properties tailored to an application and/or environment. For example, the mechanical properties may be configured to balance an expandable shape memory device. Optionally, properties may vary over the cross section of the wall of the body. For example a peripheral layer may have desirable environmental resistance properties and/or biocompatibility. Optionally, the frame may have desirable mechanical properties, for example a high creep resistance and/or elasticity and/or recoil. For example the frame may include a first polymer and/or the peripheral layer may include a second polymer. Optionally the first polymer may have the desired mechanical properties (for example high creep resistance and/or high recoil). For example the second polymer may have the desired environmental properties (for example durability, biocompatibility). For example, each of the layers may comprise between 10 to 30% and/or between 30 to 50% and/or between 50 to 70% and/or between 70 to 90% and/or between 90 to 100% the respective polymer. Optionally, the concentration of the first polymer in the frame may range between 1 to 1.5 times and/or 1.5 to 2 times and/or 2 to 3 times and/or 3 to 5 times and/or greater than 5 times the average concentration in the peripheral layer. Optionally, the concentration of the second polymer in the peripheral layer may range between 1 to 1.5 times and/or 1.5 to 2 times and/or 2 to 3 times and/or 3 to 5 times and/or greater than 5 times the average concentration in the frame.

In some embodiments, the composite body may be formed of discrete homogenous layers. For example a peripheral layer may have a thickness between 5 to 15 µm and/or between 15 to 25 µm and/or between 25 to 40 µm and/or between 40 to 100 µm and/or between 100 µm to 1 mm. For example a frame may have a thickness and/or diameter between 10 to 20 µm and/or between 20 to 50 µm and/or between 50 to 100 µm and/or between 100 to 500 µm and/or between 500 µm to 4 mm. For example, the thickness of the peripheral layer may be between 5 to 20% and/or 20 to 50% and/or 50 to 75% and/or 75 to 90% and/or 90 to 100% and/or 100% to 400% the thickness and/or diameter of the frame. Alternatively or additionally the composition and/or the structure wall may change gradually across its cross section. For example, the core of the wall may include a high concentration of a first polymer (for example a high recoil and/or low creep polymer). Optionally the concentration of the first polymer may gradually be reduced along the cross section of the wall from the core to the periphery. Optionally the concentration of a second polymer may gradually increase along the cross section of the wall from the core to the periphery. For example the second polymer may be environmentally resistant. Alternatively or additionally the composition and/or the structure wall may change gradually across the axis of the body and/or circumferentially.

In some embodiments, the frame may have a higher creep resistance than a peripheral layer. For example a frame may comprise mostly a lower molecular weight (MW) polymer (for example lower MW Carbotane®, Tecoflex® and/or Tecothane®). For example a peripheral layer may include mostly a higher MW polymer (for example higher MW Carbotane® and/or Chronoflex®). For example the frame may have residual strain between 5 to 15% of a total strain (for example when stretched to 300% of its original length it may recoil to between 15 to 45% strain) and/or between 15 to 30% (for example when stretched to 300% of its original length it may recoil to between 45 to 90% strain) and/or between 30 to 60% (for example when stretched to 300% of its original length it may recoil to between 90 to 180% strain). For example, the residual strains listed above may be after stretching at the total strain for less than 1 second and/or between 1 sec to 1 minute and/or between 1 minute to 1 hour and/or between 1 hour to 1 day and/or between 1 day to 1 week and/or between 1 week to 1 month and/or between 1 month to 2 months and/or between 2 months to 6 months and/or between 6 months to one year. For example the frame may retain its recoil properties, for example as described above, over one and/or at least 3 and/or at least 5 and/or at least 10 and/or at least 40 and/or at least 100 expand collapse (e.g. recoil) cycles. For example the frame may have a higher meltflow index (MFI) than the peripheral layer. Optionally the MFI of the peripheral layer may be between 1/10 to 1/3 to 3/7 and/or 3/7 to 47 and/or 4/7 to 2/3 and/or 2/3 to 9/10 of the MFI of the frame.

In some embodiments, the physical properties listed above (for example the residual strain and recoil) may be exhibited at body temperature and/or at a temperature of collapsing of a the SM portion of a stent. For example at temperature between 0 to 5 and/or 5 to 15 and/or 15 to 25 and/or 25 to 35 degrees Celsius.

In some embodiments, the properties of the frame may apply to the polymer from which it is composed. Optionally, the properties of the peripheral layer may apply to the polymer from which it is composed. Optionally, the properties of the polymer from which the frame is composed may apply to the frame. Optionally, the properties of the polymer from which the peripheral layer is composed may apply to the peripheral layer.

In some embodiments, the peripheral layer will have a higher environmental resistance than the frame. For example, the peripheral layer may be configured to withstand an intended environment (such as a nasal cavity and/or a body lumen) for between 1 day to 1 week and/or 1 week to 1 month and/or 1 month to 2 months and/or between 2 months to 6 months and/or between 6 months to 1 year. Optionally the lifetime of the peripheral layer in the chosen environment may be between 100 to 10 times and/or 10 to 3 times and/or 3 to 1.5 times and/or 1.5 to 1.1 times as long as the lifetime of the frame under the chosen conditions. Optionally the peripheral layer may have a degradation rate under the chosen environment that is between 1/100 to 1/10 and/or 1/10 to 1/3 and/or 1/3 to 2/3 and/or 2/3 to 9/10 as fast as degradation of the frame under those conditions. For example, the degradation of the peripheral layer may be slow for Oxidation and/or due to enzymes and/or microphages and/or due to metal ion oxidation MIO. For example the peripheral layer may be more resistant to environmental stress cracking (ESC) than the frame.

Optionally the layers of the composite elastic structure are coextruded. In some embodiments, the elastic structure may include an elastic tube and/or a sheath for an expandable structure including a first SM portion. For example, coextruded materials may be chosen to have similar melting points and/or adhesion properties.

In some embodiments, the periphery layer may be made of a high friction material. Optionally, high friction may prevent movement of the elastic element with respect to the SM element of an expanding and/or shape changing device. For example, the coefficient of friction between the SM portion and the elastic portion may range between 0.1 to 0.05 and/or 0.05 to 0.75 and/or between 0.75 to 1.0 and/or between 1 to 1.5 and/or between 1.5 to 2.0.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Method of Treatment

Figure 43:
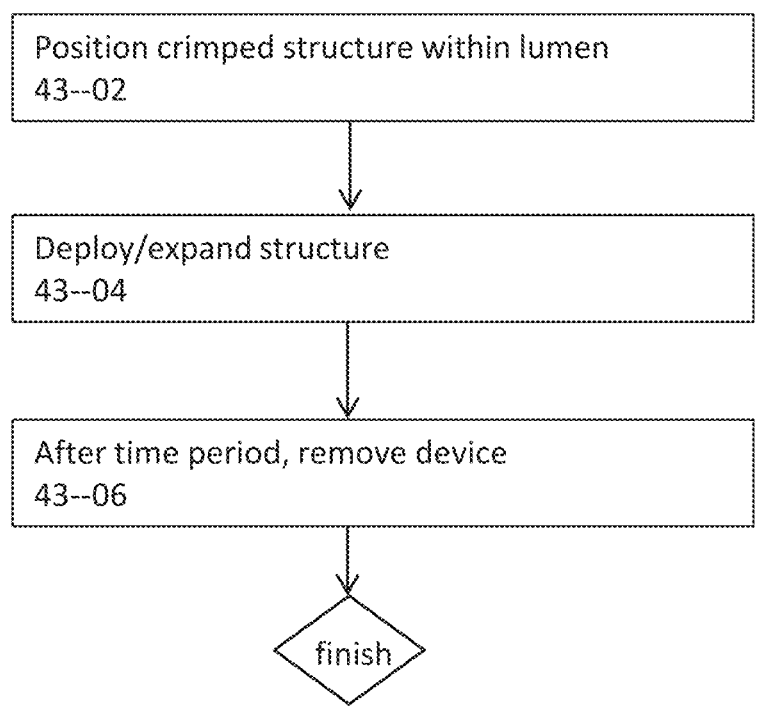
FIG. 43 is a flow chart of a method of deploying a structure in a lumen according to some embodiments of the invention.

FIG. 43 is a flow chart of a method of deploying a structure in a lumen according to some embodiments of the invention.

At 4302, a structure (e.g. as described herein) is delivered to a desired location within a lumen e.g. by a delivery system. In some embodiments, the structure is delivered to the desired location in a crimped configuration. In some embodiments, the structure is sized for insertion into the desired lumen and/or lumens passed through to arrive at the desired lumen. For example, in some embodiments, a largest cross sectional measurement of the crimped structure mounted on the delivery device is small with respect to the lumen cross section and/or cross sections of lumens passed through to arrive at the desired location (e.g. structure largest cross sectional measurement is less than of, less than 70% of, less than 30% of lumen smallest or average cross sectional measurement).

At 4304, the structure is expanded within the lumen, for example, supporting and/or widening the lumen. In an exemplary embodiment, one or more part of the structure matches and/or conforms to the lumen, applying substantially no outwards pressure on the lumen, for example less than 10 kPa, less than 5 kPa, less than 2.5 kPa, less than 1 kPa, less than 0.5 kPa.

At 4306, after a time delay in which, for example, the lumen heals, the structure is removed e.g. using a removal system. In some embodiments, the removal system is sized for insertion into the desired lumen and/or lumens passed through to arrive at the stented lumen. In some embodiments, the structure self collapsed to a crimped or near-to crimped configuration. Alternatively, in some embodiments, the structure is permanently left within the lumen.

In some embodiments, the structure is deployed gradually and/or in a controlled manor potentially assisting accurate deployment (e.g. expansion and/or conforming and/or position within the lumen) For example, over a time period, for example, in discrete expansions where position and/or expansion are checked in between expansions.

In some embodiments, the structure is elastically crush resistant, for example, the structure is compressed e.g. by swelling of tissue and returns substantially to an original expanded geometry after swelling subsides.

FIG. 44 is a flow chart of an exemplary method of treatment including deploying a structure within a lumen, according to some embodiments of the invention. Some of the herein described steps are optional.

Diagnosis

At 4402, a patient is diagnosed with a condition suitable for treatment with structures according to some embodiments of the invention, for example, treatment involving deployment of one or more structure within one or more ostium.

In some embodiments, a diagnosis is made based on failure of one or more treatment to resolve a condition, for example, failure of systemic medication (e.g. with steroids and/or antibiotics) to resolve sinusitis.

In some embodiments, a diagnosis is made using one or more type of imaging e.g. CT, MRI, endoscopy, ultrasound. For example, in some embodiments, stenosis and/or synechiae of one or more ostium and/or blockage and/or poor drainage of sinuses is diagnosed by imaging (e.g. CT and/or MRI and/or endoscopic imaging).

In some embodiments, no diagnosis is made and treatment is part of preventative treatment, for example, insertion of one or more structure after and/or during rhinoplasty (e.g. to prevent post-operative complications).

Selection of Treatment

At 4406, a treatment, for example, based on a diagnosis, is selected. In some embodiments, one or more nasal lumen to be treated is selected e.g. nasal cavity, e.g. ethmoid sinus, e.g. one or more ostium. In some embodiments one or more portion of a nasal lumen to be treated is selected e.g. nasal valve and/or between a turbinate and the septum. In some embodiments, a number of ostia to be treated is selected. In some embodiments, a number of structures to be inserted into each lumen to be treated is selected. In some embodiments, dimensions for each structure to be inserted are selected.

In some embodiments, a type (e.g. material type, e.g. dimensions) of each structure to be inserted is selected. In some embodiments, a structure is non-symmetrical in a crimped state and/or has non-symmetrical material properties (e.g. thickness of SM and/or polymer portion is non-symmetrical).

At 4408, in some embodiments, areas to be treated are imaged, for example, providing information for selection of a desired position within lumens/s and/or selection of structure type e.g. using CT and/or MRI and/or endoscopy.

Pre-Treatment

At 4410, in some embodiments, one or more area is pre-treated. In some embodiments, pre-treatment includes surgically widening, for example, of one or more ostium and/or of one or more sinus e.g. during FESS. In some embodiments, pre-treatment includes surgically creating a nasal lumen, for example, during ethmoidectomy where, in some embodiments, two or more ethmoid sinuses are merged into a single nasal lumen.

In some embodiments, pre-treatment includes non-surgical widening, for example, of one or more ostium, e.g. by inflation of a balloon.

In some embodiments, pre-treatment includes cleaning and/or draining, for example ostia and/or sinuses to be treated (e.g. by irrigation with saline).

In some embodiments, pre-treatment includes anesthetizing one or more area, for example, locally anesthetizing an ostium (e.g. one or more portion of an ostium).

Delivery and Deployment

At 4412, a structure (e.g. as described herein) is delivered to an area to be treated, e.g. to a desired position within an ostium. In some embodiments, delivery to a desired position is assisted by imaging e.g. endoscopy, ultrasound where, for example, images provide visual feedback to a user which guide positioning of the structure. In some embodiments, one or more part of a structure and/or delivery system is radiopaque and delivery of the structure to a desired area is assisted by CT and/or X-ray imaging, where, for example, images provide visual feedback to a user positioning the structure.

At 4414, the structure is deployed by expanding the structure within the lumen. For example, in some embodiments, the structure is expanded by inflating a balloon located inside the structure. Optionally, imaging (e.g. as described above) provides visual feedback to a user guiding expansion of the structure (e.g. a user uses images to ascertain when a structure is expanded sufficiently to conform to the lumen).

Optionally, in some embodiments, delivery and/or deployment of a structure is combined and/or closely follows a pre-treatment. For example, in some embodiments, an ostium is surgically widened, and soon after a structure is deployed at the surgically widened portion of the ostium.

Alternatively, in some embodiments, there is no pre-treatment and a structure is deployed in an untreated area. For example, in some embodiments, a structure is deployed within an ostium, the expansion of the structure opening and/or widening the ostium (e.g. treatment by deployment of a structure is instead of FESS).

Optionally, at 4416, in some embodiments, a location and/or geometry (e.g. whether the structure conforms sufficiently to the lumen, e.g. whether the structure widens the lumen sufficiently) of the expanded structure is checked, for example, using imaging.

Re-Deploying

In some embodiments, at 4418, the structure is repositioned and/or re-expanded, optionally in view of previous checking. Optionally, the repositioned and/or re-expanded structure is then checked again e.g. using imaging.

In some embodiments, a structure is re-deployed by self-crimping the structure, for example, to a size (e.g. diameter) suitable for moving the structure within the lumen. In some embodiments, e.g. as described herein, the structure is self crimped to a size significantly larger than a crimped size (e.g. diameter is up to 25% larger, e.g. 5-50% larger than a crimped state diameter).

Once structures are deployed according to the selected treatment each structure is left in position for a desired time duration. In some embodiments, all structures are removed after a desired time duration. Alternatively, in some embodiments, different structures are left in position for different time periods. In some embodiments, a structure is left in a first position for a first time period and then re-deployed in a second position for a second time period.

In some embodiments, the structure is not removed but falls out, for example, upon dissolving of sutures keeping the structure in position, for example, upon reduction in swelling of the lumen.

Exemplary Types of Treatment

Structure/s within Nasal Lumens, Exemplary Positions

In some embodiments, structures described herein are suitable for deployment adult human lumens, for example, adult human nasal lumens. In some embodiments, structures are sized to be suitable for insertion into children and/or infant body lumens.

Nasal Cavity

Figure 45A:
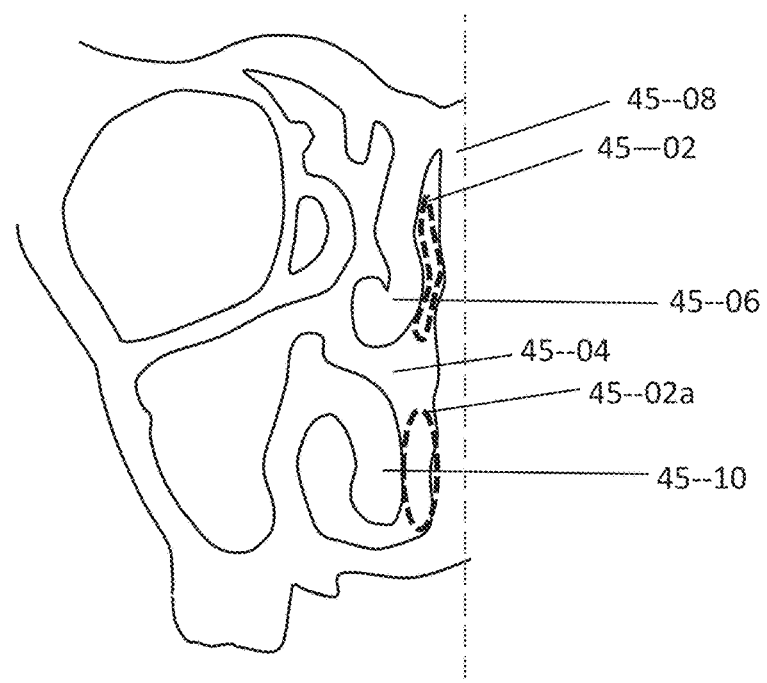
FIG. 45A is a simplified schematic coronal view of a portion of the head with structures deployed in the nasal cavity, according to some embodiments of the invention.

In some embodiments, a structure (e.g. as described herein) is deployed in the nasal cavity between a turbinate and the nasal septum, for example, to prevent adhesion of the turbinate to the septum. Optionally, in some embodiments, before deploying the structure, the turbinate is separated from the septum and/or a separation between the turbinate and septum is widened (e.g. during FESS). FIG. 45A is a simplified schematic coronal view of a portion of the head with cross sectional views of structures 4502*a*, 4502 deployed in the nasal cavity 4504, according to some embodiments of the invention.

Figure 45B:
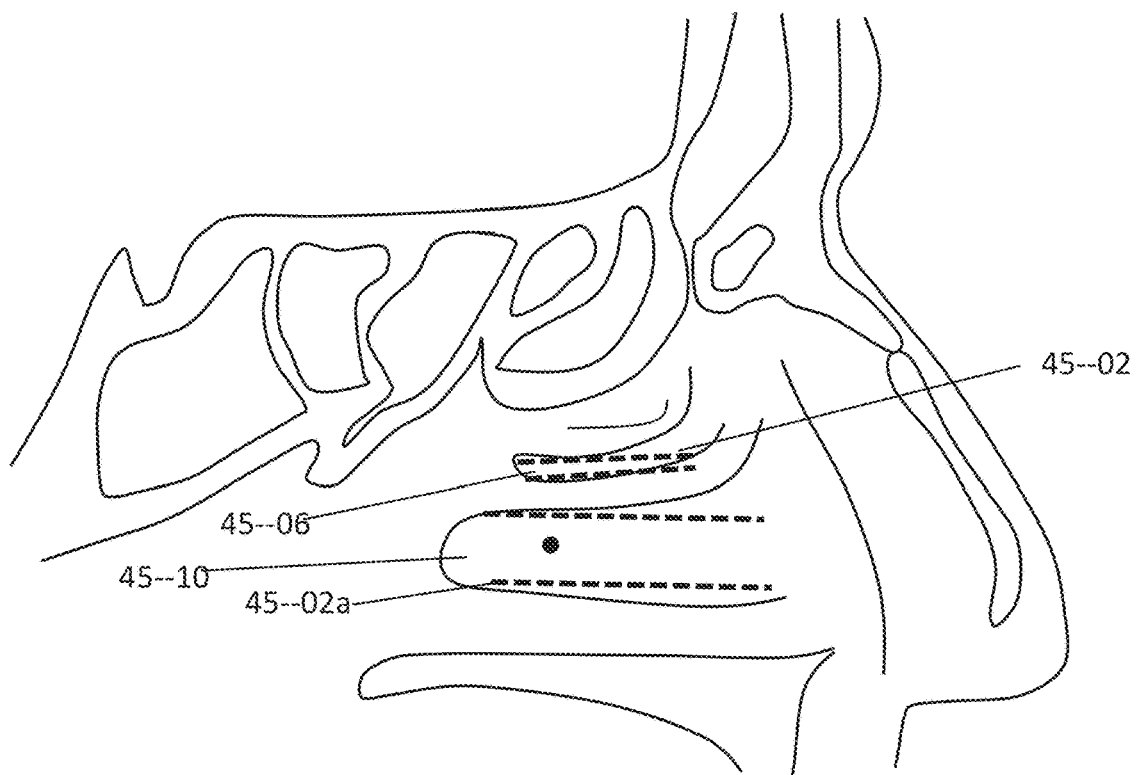
FIG. 45B is a simplified schematic sagittal view of a portion of a head, with structures deployed in the nasal cavity, according to some embodiments of the invention.

FIG. 45B is a simplified schematic sagittal view of a portion of a head, with cross sectional views of structures 4502, 4502*a* deployed in the nasal cavity, according to some embodiments of the invention.

In some embodiments, a first structure 4502 is deployed between a middle turbinate 4506 and a nasal septum 4508. Additionally or alternatively, in some embodiments, a second structure 4502*a* is deployed between an inferior turbinate 4510 and septum 4508.

In an exemplary embodiment, a method of treatment of nasal conditions includes delivering an expandable structure to a portion of a nasal cavity between a turbinate and a septum (e.g. through a nostril), expanding the structure to a geometry which optionally conforms to a portion of the nasal cavity geometry, and, after a time period, removing the structure (e.g. by causing the structure to self-collapse).

Ethmoidectomy

Figure 46A:
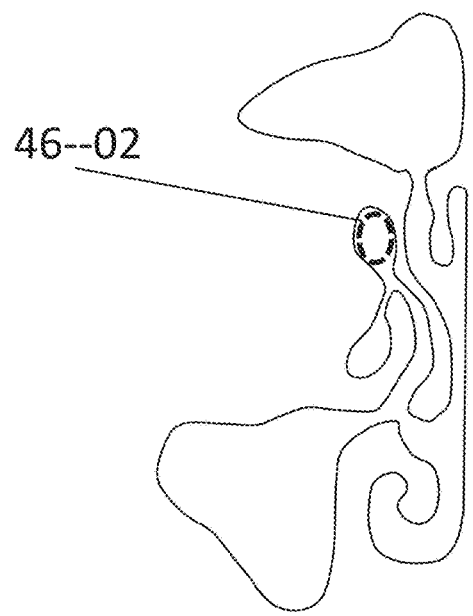
FIG. 46A is a simplified schematic coronal view of a portion of the head with a structure deployed within the ethmoid area, after ethmoidectomy, according to some embodiments of the invention.
Figure 46B:
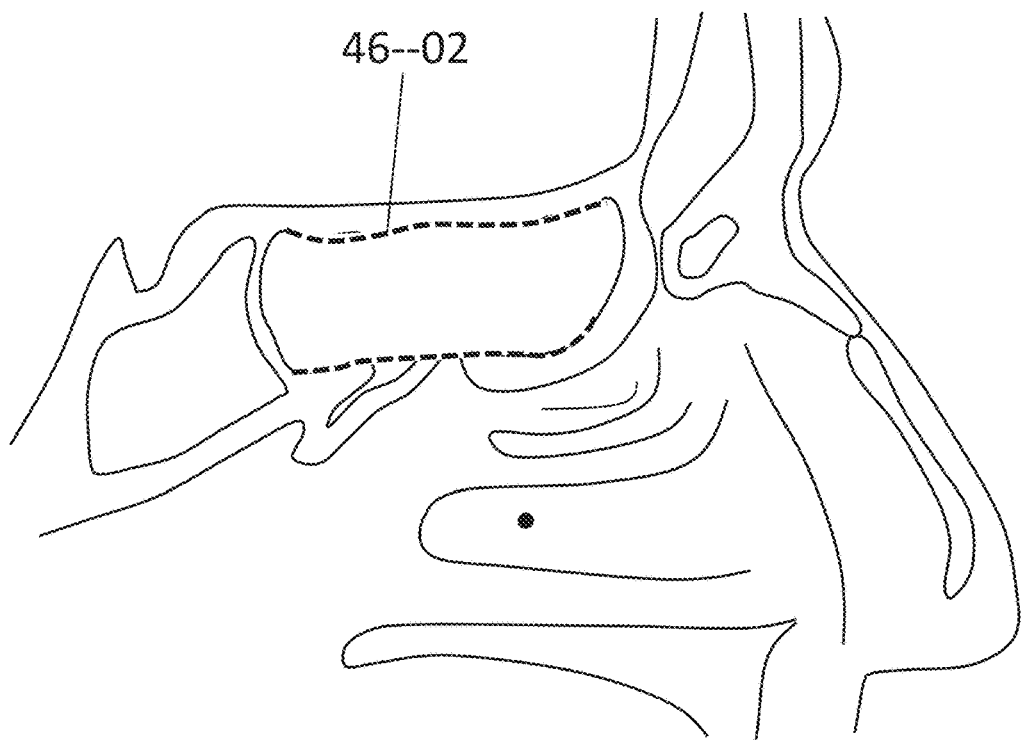
FIG. 46B is a simplified schematic sagittal view of a portion of the head with a structure deployed within the ethmoid area, after ethmoidectomy, according to some embodiments of the invention.

In some embodiments, a structure (e.g. as described herein) is deployed into the ethmoid sinus area after an ethmoidectomy. For example, in some embodiments, ethmoid sinus tissue and bone are removed, and, following tissue removal, a structure is expanded into the ethmoid area. FIG. 46A is a simplified schematic coronal view of a portion of the head with a structure 4602 deployed within an ethmoid area, after ethmoidectomy, according to some embodiments of the invention. FIG. 46B is a simplified schematic sagittal view of a portion of the head with a structure 4602 deployed within the ethmoid area, after ethmoidectomy, according to some embodiments of the invention.

In an exemplary embodiment, a method of treatment of nasal conditions includes surgically removing tissue (e.g. bone, epithelium) from an ethmoid sinus region (e.g. ethmoidectomy), delivering an expandable structure (e.g. through the nostril and nasal cavity) to the surgically created lumen, expanding the structure, optionally to a geometry which conforms to the surgically created lumen, and removing the structure, optionally by causing the structure to self-crimp. Optionally, in some embodiments, tissue is not removed, and a natural sinus is shaped.

Nasal Valve

Figure 47:
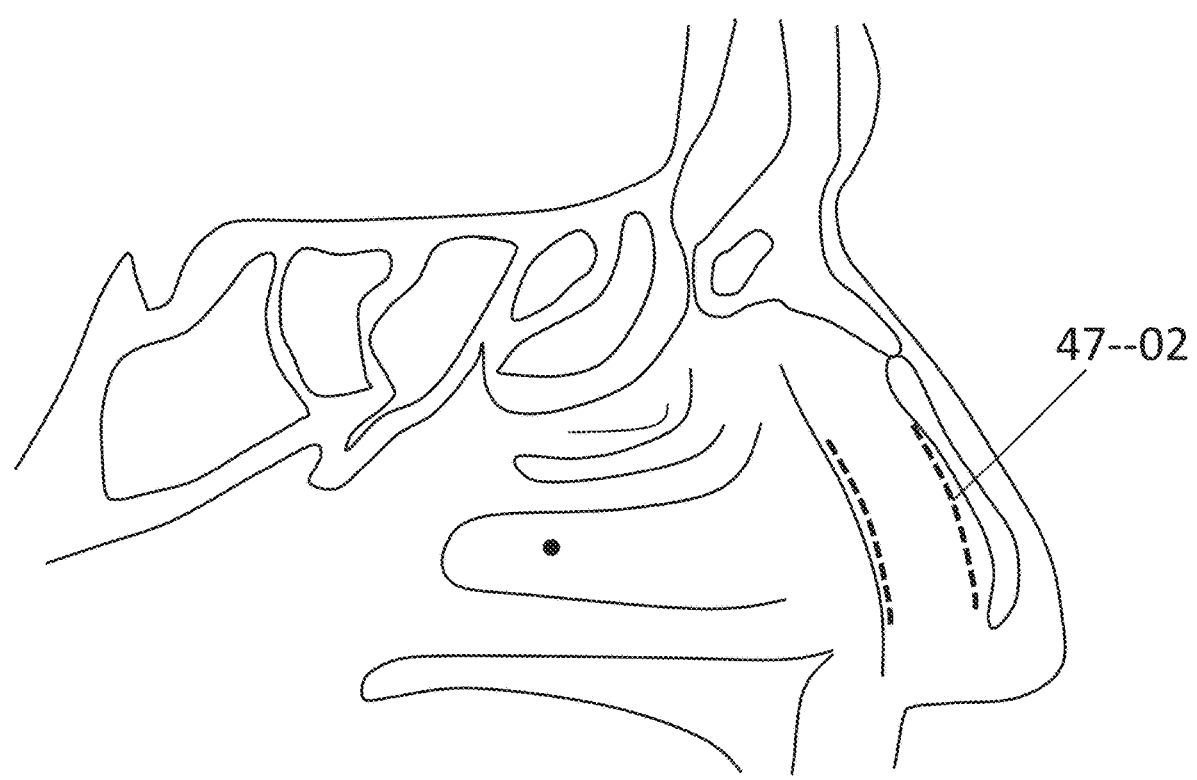
FIG. 47 is a simplified schematic sagittal view of a portion of the head, with a structure deployed keeping the nasal valve open, according to some embodiments of the invention.

In some embodiments, a structure is expanded inside the nasal valve (e.g. after surgery, e.g. after trauma), keeping the nasal valve open. FIG. 47 is a simplified schematic sagittal view of a portion of the head, and a cross sectional view of a structure 4702 deployed keeping the nasal valve open, according to some embodiments of the invention.

In an exemplary embodiment, one or more structure is deployed in the nasal cavity after a rhinoplasty and/or facial surgery procedure, potentially preventing complications such as nasal lumen stenosis (e.g. nasal valve stenosis) (e.g. due to post-operative swelling and/or scaring and/or following healing).

In an exemplary embodiment, a method of treatment of nasal conditions and/or preventative treatment of post-operative nasal complications includes delivering an expandable structure to a nasal lumen in a region of a nasal valve and expanding the structure to a geometry which optionally matches at least a portion of the nasal lumen geometry and, after a time period, removing the structure (e.g. by causing the structure to self-collapse).

Sinus Ostia

In some embodiments, one or more structure is deployed in one or more ostium connecting a sinus to the nasal cavity. In some embodiments, one or more structure is deployed in one or more ostium connecting a sinus to another sinus (e.g. ethmoid sinus to maxillary sinus). In some embodiments, one or more structure is deployed in one or more ostium connecting a first sinus to a second sinus.

Figure 48A:
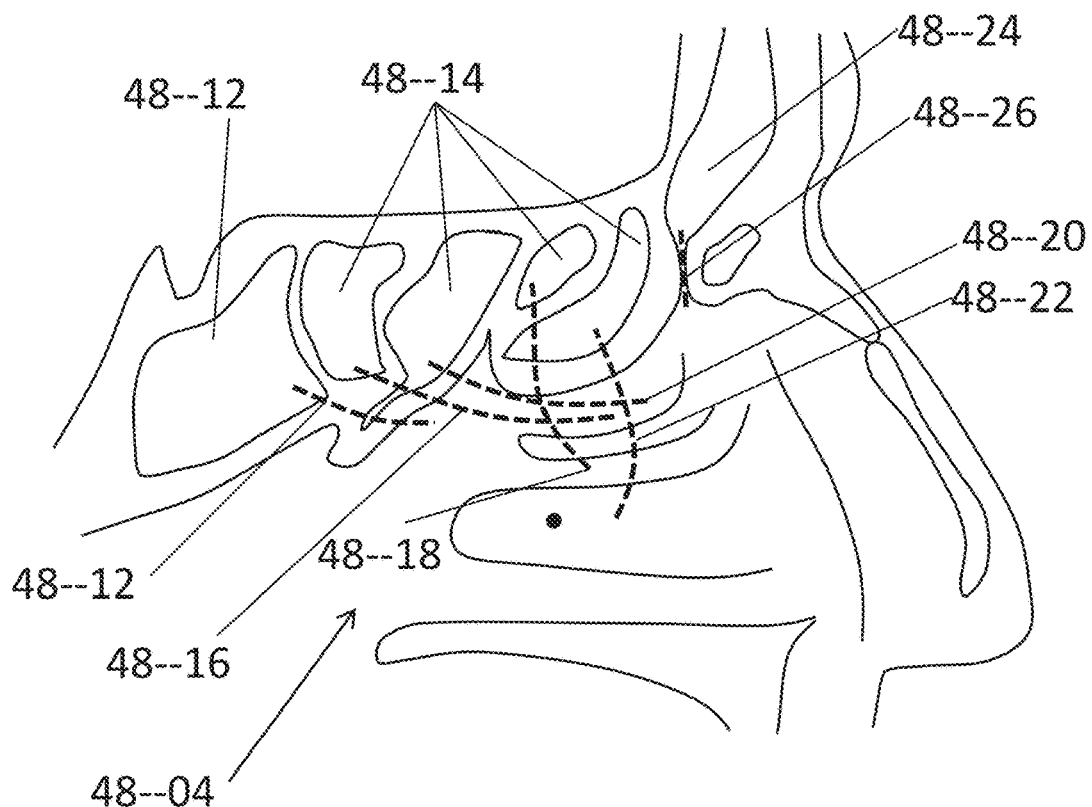
FIG. 48A is a simplified schematic sagittal view of a portion of the head where structures are deployed in sinus ostia, according to some embodiments of the invention.
Figure 48B:
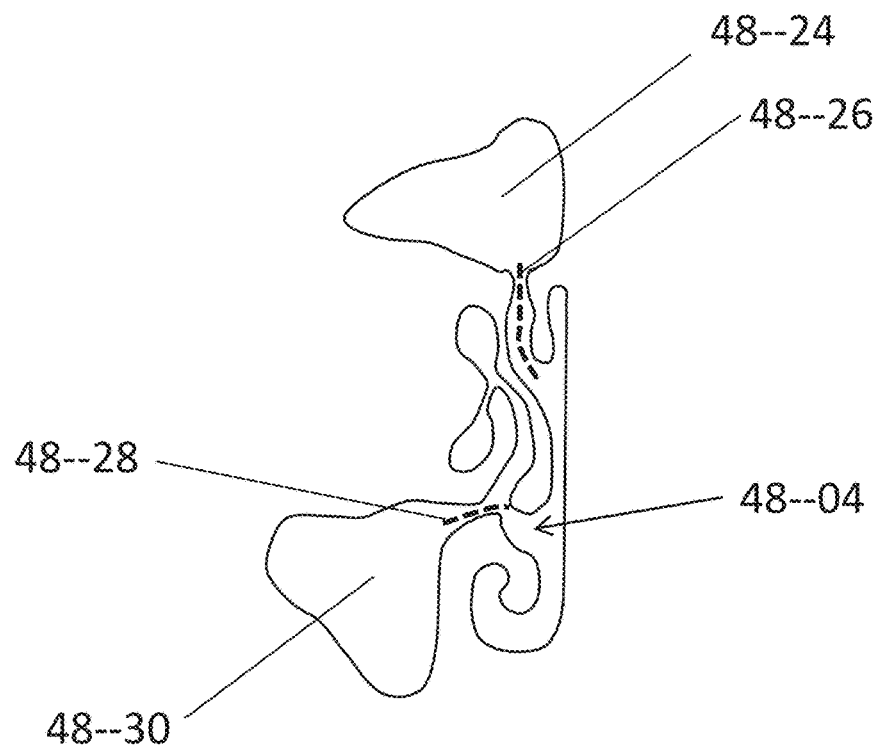
FIG. 48B is a simplified schematic coronal view of a portion of the head where structure are deployed in sinus ostia, according to some embodiments of the invention.

FIG. 48A is a simplified schematic sagittal view of a portion of the head where structures are deployed in sinus ostia, according to some embodiments of the invention. FIG. 48B is a simplified schematic coronal view of a portion of the head where structure are deployed in sinus ostia, according to some embodiments of the invention. Structures illustrated in FIG. 48A and FIG. 48B show exemplary positions for deployment of structures.

In some embodiments, one or more structure 4812 is deployed into an ostium connecting a sphenoid sinus 4812 to a nasal cavity 4804.

In some embodiments, one or more structure 4816, 4818, 4820, 4822 is deployed connecting an ethmoid sinus 4814 to nasal cavity 4804.

In some embodiments, one or more structure 4826 is deployed connecting a frontal sinus 4824 to nasal cavity 4804.

Referring to FIG. 48B, in some embodiments, one or more structure 4828 is deployed connecting a maxillary sinus 4830 to nasal cavity 4804.

Structure/s within a Lumen

Figure 49:
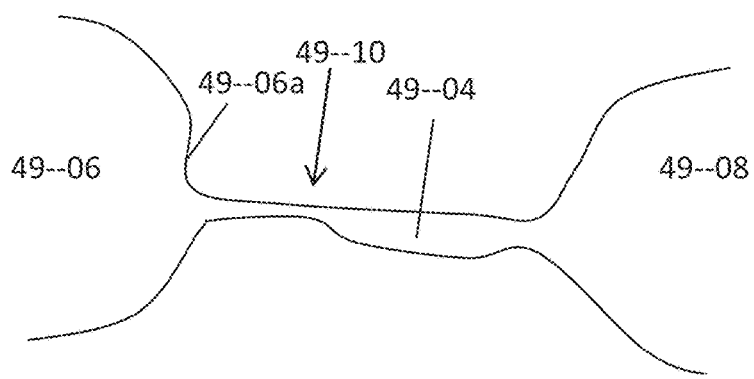
FIG. 49 is a simplified schematic cross sectional view a sinus connected to a nasal cavity by an ostium.

FIG. 49 is a simplified schematic cross sectional view of a sinus 4906 connected to a nasal cavity 4908 by an ostium 4904. Ostium 4904 includes a narrow portion 4910. FIGS. 50-56 show embodiments of structures within the lumen illustrated by FIG. 49.

Location, Extent of Structure within Lumen

In some embodiments, a location and/or extent of a structure within a lumen (e.g. a sinus ostium) is selected, for example, by selecting a size (e.g. length of the structure), for example by deploying the structure to a selected extent. In some embodiments, a structure is deployed within a portion of a lumen, for example, at a lumen narrowing. In some embodiments, a structure is deployed within less than 10% or less than 30%, or less than 50% or less than 70% of a lumen long axis length.

In some embodiments, a structure is deployed within substantially all of a lumen. For example, as illustrated by FIGS. 50, 51, 53, 54, 55 and 56.

In some embodiments, a structure extends outside of a target lumen into one or more connected lumens (e.g. the structure within ostium extends into a sinus and/or a nasal cavity). For example, as illustrated by FIGS. 51, 52, 54 and 55.

In some embodiments, more than one structure is deployed within a single lumen, for example, to support the whole lumen where a length of a deployed structure is less than the length of the lumen, for example, in order to leave one or more portion of the lumen "un-stented" (e.g. without support of a structure).

Extent of Structure Conformation to Lumen

In some embodiments, an extent to how much a structure conforms and/or matches a lumen geometry is selected. In some embodiments, a level of outwards force and/or pressure applied to the lumen by the structure is selected.

In some embodiments, a structure matches and/or conforms to a lumen geometry in substantially all directions, for example, a structure which, in a crimped state, is ball shaped, is expanded in all directions to conform to a lumen into which it is delivered. In some embodiments, the structure conforms to the lumen in some directions and not in other directions e.g. the lumen is cylindrical and the structure has oval cross section.

In an exemplary embodiment, the structure matches lumen geometry substantially without applying outwards force to the lumen, for example, applying an outwards force of less than 2N, or less than 1N, or less than 0.5N, or less than 0.25N, or less than 0.1N.

In some embodiments (e.g. as described herein), a cross section of one or more part of the structure includes a polygon shape where corners of the polygon are defined by the SM portion (e.g. SM portion struts). In some embodiments, the structure applies different pressures to different parts of the lumen, for example, higher pressure where SM portions contact and/or are in proximity to (e.g. separated from the lumen by a portion of the polymer portion) the lumen walls (e.g. polygon corners).

In some embodiments, a proportion of a stented lumen cross-section which is contacted by the structure (e.g. due to non-complete coverage of the structure and/or non conforming of the structure) is 10-90%, In some embodiments, the structure matches and/or conforms to an original (before structure insertion) geometry. For example, because the structure matches and/or conforms to the original lumen geometry, the structure does not apply outwards force to the lumen and the lumen does not apply reactive force and/or pressure to the structure. In some embodiments, this condition is met initially, but changes with time. For example, where pressure on the structure from the lumen increases due to post-operative swelling and/or decreases after healing.

In some embodiments, the lumen anatomy which is matched is an original lumen anatomy, before treatment (e.g. in a facial plastic surgery treatment where structure deployment, in some embodiments, is to maintain drainage and/or air flow despite postoperative swelling). In some embodiments, the lumen anatomy which is matched is a post operative lumen anatomy (e.g. the lumen created in ethmoidectomy e.g. the a surgically widened sinus ostium).

In some embodiments, one or more portion of a structure conforms to a geometry of a lumen, where the conforming portion of the structure e.g. 5002 is within 1-2 mm or 0.5-1 mm or 0.25-0.5 mm or 0.1-0.25 mm or 0.05-0.1 mm of lumen walls e.g. 5004a. In some embodiments, one or more portion of a structure partially conforms to a geometry of a lumen, where the partially conforming portion of the structure e.g. 5502a is within 2-4 mm, 1-2 mm or 0.5-1 mm or 0.25-0.5 mm of the lumen walls 5508a. In some embodiments, partial conforming includes conforming in some directions and not in other e.g. the lumen is cylindrical and the structure has oval cross section. For example, in some embodiments, a structure partially conforms where 5-10%, or 10%-50%, or 50%-90% of a cross sectional circumference of a lumen is matched and/or contacted by the structure. Where the structure includes non-solid walls (e.g. one or more portion of the structure is a mesh) conforming percentages refer to the percentage of a solid perimeter of the structure which is in contact with the lumen. For example, referring to FIG. 41, structure cross section illustrated conforms 100% to the lumen if both 1 mm section 4106 contact the lumen along their entire length.

Figure 50:
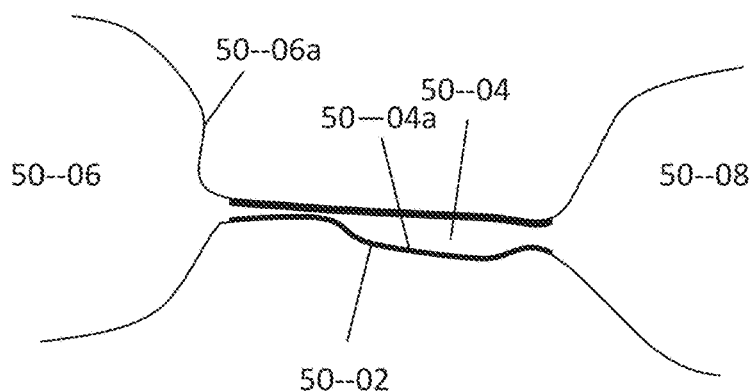
FIG. 50 is a simplified schematic cross sectional view of an expanded structure within substantially an entire length of an ostium, where the structure conforms to a geometry of the ostium, according to some embodiments of the invention.

FIG. 50 is a simplified schematic cross sectional view of an expanded structure 5002 within substantially an entire length of an ostium 5004, where the structure conforms to a geometry of the ostium, according to some embodiments of the invention.

Figure 51:
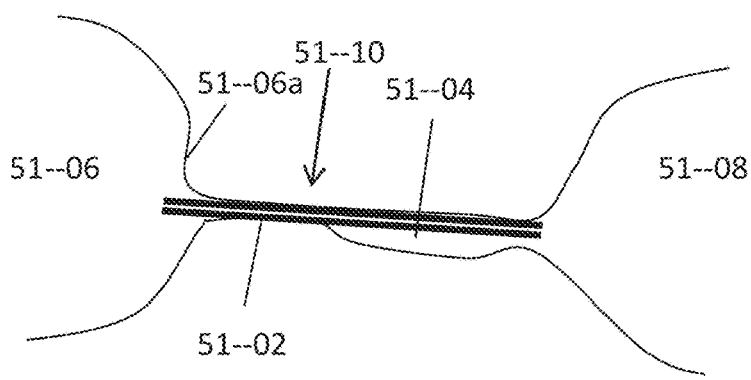
FIG. 51 is a simplified schematic side view of a non-conforming structure deployed within an ostium, according to some embodiments of the invention.

In some embodiments, one or more portion of the structure does not conform to the lumen, for example, at least a portion of the structure is expanded to a shape where the structure is smaller than the portion of the lumen surrounding that part of the structure. FIG. 51 is a simplified schematic side view of a non-conforming structure 5102 deployed within an ostium 5104, according to some embodiments of the invention. Structure 5102 could also be considered to conform along a portion of the structure length as a portion of the structure within narrowing 5110 is of similar geometry to the lumen in that area.

In some embodiments, different portions of a structure conform by different extents. For example, in some embodiments a portion of a structure is expanded to a larger geometry than the lumen geometry at that point to anchor the structure to the lumen.

In some embodiments, a structure is deployed to match a temporarily narrowed (e.g. due to swelling) lumen geometry and, for example, after a time period (e.g. for healing in which the lumen expands) the structure then falls out and/or is easily removed.

Figure 52:
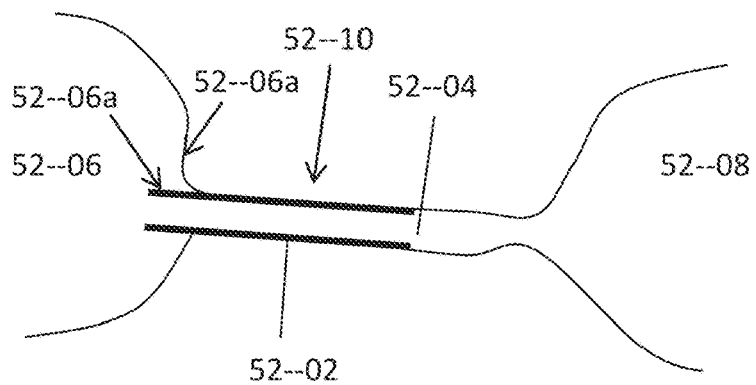
FIG. 52 is a simplified schematic cross sectional view of an ostium with an expanded structure widening an ostium narrowing, according to some embodiments of the invention.

In some embodiments, the structure changes a geometry of the ostium, e.g. widening the ostium at one or more points. In this case, the expanded structure conforms to the lumen after treatment, however, the expanded structure does not conform to the lumen geometry prior to treatment. FIG. 52 is a simplified schematic cross sectional view of an ostium 5204 with an expanded structure 5202 widening an ostium narrowing 5210, according to some embodiments of the invention.

Figure 53:
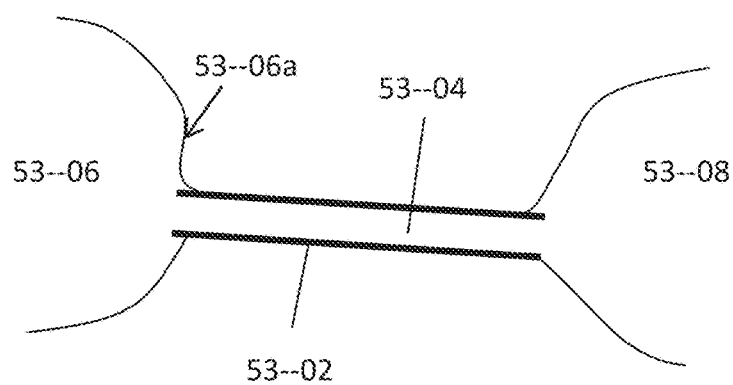
FIG. 53 is a simplified schematic cross sectional view of an expanded structure within an entire length of an ostium, where the structure changes a geometry of the ostium, according to some embodiments of the invention.

FIG. 53 is a simplified schematic cross sectional view of an expanded structure 5302 within an entire length of an ostium 5304, where the structure changes a geometry of the ostium, according to some embodiments of the invention.

In some embodiments, a single structure is deployed into more than one lumen. For example, in some embodiments, a portion of a structure extends out of one lumen into another lumen (e.g. the structure extends out of an ostium into a sinus) conforms and/or partially conforms to the geometry of the lumen.

Figure 54:
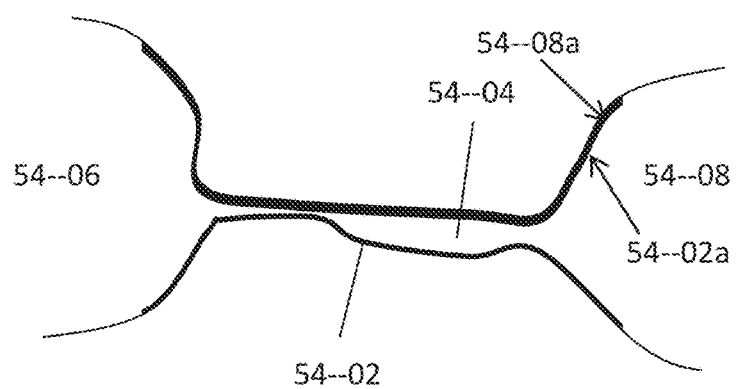
FIG. 54 is a simplified schematic cross sectional view of an expanded structure within an ostium, where the structure extends into a nasal cavity and a sinus, according to some embodiments of the invention.

In some embodiments, portions of a structure extending from the target lumen (e.g. ostium) conform to the lumens into which they extend. FIG. 54 is a simplified schematic cross sectional view of an expanded structure within an ostium 5404, where the structure extends into a nasal cavity 5408 and a sinus 5406, according to some embodiments of the invention. In some embodiments, a portion of structure 5402 which extends into nasal cavity 5408 conforms (e.g. is expanded to conform) to nasal cavity 5408. In some embodiments, a portion of structure 5402a which extends into sinus 5406 conforms (e.g. is expanded to conform) to sinus wall 5408a.

Figure 55:
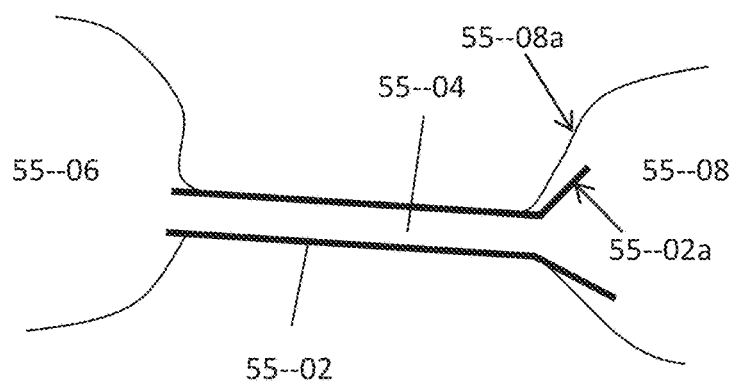
FIG. 55 is a simplified schematic cross sectional view of an expanded structure within an ostium, where a portion of the structure extending outside of the ostium partially conforms, according to some embodiments of the invention.

FIG. 55 is a simplified schematic cross sectional view of an expanded structure 5502 within an ostium 5504, where a portion of the structure extending outside of the ostium partially conforms, according to some embodiments of the invention. In some embodiments, a portion of a structure extending from a lumen (e.g. target lumen, desired lumen) into a second lumen partially conforms to the second lumen. For example, a portion 5502a of structure 5502 deployed within ostium 5504 extends into a nasal cavity 5508 and partially conforms to walls 5508a of the nasal cavity. In some embodiments, as illustrated by FIG. 55, structure 5502 widens the ostium. In some embodiments, the structure conforms and/or partially conforms to the ostium.

In some embodiments, one or portion of a structure conforms and one or more portion of the structure does not conform. For example, in some embodiments, a structure is deployed into an ostium and a portion of the structure extends out of the ostium does not conform (e.g. a portion of the structure extending into the sinus does not conform to the sinus walls).

Figure 56:
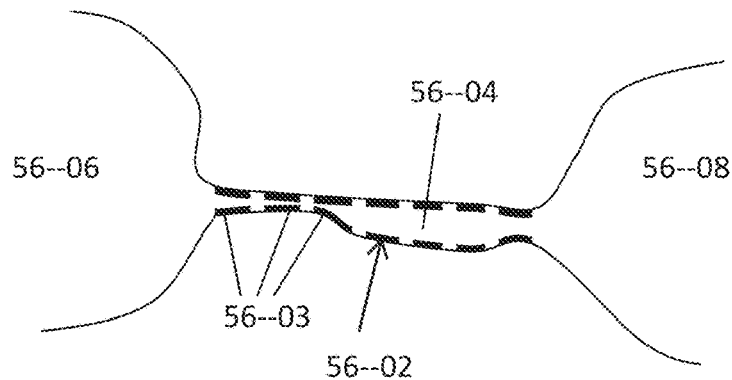
FIG. 56 is a simplified schematic cross section of a structure including segments expanded within a lumen, according to some embodiments of the invention.

In some embodiments, a structure including segments conforms to a lumen. FIG. 56 is a simplified schematic cross section of a structure 5602 including segments 5603, expanded within a lumen 5604, according to some embodiments of the invention. In some embodiments, different geometries and/or extents of conformation of the structure within the lumen are provided by a structure including segments, where different segments optionally have different characteristics (e.g. crimped geometry and/or materials).

In some embodiments, a structure with cross section which conforms or partially conforms to a lumen at one point contacts the lumen at several discrete points. For example, due to strut and/or mesh structure of the SM portion and/or the polymer portion. For example, at portions of a structure cross section perimeter which include SM material, as the SM material is pushing outwards and is restrained by the polymer portion which is further separated from lumen walls e.g. the structure has a cross sectional polygon shape where corners are defined by the SM portion.

In some embodiments, areas where the structure contacts the lumen are selected. For example, in some embodiments, a structure selected and/or is expanded to avoid contacting a wounded and/or inflamed region.

Medication

In some embodiments, a structure which includes medication is deployed into a lumen. For example, the structure is coated (e.g. coated in a drug eluting material and/or a drug containing media) and/or immersed in a medication before deployment. In some embodiments, the structure is coated and/or immersed in steroid medication (e.g. steroid gel, e.g. corticosteroid gel).

In some embodiments, a structure includes steroid medication, for example, one or more of: fluticasone propionate (e.g. cream 0.05% (15 g, 30 g, 60 g), e.g. 1% gel), Beclomethasone Diprolene (e.g. gel or 0.05% cream), Triamcinolone (e.g. Nasacort®), Flunisolide (e.g. Nasalide®), Budesonide (e.g. Rhinocort®), Ciclesonide (e.g. Omnaris®).

In some embodiments, a structure includes antibiotic medication, for example one or more of amoxicillin-clavulante (e.g. Augmentin®), Methicillin (e.g. Quinolone®), Trimethoprim-sulfamethoxazole, Clindamycin.

A potential benefit of combining medication with the stent is that medication is delivered locally to a desired target e.g. replacing or reducing the need for systemic medication. In some embodiments, medication relieves symptoms caused by the structure (e.g. allergic reaction to stent materials, inflammation due to pressure from structure). In some embodiments, a structure including steroid medication is used for local treatment of polyposis.

In an exemplary embodiment, the structure with steroid gel (e.g. mometasone fuorate gel) is deployed. In some embodiments, a structure includes many open spaces and/or open chambers (e.g. due to open or mesh-like structure of one or more than one portion of the structure) and medication. In some embodiments, medication on the structure is gradually absorbed into tissue. In some embodiments, medication is re-applied to the structure periodically e.g. in a doctor's office, during a periodic patient visit. A potential benefit of local delivery of medication to a lumen using a structure with medication loaded into structure open spaces is gradual and/or prolonged absorption of medication from the structure into surrounding tissue.

In some embodiments, the structure has a flared shape at one or more end of the structure, for example, as illustrated in FIGS. 54 and 55. Where the term flared corresponds to expanding cross section towards an end of the structure which refers to cross sectional perimeter length increasing and/or cross sectional area of a space enclosed by the perimeter of the structure increasing.

Number of Structures

In an exemplary embodiment, a single structure is deployed into each lumen. In some embodiments, more than one structure is deployed into a single lumen.

Duration of Treatment

In some embodiments, structure/s are left in position for a time duration sufficient for tissue to heal, for example sufficient time for post-operative healing, e.g. for up to 1 week, up to 4 weeks, up to 6 weeks, or shorter, or longer, or intermediate time periods.

In some embodiments, structure/s are left in position to change a geometry of a lumen (e.g. reduce nasal valve stenosis), for example, for 1-30 weeks, or 1-20 weeks, or 1-10 weeks or shorter or longer or intermediate time periods.

In some embodiments, structure/s are left in position to deliver medication to a lumen and/or surrounding tissue, for example, steroid medication, e.g. for up to two weeks, up to four weeks, up to six weeks, up to 10 weeks, up to 20 weeks or longer or shorter or intermediate time periods.

In some embodiments, for example in chronic rhinitis treatment, a structure is left in position and medication is re-applied to the structure and/or surrounding tissue periodically, for example, during periodic check-ups (e.g. once a month).

Imaging

In some embodiments, imaging is used to aid positioning and/or repositioning of structures for example, by providing visual feedback to a user operating a structure delivery system. In some embodiments, imaging is used to aid expanding of a structure to a desired geometry (e.g. matching a lumen) for example, by providing visual feedback of the structure and/or lumen to a user operating a structure delivery system.

In some embodiments, imaging is used to aid removal of structure/s e.g. without damaging patient tissue, for example, by providing visual feedback of the structure and/or lumen to a user operating a removal system.

In some embodiments, deployment systems and/or removal systems are inserted with an endoscope and optionally real-time images from the endoscope are used in delivery and/or expanding and/or removal and/or repositioning of a structure.

In some embodiments, one or more part of the structure and/or delivery system and/or removal system are radiopaque, for example, to provide visibility in CT and/or X-ray images.

In some embodiments, the structure and/or delivery system and/or retrieval systems are MRI compatible (e.g. do not contain ferromagnetic material).

Exemplary Method of Delivery and Deployment

FIG. 57 is a flow chart showing a method of delivery and deployment of a structure, according to some embodiments of the invention.

At 5702, a delivery system to which a structure (e.g. as described herein) is coupled is inserted into a patient. In some embodiments, the delivery system is inserted into the patient through a body lumen with an external opening e.g. nostril, urethra.

At 5704, the structure is positioned in a desired position (e.g. target) within a desired lumen using the delivery system. In some embodiments, a portion of the delivery system remaining outside of the patient's body is used to position the structure. For example, in an exemplary embodiment, an elongated delivery system is inserted into the patient's body through the nostril and the delivery system is then advanced (e.g. by pushing on a portion of the delivery system remaining outside the patient) to a nasal target. For example, the structure is advanced through the nostril to the middle meatus and through the middle meatus to a target position within an ostium.

In some embodiments, a structure is rotated during delivery, for example in order to position a non-symmetrical structure correctly. In some embodiments, a structure expands non-symmetrically, e.g. to a greater extent in dome directions than others and the structure is optionally rotated during delivery to position the structure in a correct rotational orientation in the lumen, e.g. as the balloon expanding the structure expands non-symmetrically (e.g. balloon is thicker on one side than another).

At 5706, the structure is decoupled from the delivery system. In an exemplary embodiment, the structure is decoupled by expanding the structure by inflating a delivery system balloon and then deflating the balloon to decouple the delivery system from the structure. In some embodiments, at least a portion of the structure is coupled (e.g. anchored e.g. by being expanded to conform to a lumen) to patient tissue more strongly than coupling of the structure to the delivery device, and moving the delivery system then decouples the delivery system and structure.

At 5708, the delivery system is removed e.g. by pulling on a portion of the delivery system remaining outside the patient's body.

In some embodiments, the delivery system includes an elongated element (e.g. shaft tube) and the system is advanced in the nasal cavity by pushing on the elongated element. In some embodiments, a portion of the elongated element remains outside the body.

In some embodiments, the structure is crimped onto a portion of the delivery system (e.g. balloon), where the crimped structure is coupled sufficiently strongly to the delivery system such that the crimped structure remains in a known position (e.g. an initial position) on the delivery system, for example, despite movement of the delivery system through the body (e.g. from the nostril to a desired position in an ostium). In some embodiments, coupling of the structure to the delivery system, where the delivery system includes a balloon, is by partial inflation of the balloon, after the structure has been crimped and/or placed onto the balloon.

In an exemplary embodiment, the structure is expanded by inflation of a balloon within the structure. Alternatively or additionally, in some embodiments, the structure is self expanding and/or expands upon a temperature change.

In some embodiments, a structure is expanded in a single stage. Alternatively, in some embodiments, a structure is expanded in multiple stages, optionally facilitating checking, for example, using imaging (e.g. endoscopy) of structure position and/or geometry.

In an exemplary embodiment, a balloon within the structure is expanded with fluid (e.g. water) by a syringe coupled to the balloon.

In some embodiments, the balloon is inflated (e.g. and structure expanded) by a single injection of fluid (e.g. single depression of a syringe plunger) into the balloon. In some embodiments, the balloon is inflated (e.g. and structure expanded) with multiple injections of fluid (e.g. multiple depressions of a syringe plunger).

In some embodiments, the balloon is then deflated by applying negative pressure using the syringe.

Imaging to Guide Delivery

In some embodiments, one or more type of imaging is used to guide delivery of the structure to a target position.

In some embodiments, an endoscope is inserted with the delivery system, for example, with a field of view (FOV) of the endoscope including the expandable structure. FIG. 58 is a simplified schematic side view of a delivery system 5800 guided by an endoscope 5832, according to some embodiments of the invention. In some embodiments endoscope 5832 includes an objective lens 5826, an illumination lens 5828 and an endoscope body 5824. In some embodiments, an expandable structure 5802 is mounted on a delivery system 5800 including a balloon 5810 (e.g. as described elsewhere in this document). In some embodiments, a field of view (FOV) 5830 of the endoscope provides a view of at least a portion of the structure and/or at least a portion of a target area (e.g. lumen, portion of a lumen) where the structure is to be deployed.

In some embodiments, the endoscope follows a same path within the patient as the delivery device. Alternatively, for example, to reduce trauma to patient tissue, in some embodiments, the endoscope follows a different path to the delivery device (e.g. the endoscope is inserted through a different nostril).

In some embodiments, an endoscope is part of a delivery system which optionally includes a retrieval and/or repositioning system (e.g. as described herein). In some embodiments, an endoscope is part of a retrieval system (e.g. as described herein). FIG. 59 is a simplified schematic side view of an endoscope delivery system 5900, according to some embodiments of the invention. In some embodiments, an expandable structure 5902 is delivered to a target by and/or through an endoscope body 5924. In some embodiments, endoscope 5932 includes an objective lens 5926 and one or more illumination lens 5928. In some embodiments, structure 5902 is mounted on a structure delivery system 5900a including a balloon 5910 (e.g. as described elsewhere in this document). In some embodiments, a field of view (FOV) 5930 of the endoscope provides a view of at least a portion of the structure and/or at least a portion of a target area (e.g. lumen, portion of a lumen) where structure 5902 is to be deployed. Optionally, in some embodiments, the balloon mounted structure is retractable into a lumen 5922 of an endoscope body 5922.

In some embodiments, ultrasound images are used in positioning of the device, for example, providing visual feedback to a user as to device positioning and/or expansion and/or conforming to lumen geometry. In some embodiments, CT and/or X-ray and/or MRI images are used to check positioning and/or deployment of the structure, for example, providing visual feedback to a user as to device positioning and/or expansion and/or conforming to lumen geometry.

In some embodiments, imaging is not used to position and/or deploy a structure. For example, in some embodiments a structure is positioned at an entrance to a lumen and then deployed into the lumen, optionally without imaging. For example, in some embodiments, a cone shaped structure is inserted into an ostium to a depth defined by the shape of the cone and the geometry of the ostium opening. The cone is then expanded within the ostium, optionally without imaging, e.g. to a depth into the ostium defined by the shape of the cone.

Deploying—Structure Shape

In some embodiments, a structure which is cylindrical in a crimped state is expanded to a cylindrical shape (e.g. with circular cross section). In some embodiments, the structure is non-cylindrical in crimped and/or expanded states, for example, the structure has oval cross section.

In some embodiments, a structure is expanded to a geometry which changes along a length of the structure. In some embodiments, this expanded geometry is achieved with a structure with a uniform crimped state cross section. Alternatively, in some embodiments, this expanded geometry is achieved with a structure with a crimped geometry which changes along the length of the structure. In some embodiments, more than one balloon is used to expand the structure, e.g. achieving an expanded structure geometry which changes along the length of the structure. In some embodiments, for example, to produce compliant and non-compliant portion of a structure a compliant and non-compliant balloon are used respectively.

In some embodiments, different portions of a structure are sequentially expanded, optionally, to different geometries, for example, by moving a balloon within the structure. In some embodiments, the balloon is inflated to a first extent in a first position, deflated, then moved to a second position, then re-inflated to a second extent which is optionally different to the first extent.

In some embodiments one or more portion of a structure is expanded (e.g. by inflating a balloon inside the structure) for a longer duration of time, e.g. to make wider or larger geometry portion/s.

Low Migration—Deployment and Structure

In some embodiments, a deployed structure (e.g. as described herein) has low migration, where once deployed the structure remains substantially in an initial position within a lumen.

In some embodiments, the structure is expanded to conform to geometry of patient anatomy, preventing migration.

In some embodiments, the structure is anchored and/or secured to patient tissue.

In some embodiments, the structure includes one or more hook and/or prong which secure the structure to tissue. In some embodiments, hooks and/or prongs implant into patient tissue. In some embodiments, the structure is secured to tissue by one or more stitch (e.g. absorbable suture).

In some embodiments, a portion of the structure is shaped to provide an anchor. In some embodiments, a portion of the structure is expanded within a lumen to a larger size than the lumen, the reactive force from the lumen holding the structure in position.

In some embodiments, a structure is anchored by one or more widened structure portion. For example, referring to FIGS. 54 and 55, where a structure is deployed within a lumen and extends outside the lumen, in some embodiments at least a part of the portion outside the lumen is widened. In some embodiments, a larger structure section (e.g. 5502a, 54-02a) prevents the structure from falling out and/or moving.

In some embodiments, the structure is expanded sufficiently that one or more portion of the device is implanted into patient tissue. In some embodiments the term 'implanted' is used to refer to a structure expanded to an extent that the structure is securely positioned within the lumen and will not migrate (e.g. the structure is expanded to one or more dimension which is larger than the lumen dimension, reactive force from the lumen holding the structure in place).

In some embodiments one or more portion of a structure is expanded (e.g. by inflating a balloon inside the structure) for a longer duration of time, e.g. to make wider or larger geometry portion/s which anchor the structure to the lumen.

Sheathing

In some embodiments, a structure (e.g. as described herein) is delivered sheathed to a target location (e.g. within a lumen). In some embodiments, sheathing the structure during delivery facilitates use of a structure with a non-smooth exterior without abrading and/or damaging tissue as the structure is delivered to a target.

Figure 60A:
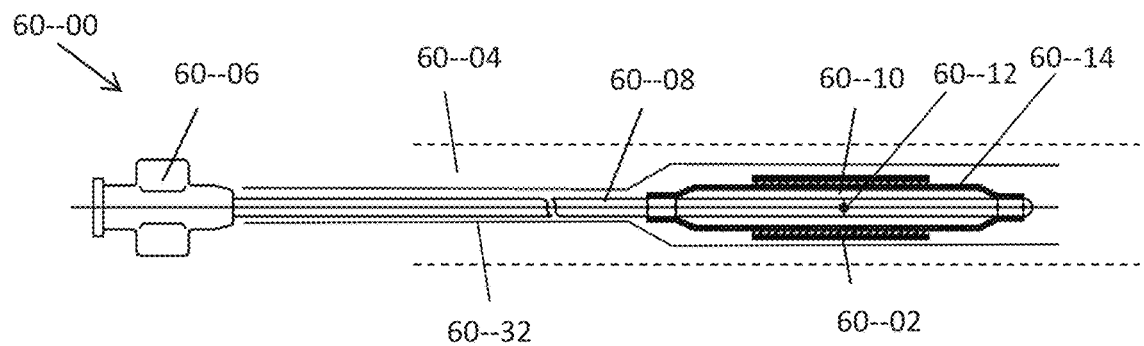
FIG. 60A is a simplified schematic cross section of a delivery device with a sheathed portion, according to some embodiments of the invention.
Figure 60B:
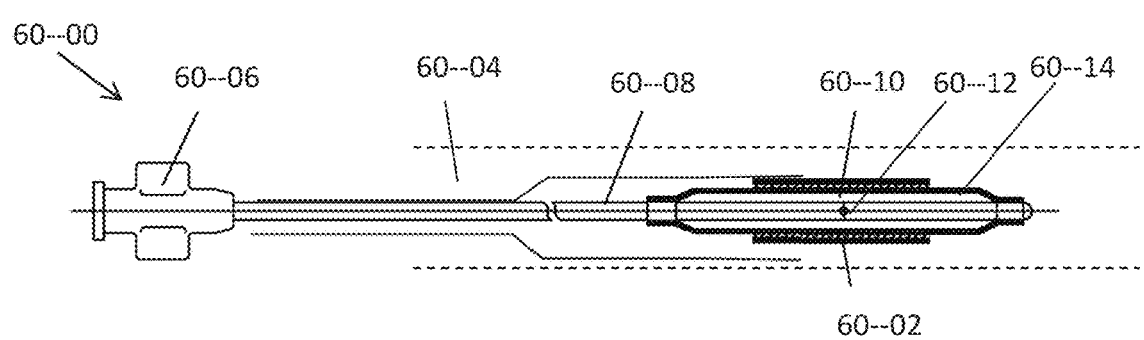
FIG. 60B is a simplified schematic cross section of a delivery device being unsheathed, according to some embodiments of the invention.

FIG. 60A is a simplified schematic cross section of a delivery system 6000 with a sheathed portion, according to some embodiments of the invention. FIG. 60B is a simplified schematic cross section of a delivery system being unsheathed, according to some embodiments of the invention. In some embodiments, an expandable structure 6002 at least partially surrounded by a sheath 6034 is delivered to a desired region (e.g. portion of a lumen 6004). Structure 6002 is then extended from sheath 6032 and/or sheath 6032 is retracted from structure 6002 before deployment (e.g. expanding) the structure.

For example, in some embodiments, the structure is delivered within an endoscope. Referring back to FIG. 59, in some embodiments, structure delivery system 5900a is in a retracted position within endoscope lumen 5922 during insertion of endoscope delivery system 5900, until a portion of system 5900 is close to a desired target area for the structure. Then, in some embodiments, structure delivery system 5900a is extended before deploying structure 5902.

Deployment System

Figure 61A:
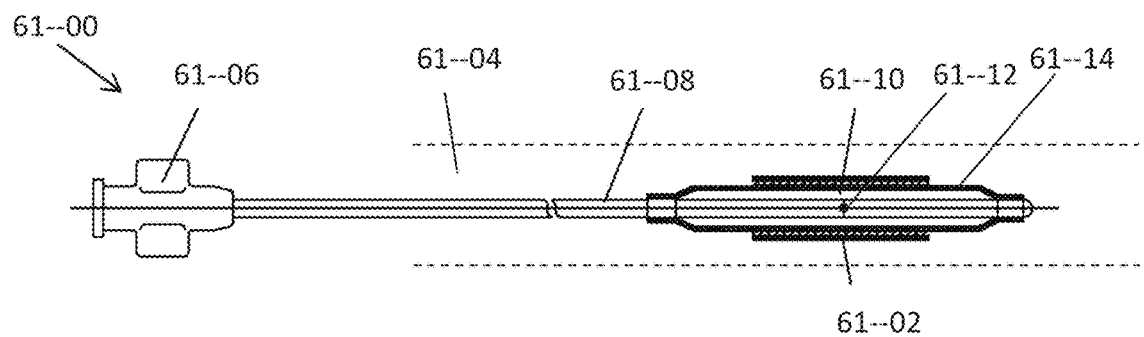
FIG. 61A is a simplified schematic cross sectional view of a delivery system delivering an expandable structure to a desired position within a lumen, according to some embodiments of the invention.
Figure 61B:
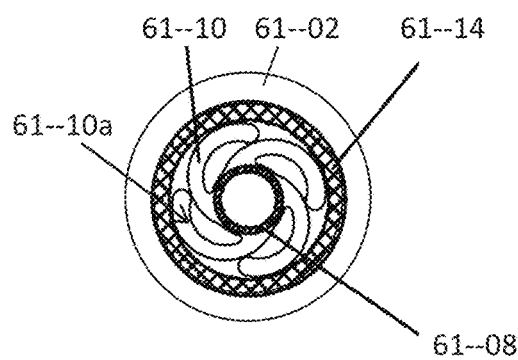
FIG. 61B is a simplified schematic cross sectional view of a delivery system delivering coupled to an expandable structure, according to some embodiments of the invention.

FIGS. 61A and 61B illustrate deployment of an expandable structure, by a delivery system, according to some embodiments of the invention.

FIG. 61A is a simplified schematic cross sectional view of a delivery system 6100 delivering an expandable structure 6102 to a desired position within a lumen 6104, according to some embodiments of the invention. FIG. 61B is a simplified schematic cross sectional view of a delivery system 6100 coupled to an expandable structure 6102, according to some embodiments of the invention. FIG. 61B illustrates a cross section perpendicular to the cross section illustrated in FIG. 61A.

In some embodiments, delivery system 6100 includes a hub 6106 through which a shaft tube 6108 is inserted into lumen 6104. In some embodiments, hub 6106 is located externally to the patient's body.

In some embodiments, delivery system 6100 includes a balloon 6110 which, in FIG. 61A and FIG. 61B is folded (not inflated). In some embodiments, balloon 61-10 folds into several petals 6110a around shaft tube. In some embodiments, petals 6110a overlap. In some embodiments, expandable structure 6102 is mounted onto balloon 6110. In some embodiments, balloon 6110 is inflated by introduction of pressurized fluid (e.g. liquid and/or gas) through shaft tube 6108 and through an outlet 6112 in shaft tube 6108 into the balloon. Inflation of balloon 6110 expands expandable structure 6110. In an exemplary embodiment balloon 6110 is inflated by introduction of liquid (e.g. water, saline).

In some embodiments, balloon 6110 includes markers, for example to visually assist (e.g. through an endoscopic view) a user to position the structure and/or expand the balloon to a desired geometry. In some embodiments, a structure is placed or mounted onto a balloon portion of a delivery system which has markers at known separations (e.g. along a balloon length). When the structure is deployed, a user, in some embodiments views images of markers (e.g. using CT/x-ray for example, if markers are radiopaque and stent is not) to position the structure and/or ascertain a position of the structure.

In some embodiments, an elastic element 6114 (e.g. an elastic tube or sheath) is located between expandable structure 6102 and balloon 6110, e.g. balloon 6110 is within elastic structure 6114 and elastic tube 6114 is within expandable structure 6102. In some embodiments, elastic element 6114 expands with balloon inflation, elastically retracting after a pressure of introduced fluid into the balloon is reduced.

In some embodiments, balloon 6110 is a low compliance balloon and elastic tube 6114 transforms balloon 6110 into a high compliance balloon, potentially enabling expansion of the balloon and structure to a geometry conforming to lumen 6104 geometry. A high compliance balloon also, potentially, exerts low pressure on surrounding tissue (e.g. lumen 6104 walls) when the balloon is inflated.

In an exemplary embodiment, balloon 6110 is expanded with fluid (e.g. water) introduced through shaft tube 6108 by a syringe coupled to shaft tube 6108. Balloon 6110, in some embodiments, is then deflated by applying negative pressure using the syringe.

Figure 62:
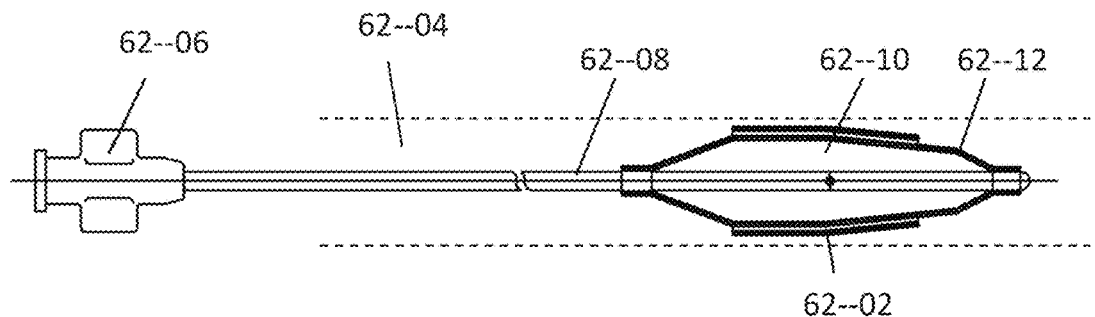
FIG. 62 is a simplified schematic cross sectional view of a delivery system deploying an expandable structure, where the expandable structure is partially expanded, according to some embodiments of the invention.

FIG. 62 is a simplified schematic cross sectional view of a delivery system 6200 deploying an expandable structure 6202, where the expandable structure is partially expanded, according to some embodiments of the invention. FIG. 62 illustrates partial expansion of an expandable structure 6202, where the structure is not lodged into position within a lumen 6204.

Figure 63A:
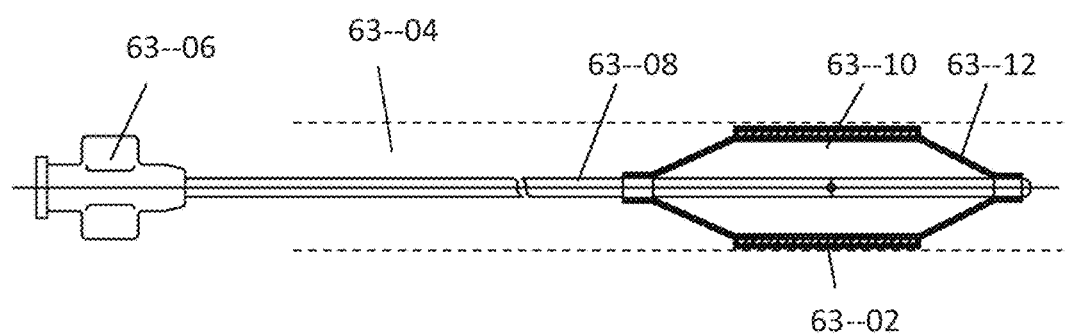
FIGS. 63A-B is a simplified schematic cross sectional view of a delivery system and an expanded structure, according to some embodiments of the invention.
Figure 63B:
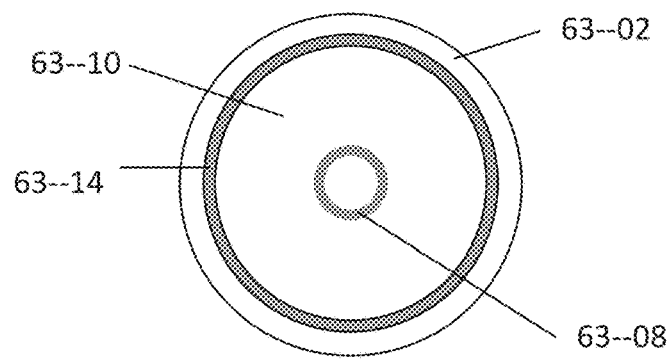

FIGS. 63A-B are a simplified schematic cross sectional view of a delivery system 6300 and an expanded structure 6302, according to some embodiments of the invention. FIGS. 63A-B illustrate an expandable structure 6302 which has been expanded to fill a portion of lumen 6304 (at least in the illustrated direction), e.g. conforming or partially conforming to a geometry of the lumen.

Figure 64:
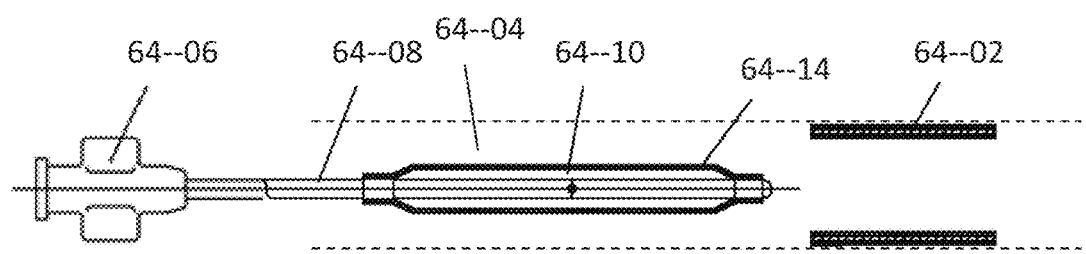
FIG. 64 is a simplified schematic of an expandable structure expanded within a lumen and a delivery system being removed from a lumen, according to some embodiments of the invention.

FIG. 64 is a simplified schematic of an expandable structure 6402 expanded within a lumen and a delivery system 6400 being removed from a lumen 6404, according to some embodiments of the invention.

In some embodiments, a deployment system is designed to produce varying geometry along a long axis (length) and/or along a bent long axis of the structure. For example, in some embodiments, the deployment system includes a compliant balloon and/or more than one type of balloon, and/or more than one balloon. For example, in some embodiments, cross-sectional shape of the expanded structure has different shaped cross section (e.g. circular and non-circular) along a structure long axis. In some embodiments, a structure is segmented and different segments are expanded to different geometries. In some embodiments, varying structure geometry enables the stent to conform to intranasal and intrameatal anatomy.

In some embodiments, varying geometry along structure length is achieved using a segmented structure where segments have different properties, e.g. crimped geometry, materials. In some embodiments, segments are connected by flexible and/or expandable and/or twistable connectors which allow adjacent segments to be expanded to different geometries.

Removal, Re-Positioning

In some embodiments, an expanded structure is removed from a first position within a lumen and then removed from the body. In some embodiments, an expanded structure is removed from a first position within a lumen and re-deployed in a new position within the same lumen (or a different lumen), for example, upon checking the structure position (e.g. using imaging) indicating that the structure is not in a desired position.

Method of Removal

FIG. 65 is a flow chart of a method of structure removal, according to some embodiments of the invention.

At 6502, a removal system is positioned. In some embodiments, a portion of the removal system is positioned in close proximity to a structure to be removed, for example, inserted into a lumen in which the structure is deployed. In some embodiments, a portion of the removal system is positioned inside the structure. In some embodiments, an outlet of the removal system (e.g. through which fluid is dispensed) is positioned sufficiently close to the structure such that fluid dispensed through the outlet contacts and/or flows over the structure.

At 6504 the structure is optionally collapsed onto a portion of the removal system. In some embodiments, the structure collapses upon a change of temperature. In some embodiments, the removal system effects a structure change of temperature (e.g. causing the structure to collapse e.g. self-crimp), for example, by flushing the structure with fluid (e.g. saline solution) cooled (e.g. to 5-10° C.) or heated above or below the temperature of the structure (e.g. body temperature).

Alternatively or additionally, in some embodiments, the structure is collapsed by expanding the structure above a threshold size.

At 6506 the removal system is withdrawn, removing the structure. In some embodiments, the structure collapsed onto a portion of the removal system tightly fits the removal system (e.g. in some embodiments, a removal system balloon is partially inflated within the crimped structure to secure the structure to the removal system) so that, when the removal system is withdrawn (e.g. from the body) the structure is removed. Alternatively or additionally, the removal system includes one or more hook and/or stopper and/or other coupling element/s, such that the structure is removed when the removal system is withdrawn.

Removal System

Figure 67:
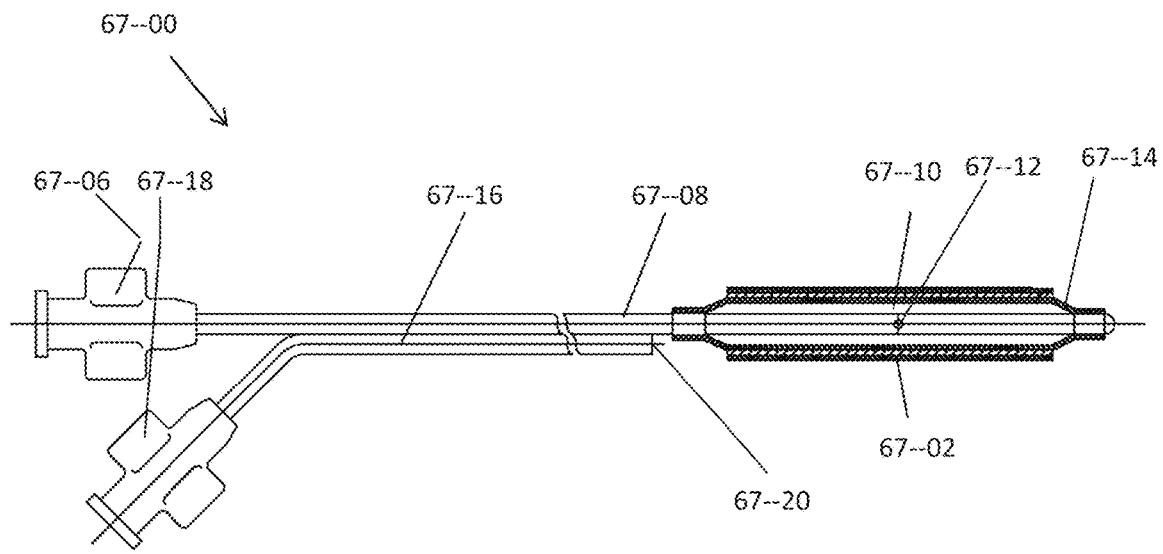
FIG. 67 is a simplified schematic cross sectional view of a combined deployment and removal system, according to some embodiments of the invention.
Figure 68:
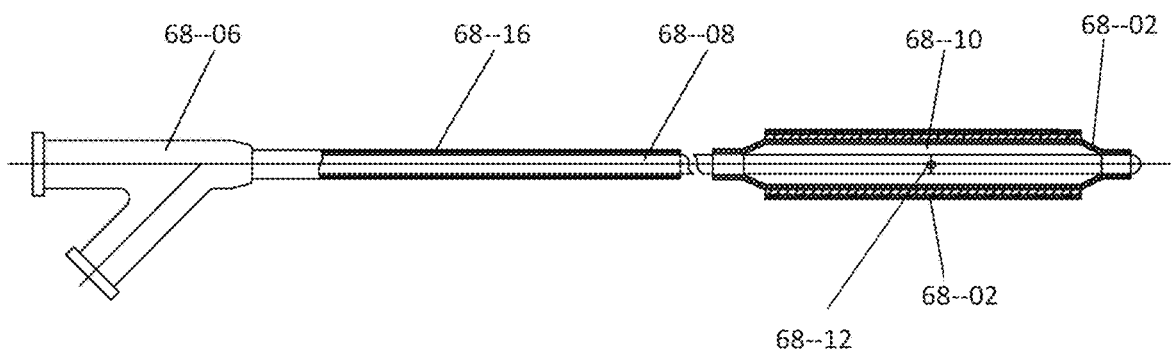
FIG. 68 is a simplified schematic of a combined delivery and retrieval system, with nested tubes, according to some embodiments of the invention.

FIGS. 66, 67 and 68 illustrate removal systems, according to some embodiments of the invention.

FIG. 66 is a simplified schematic cross sectional view of a removal system 6600, according to some embodiments of the invention. In some embodiments, removal system 6600 includes a tube 6616 which is inserted into the body through a hub 6618. In some embodiments, tube 6616 includes an outlet 6606. To remove a structure, tube 6602 is positioned inside the structure with outlet 6620 close enough to the structure that fluid discharged through outlet 6620 contacts the structure. Cooled or heated fluid is discharged through outlet 6620 causing the structure to collapse onto tube 6616. The structure is then removed by withdrawing tube 6616 through hub 6618. In some embodiments, tube 6620 is sized such that a crimped structure securely fits onto the tube.

Combined Delivery and Retrieval System

In some embodiments, for example, so that an expandable structure can be repositioned after being expanded, a combined delivery and removal system is used.

FIG. 67 is a simplified schematic cross sectional view of a combined deployment and removal system 6700, according to some embodiments of the invention. In some embodiments, system 6700 includes a delivery system similar to that illustrated in FIGS. 61A-B, for example, including a balloon 6710 nested inside an elastic element 6714 for deploying an expandable structure 6702, and including a hub 6706 and a shaft tube 6708.

In some embodiments, after structure 6702 is collapsed onto balloon 6710, balloon 6710 is partially inflated to tightly hold structure 6702. Optionally, in some embodiments, system 6702 and/or system 6802 (described below) is only a removal system and is not used for deployment of structures.

System 6700 also includes a second hub 6718 and a tube 6716 including an outlet 6720 through which fluid is dispensed to collapse expandable structure 6702 back onto elastic element 6714 and balloon 6710. Expandable structure 6702 is then either delivered to another desired position and re-expanded or is removed by withdrawing the shaft tube 6708 (to which the expanded structure is attached) from the lumen and/or body.

In some embodiments, a channel for inflation of a balloon and a channel for dispensing fluid to the structure are nested one within the other. FIG. 68 is a simplified schematic of a combined delivery and retrieval system 6800, with nested tubes, according to some embodiments of the invention. System 6800 includes a balloon 6810 nested inside an elastic element 6814 for deploying an expandable structure 6802. In some embodiments a shaft tube 6808 through which a balloon 6810 is inflated is located within a tube 6816 for dispensing fluid (e.g. temperature change fluid for collapsing the structure). Alternatively, in some embodiments, a tube for temperature change fluid is located within a tube for inflating the balloon.

Exemplary Treatments

An exemplary method of treatment of nasal and sinus disorders includes deploying a stent inside a surgically enlarged ethmoid sinus cavity, following endoscopic sinus surgery (e.g. after ethmoidectomy), to prevent formation of adhesions between raw surfaces in the nose, and within the middle meatus, where the stent is left in position for up to four weeks.

An exemplary method of treatment of nasal and sinus disorders includes deploying a stent inside a nasal valve to treat congenital and/or post-surgical nasal valve stenosis potentially improve breathing, where the stent is left in position for 1-10 weeks.

An exemplary method of treatment of nasal and sinus disorders includes deploying a stent inside a nasal cavity, between an inferior turbinate and the septum, to treat rhinitis (e.g. allergic rhinitis, non-allergic rhinitis) by providing patency in the inferior turbinate. In some embodiments, especially the stent/s are deployed prior to and/or after and/or to replace turbinectomy. In some embodiments, the stent/s are left in position for up to 24 weeks.

An exemplary method of treatment of nasal and sinus disorders accompanied by inflammation and/or polyposis includes positioning a stent soaked in steroid gel inside the intranasal cavity, between septum and lateral nasal cavity, to provide local steroid drug release in a controlled fashion, for a prolonged period of time (e.g. from 2 and up to 12 weeks) following stent implantation. Potentially, local release of steroids from the stent reduces inflammation and/or polyposis.

Exemplary Stents

In some embodiments, stents suitable for deployment in sinus ostia are approximately 15-30 mm long and have diameter of 3-5 mm before expansion and have diameter of 5-12 mm after expansion.

In some embodiments, stents suitable for deployment in the nasal cavity (e.g. between a turbinate and the septum) are 20-100 mm long and have diameter of 4-6 mm before expansion and have diameter of 7-14 mm after expansion.

In some embodiments, stents suitable for deployment in the nasal valve (e.g. to treat and/or prevent nasal valve stenosis) are 15-100 mm long and have diameter of 3-6 mm before expansion and have diameter of 5-14 mm after expansion.

In some embodiments, stents suitable for deployment in blood vessels are approximately 10-150 mm long and have deployed diameter of 4-12 mm.

In some embodiments, stents suitable for deployment in fallopian tubes are approximately 3-15 mm long and have deployed diameter of 1-2.

In some embodiments, stents suitable for deployment in the biliary system (e.g. in a biliary duct) are approximately 20-100 mm long and have deployed diameter of 5-10 mm.

In some embodiments, stents suitable for deployment in the nasal cavity are 0.1-1 mm thick, or 0.3-0.5 mm thick, or smaller, or larger, or intermediate thicknesses. In some embodiments, stents with larger crimped and/or deployed diameter are thicker than those with smaller crimped and/or deployed diameter.

Deployment into the Urethra

In some embodiments, stents suitable for deployment in the urethra are approximately 5-70 mm long and have deployed diameter of 5-20 mm.

In an exemplary embodiment, a structure is deployed into the urethra, for example, after prostate surgery, potentially holding the urethra open allowing urination despite post-operative swelling and/or trauma.

Figure 69A:
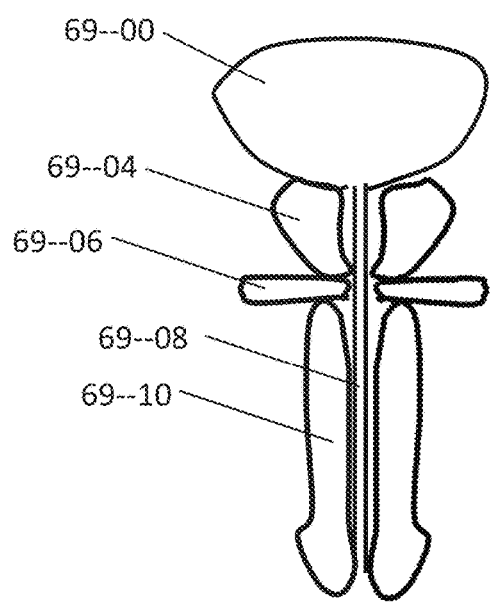
FIG. 69A is a simplified schematic cross sectional view of a portion of a male anatomy, before removal of a prostate.
Figure 69B:
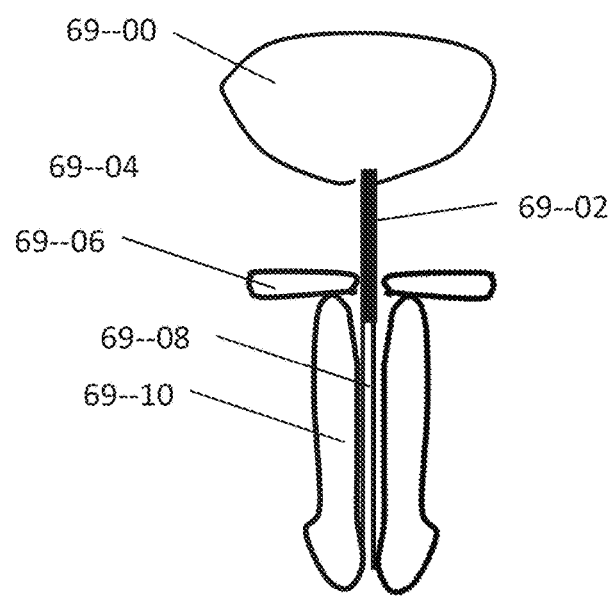
FIG. 69B is a simplified schematic cross sectional view of a male anatomy, after prostrate removal where an expandable structure has been deployed connecting a urethra to a bladder, according to some embodiments of the invention.

FIG. 69A is a simplified schematic cross sectional view of a portion of a male anatomy, before removal of a prostate 6900. FIG. 69B is a simplified schematic cross sectional view of a male anatomy, after prostrate removal, where an expandable structure 6902 has been deployed connecting a urethra 69-08 to a bladder 69-00, according to some embodiments of the invention.

FIG. 69A and FIG. 69B also show a pelvic floor 6906, and a penis 6910. FIG. 69A shows a prostate 6904 which is absent in FIG. 69B due to prostate removal surgery.

In some embodiments, one or more expandable structure 6902 is deployed, as illustrated in FIG. 69B, at the region of the urethra, adjacent to the prostate (prior to prostate removal). Alternatively, in some embodiments, structure/s are deployed along the length of the urethra, for example, acting as an implanted catheter. In some embodiments, one or more structure is deployed in bladder 6900.

In some embodiments, the polymer portion is formed from medical grade polymer, for example, from biomedical polyurethane (e.g. Bionate®) and/or polycarbonate-based thermoplastic polyurethane (e.g. Carbothane®) and/or polycarbonate based urethane (e.g. Chronoflex®) and/or aliphatic polyether-based thermoplastic polyurethane (e.g. Tecoflex™).

Figure 72:
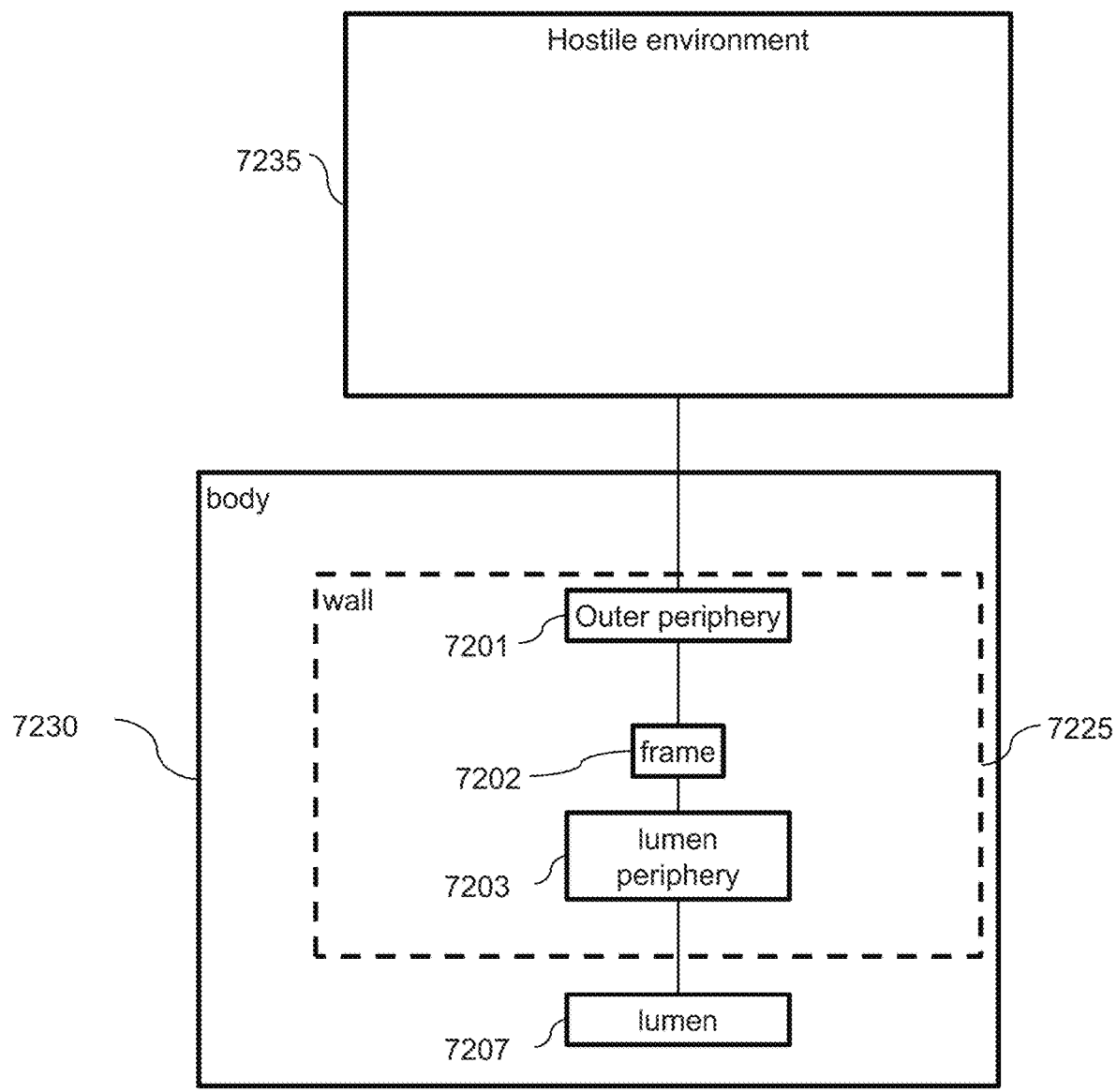
FIG. 72 is a block diagram illustration of a composite elastic body, in accordance with some embodiments of the invention.

FIG. 72 is a block diagram illustration of a composite elastic body in accordance with some embodiments of the current invention. In some embodiments an elastic body 7230 may be placed in contact with a hostile environment 7235. Optionally the body 7230 includes a lumen 7207 and/or a hollow surrounded by a wall 7225. Optionally wall 7225 has a non-uniform cross section. For example, wall 7225 has an outer peripheral layer 7201 in contact with an external environment 7235 and an inner peripheral layer 7203 in contact with lumen 7207. Optionally peripheral layers 7201 and 7203 are flexible and/or elastic. Optionally peripheral layer 7201 that is contact with hostile environment 7235 is configured to be durable under the hostile conditions. Optionally body 7230 may have an elastic frame 7202 that has desired mechanical properties. For example, the frame 7202 may include a polymer layer and/or strands and/or mesh sandwiched between two peripheral layers. Alternatively or additionally, frame 7202 may be covered on one side by a peripheral layer 7201 and may be exposed on another side.

In some embodiments, composite elastic body 7230 may be a second elastic and/or polymer portion of an expanding structure. For example, the expanding structure may be a structure as described in any of the embodiments of an expanding structure described herein. For example the expanding structure may have multiple stable states. For example the expanding structure may be a stent.

Examples of hostile environments may include inside a human body, for example a nasal cavity.

Figure 73:
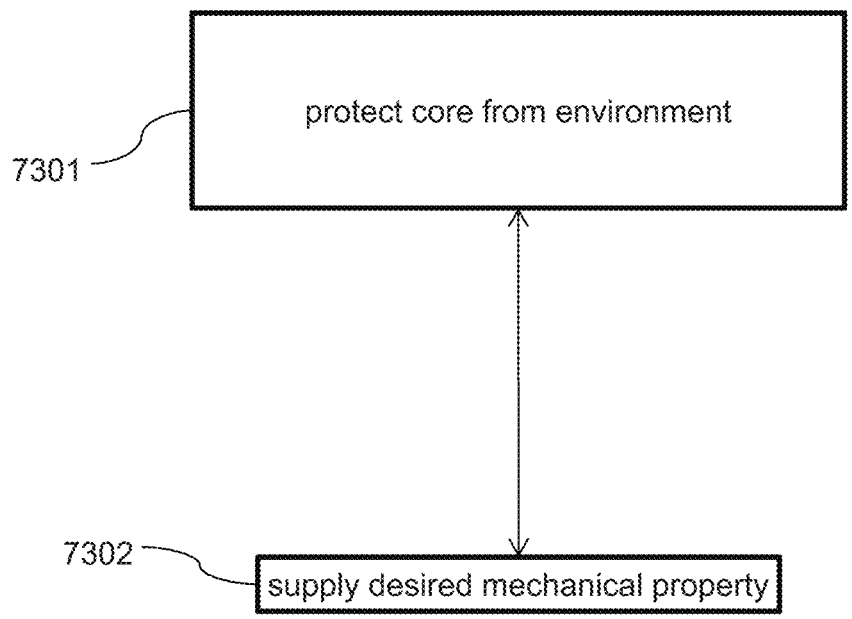
FIG. 73 is a flow chart illustration of a composite elastic body, in accordance with some embodiments of the invention.

FIG. 73 is a flow chart illustration of a method of supplying composite elastic body in accordance with some embodiments of the current invention. For example, the body may have a durable fraction that protects 7301 a frame from a hostile environment. Optionally a frame portion of the body supplies 7302 desired mechanical properties. The durable portion may be biocompatible for example in resisting degradation inside a human body and/or in not stimulating damaging reactions in a human when inserted into his body. For example, a peripheral layer of the body may be configured specifically for a particular body local for example a nasal cavity, a blood vessel, a digestive organ and/or a urethra. The frame and durable fraction may be compatible. For example, the frame and peripheral layer may have similar stretchability so that they stretch together without damage. For example, the frame and peripheral layer may be made of materials that adhere one to the other, For example, frame and the peripheral layer may be made of materials with similar melting points and/or other properties making them suited for coextrusion. For example the frame and peripheral layer fraction may have compatible flexibility (for example they will flex together without cracking).

Figure 74A:
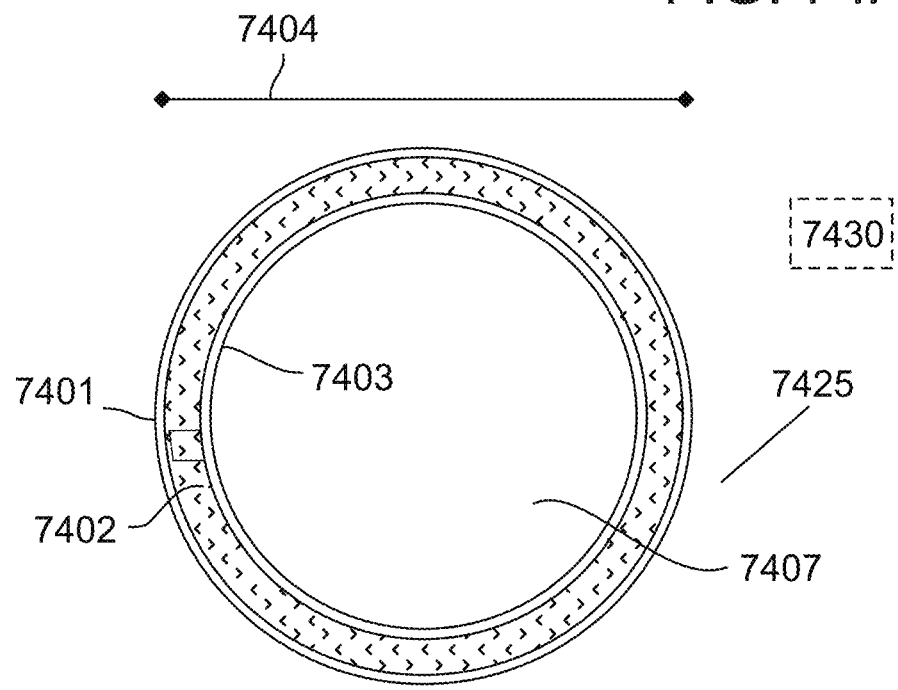
FIG. 74A-B is cross sectional illustration of a composite elastic tubular body, in accordance with some embodiments of the invention.
Figure 74B:
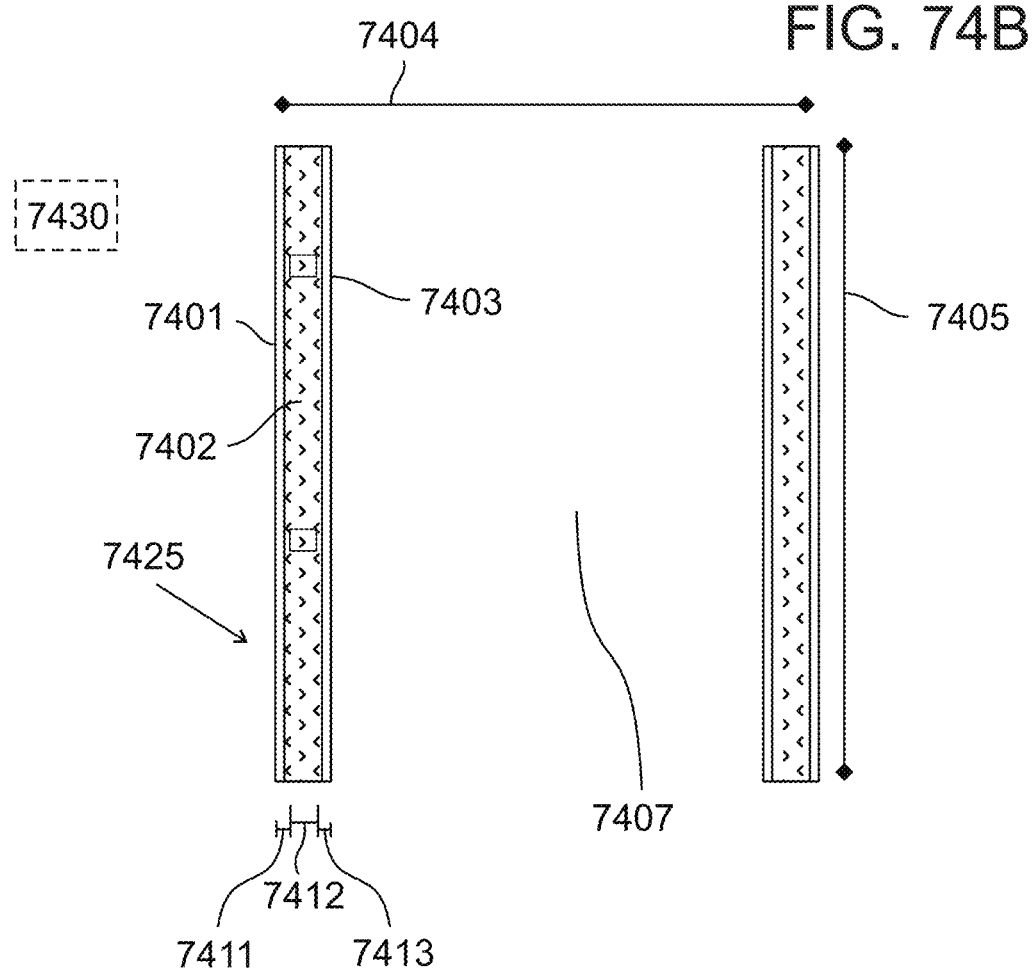

FIG. 74A-B is cross sectional illustrations of a composite tubular elastic body in an unstressed state in accordance with some embodiments of the current invention. In some embodiments the body includes a frame and one or more peripheral layers. Optionally, the peripheral layers may protect the frame from an external environment (for example external to the tube) and/or an internal environment (for example in the lumen of the tube). For example the tube may be a elastic and/or polymer and/or an external part of a nasal stent.

In some embodiments, a composite elastic body 7430 may have the form of a tube of circular and/or non-circular cross section. Optionally a wall 7425 of the tube have a composite body including a frame 7402 and/or one or more peripheral layers for example an outer peripheral layer 7401 and/or an inner peripheral layer 7403. For example outer peripheral layer 7401 may protect frame 7402 from an external environment. For example inner peripheral layer 7403 may protect frame 7402 from an internal environment, for example in the tube lumen 7407. The length 7405 of the body 7430 may depend on the application. For example the length 7405 may be the length of a stent as described for example in various embodiments herein.

In some embodiments, an outer diameter 7404 and/or width of the unstressed tube may range between 0.1 to 0.5 mm and/or between 0.5 to 2 mm and/or between 2 to 4 mm and/or between 4 to 12 mm and/or between 12 and 50 mm. The thickness 7412 of frame 7402 may for example range between 20 to 150 μm. The thickness 7411 of outer peripheral layer 7401 may range for example between 10 to 100 μm. In some embodiments, the thickness of the peripheral layer may by enough to prevent movement of harmful molecules and or ions (that may damage the frame) through the peripheral layer to the frame. For example such movement may include diffusion and/or passage through cracks and/or fissures and/or micro cracks. Optionally, In some embodiments, the peripheral layer more than 15 µm preventing diffusion of molecules that may damage the frame The thickness 7413 of the inner peripheral layer 7403 may range for example between 10 to 100 µm. Alternatively or additionally the body may gradually change across its cross section between the periphery and frame. Optionally one or more of the peripheral sections may not form a discrete layer. Alternately or additionally, a composite tube may include a frame and an outer peripheral layer without an inner peripheral layer. Alternately or additionally, a composite tube may include a frame and an inner peripheral layer without an outer peripheral layer.

Figure 75A:
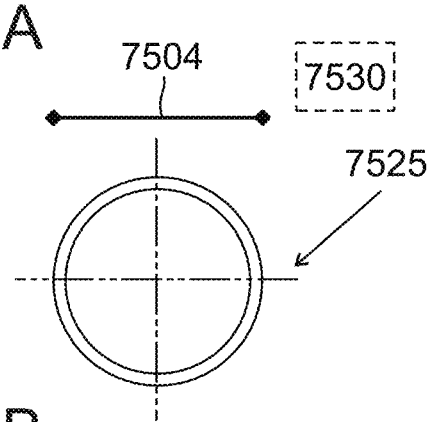
FIG. 75A-B are cross section and a cutaway illustrations of a composite elastic body 7530 in accordance with some embodiments of the current invention.
Figure 75B:
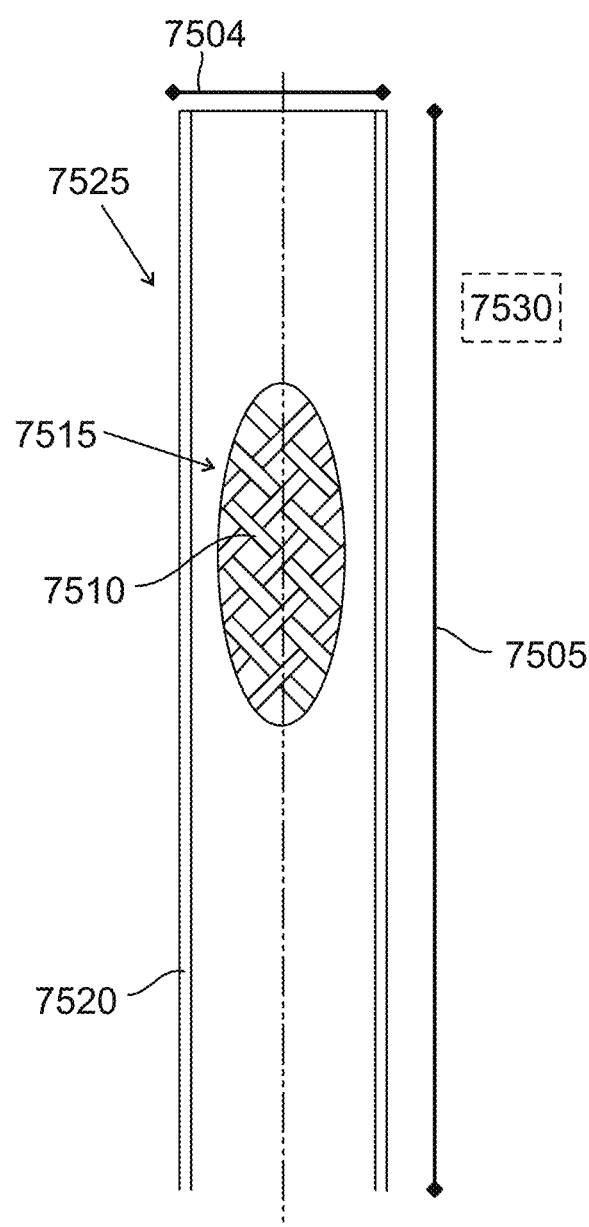

FIG. 75A-B are cross section and a cutaway illustrations of a composite elastic body 7530 in accordance with some embodiments of the current invention. In some embodiments body 7530 may be at least partially formed of composite filaments 7510.

Figure 75C:
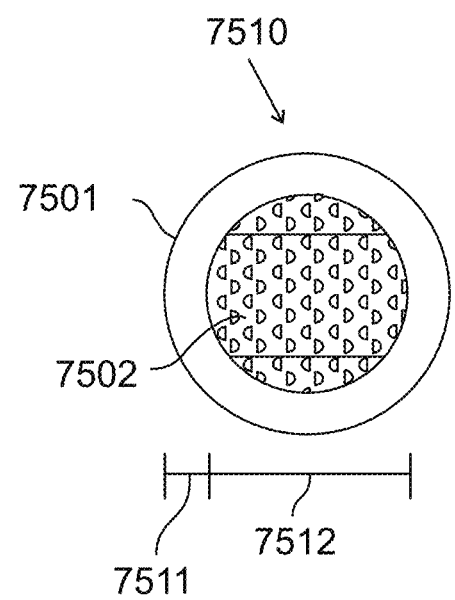
FIG. 75C is a cross sectional illustration of a composite filament in accordance with some embodiments of the current invention.

FIG. 75C is a cross sectional illustration of a composite filament in accordance with some embodiments of the current invention. In some embodiments a filament 7510 optionally had a composite cross section, for example including a frame for example core 7502 and one or more peripheral layers 7501. Optionally, peripheral layer 7501 may protect core 7502 from an external environment. For example, one or more peripheral layers 7501 may form one or more rings around core 7502. For example elastic body 7530 may include of one or more filaments 7510 wound and/or woven and/or formed into a mesh 7515 and/or a lattice. Optionally there may be simple filaments and/or composite filaments 7510. Optionally elastic body 7530 may form an elastic portion and/or covering of a stent as described in any of the embodiments herein. For example a stent may be used in a nasal cavity.

In some embodiments, a composite elastic body 7530 may have the form of a tube of circular and/or non-circular cross section. Optionally a wall 7525 of the tube include filaments of composite body including a core 7502 and/or one or more peripheral layers for example an outer peripheral layer 7501. For example outer peripheral layer 7501 may protect core 7502 from an external environment.

In some embodiments, an outer diameter 7504 and/or width of the unstressed tube may range between 0.1 to 0.5 mm and/or between 0.5 to 2 mm and/or between 2 to 4 mm and/or between 4 to 12 mm and/or between 12 and 50 mm. The thickness 7512 of core 7502 may for example range between 20 to 150 µm. The thickness of the walls of the tube may range for example between 20 to 500 µm. The length 7505 of the body 7530 may depend on the application. For example the length may be the length of a stent as described for example in various embodiments herein.

In some embodiments, the thickness 7511 of outer peripheral layer 7501 of a filament may range for example between 1 to 10 µm and/or 10 to 30 µm and/or 30 to 60 µm and/or 60 to 100 µm. The thickness 7512 of the core 7502 may range for example between 1 to 15 µm and/or 15 to 40 µm and/or 40 to 80 µm and/or 80 to 200 µm and/or 20 to 1000 µm. Alternatively or additionally the body may gradually change across its cross section between the periphery and core. Optionally one or more of the peripheral sections may not form a discrete layer.

Some exemplary compositions for various layers of a composite body and/or filament are listed in the table 1.

| part | frame | periphery |
|---|---|---|
| Exemplary Component label | 7402, 7502 | 7401, 7403, 7501 |
| | Tecoflex (e.g. EG80A) | Chronoflex (e.g. AL80A) |
| | Tecothane | Carbothane |
| | Carbothane | Carbothane |
| | 3585 aliphatic TPU | 3585 B20 aliphatic TPU |

Table 1—example materials for the majority compositions of the frame 7402 and 7502 fraction and/or the peripheral fraction 7401, 7403, 7501 of composite elastic structures.

Additional Exemplary Embodiment

In some embodiments a structure includes a polymer (e.g. polyurethane) portion, for example, a tubular polymer portion which, when expanded for longer than a minimal expansion time period, substantially maintains an expanded geometry.

In some embodiments, one or more portion of the structure only comprises polymer. In an exemplary embodiment, the structure comprises only polymer. In some embodiments, the structure comprises SM material.

In some embodiments, the structure is elastic radially, at body temperature, when expanded for a short time, (e.g. less time than the minimum expansion time period). In some embodiments, the structure elastically returns to a crimped state when expanded for 1-2 minutes or 1-5 minutes or 1-10 minutes. A potential benefit of which is ease of repositioning the structure; at expansion times less than the minimum expansion time period the structure self collapses (e.g. onto a delivery device facilitating repositioning) when the expanding pressure (e.g. pressure applied by a balloon inflated within the structure) is reduced. A further benefit is the ability to inflate the structure to a geometry which conforms to a lumen, with a non-compliant balloon (e.g. similar to the delivery system elastic element, as described herein).

In some embodiments, the minimum expansion time period is reduced by elevating a temperature of the structure, optionally for temperatures up to 40° C.

In some embodiments, the minimum expansion time period is approximately 30 minutes. In some embodiments, the minimum time period is 10-60 mins, or 20-45 mins or 25-35 mins. In some embodiments, when the structure is deployed within a lumen, the structure is expanded for up to 24 hours.

In some embodiments, a change in temperature (e.g. an increase in temperature) causes the structure to collapse and/or self crimp.

In some embodiments, an extent of expansion of the device from a crimped state to an expanded state corresponds to a temperature at which the elastic recoil of the structure increases (e.g. temperature at which the structure collapses and/or self crimps). In some embodiments, strains of approximately 200%, and 400% correspond to collapse of the structure at 39° C. and 45° C. respectively where strain, for example is equal to expanded diameter/crimped diameter.

In some embodiments, the polymer portion comprise biostable grade polycarbonate based urethane (e.g. Chronoflex®) and/or polycarbonate-based thermoplastic polyurethane (e.g. Carbothane®). Optionally, in some embodiments, the polymer portion includes radiopaque material (e.g. in one or more part of the polymer portion).

In an exemplary embodiment the structure is deployed in the urethra following prostatectomy (e.g. as described herein) for up to 1 month, e.g. to facilitate drainage and maintain patency.

In an exemplary embodiment, the structure is deployed into a nasal lumen (e.g. as described herein) optionally postoperatively e.g. following facial plastic surgery, supporting healing tissues, for up to 1-3 months.

In an exemplary embodiment, the structure (or any other structure described herein) is deployed into a biliary lumen (e.g. a non-malignant biliary stricture), potentially facilitating drainage and maintaining patency for up to a 1 year.

Exemplary Structures Introduction

In some embodiments, treatments, e.g. as described previously in this document and/or in the examples, are carried out using exemplary structures and/or methods, e.g. as described below.

A broad aspect of some embodiments of the invention relates to balancing between forces applied by various parts of an expandable structure, especially for use in structures having a shape memory portion.

An aspect of some embodiments of the invention relates to an expandable structure (e.g. a stent) including at least a shape memory material (SM) portion and a second portion, where the SM portion includes strain induced behavior. The second portion is mechanically coupled to the first portion, for example being in an overlaying layer, and interferes with the relaxation of the first, SM, portion. In some embodiments, straining the SM portion reduces a SM portion expanding force. In some embodiments, reduction of SM portion expanding force is used to design a structure where, when the structure is in a crimped state, SM portion expanding force is low, for example, below a second portion expansion force (e.g. 50 MPa or less). In an exemplary embodiment of the invention, the SM expanding force is at least 10%, 20%, 30% or more (or intermediate percentages) less than the SM resisting force.

In some embodiments, when the structure is in a crimped state, the SM portion is highly strained. In some embodiments, a SM portion shape memory state (relaxed state) has a larger diameter than a crimped diameter. In an exemplary embodiment of the invention, the SM portion is treated (and sufficiently strained) so that the reduction in expansion force is at least 30%, 50%, 70%, 80% or intermediate percentages as compared to the same structure without treatment.

An aspect of some embodiments of the invention relates to a composite stent including a SM portion where the SM portion has different unloading stress and/or force, for different strains: In some embodiments, the SM portion has a different unloading stress/force, corresponding to crimped configuration strain, to an unloading stress/force corresponding to deployed configuration strains. For example, the difference can be, for example that the unloading force in crimped configuration is reduced by at least 30%, 50%, 70%, 80% or intermediate percentages as compared to a deployed configuration (e.g., a stent with a radius greater by a factor of 2, 3 or intermediate or greater factor). For non-tubular elements, "crimping" is provided by a change in length of the SM elements.

In some embodiments, the SM portion is treated such that the SM portion has an expanding force which decreases as a function of strain. In some embodiments, treatment comprises heat treatment. In some embodiments, the SM portion is treated such that it has a relaxed shape memory configuration (e.g. a tubular SM portion has a shape memory diameter). In an exemplary embodiment of the invention, the structure is designed to take this decrease into account, for example, to identify a suitable matching polymer whose hysteresis graph lies within a range between the higher expanding force and the lower expanding force of the SM portion.

In some embodiments, the SM portion is restrained by the second portion, where the second portion prevents and/or limits expansion of the SM portion. In one type of structure (e.g., a stent) the SM portion is predisposed to radially expand, while the second portion resists such expansion. In an alternative structure, the SM portion would contract and the second portion would resist such contraction. In some embodiments, the resistance is by force caused by elastic or super elastic relaxation.

Optionally or alternatively, the resistance is by a force caused by resistance to plastic or super-plastic and/or other deformation.

In some structures (stent or otherwise) the forces are not symmetric (rotationally and/or axially) and/or radial. For example, in a stent, a resisting force at one location may be smaller than at a different one and/or a SM force at one location may be larger at another location. This may cause the structure to bend and/or exhibit other asymmetric properties. Optionally, the force applied during bending is selected to be small. This may allow, for example, for a device to adapt to a shape of a surrounding lumen, but not enforce a particular curvature thereon.

In some embodiments, not all the structure is expandable and/or expands in a same direction. For example, one part may radially expand while another part is designed to maintain a fixed radius (e.g., not include expandable portions), and/or while a third part radially contracts. Optionally or alternatively, one part may be self expanding while another part may be balloon expandable. Also, a structure can be balloon expandable and once sufficiently expanded, may exhibit self-expansion properties. The converse is also within the scope of some embodiments of the invention, namely that the structure self expands up to one radius and is balloon expandable after.

In an exemplary embodiment of the invention, a stent as described herein shows a low recoil, for example, less than 10%, 5%, 3%, 1% or intermediate percentages of recoil in diameter after deployment.

An aspect of some embodiments of the invention relates to an expandable structure which is substantially stable in more than one configuration. For example, the expansion and/or contraction force applied by the structure may be less than a threshold. In an exemplary embodiment of the invention, the threshold is substantially zero. Optionally or alternatively, the threshold is less than 50%, 30%, 20%, 10%, 5% or intermediate percentages of the force applied by any part of the device at that configuration. In an exemplary embodiment of the invention, the device is formed of a SM portion and a second portion, optionally polymer, but optionally, formed of other materials, for example, SM. In an exemplary embodiment of the invention, at least 10%, 20%, 30%, 40%, 50% or intermediate percentages by volume of the structure are formed of a SM material.

In some embodiments, a structure is stable in a crimped state and a plurality of expanded states, optionally covering a continuum. For example, in some embodiments, a tubular structure has a continuum of ranges of diameters. In some embodiments, a deployed diameter is 1.5-3 times a crimped diameter, for example, between 1.7 and 2.8. Optionally or alternatively, the range covers a factor of at least 1.5, 2, 3, 4 or intermediate or greater ranges of diameters.

Optionally, the stable range (e.g., deployed for a stent) is separated from a stable configuration (e.g., crimped for a stent) by an unstable region. Optionally or alternatively, the stable range may consist of a plurality of stable points (e.g., be discrete), for example, 3, 4, 5, or more separated by configuration which tend towards a nearby stable point.

In some embodiments, the SM portion and the second portion are configured such that the SM portion is configured to apply an expanding force and the second portion has a reactive contracting force to the expanding force. In some embodiments, the structure is stable as the SM portion expanding force and the second portion reactive contracting force are balanced.

A potential benefit of balanced forces is, in some embodiments, the structure exerts substantially no outwards force. For example, for a tubular structure, the structure exerts substantially no radial outwards force. In some cases, the force exists, but is low enough that it can be counteracted by the surrounding lumen. Optionally or alternatively, the force is absent due to hysteresis behavior of one or both of the portions or due to a portion exhibiting plastic deformation resisting the deformation implied by the net force applied by the two portions.

In an exemplary embodiment of the invention, while the applied outwards force is low, the resistance to crushing is considerably greater, for example, by a factor of 2, 3, 5, 7, 10, 15, 20 or intermediate numbers. It is noted that in regular SM stents crush resistance is often 50% or less of radial force. In some embodiments of the invention crush resistance is lower in absolute number numbers (10-30% lower, for example as compared to a SM stent of similar design. However, as radial force is so low, greater ratios can be achieved.

In some embodiments, a structure is configured such that a SM portion expanding force is less than a force required to expand the second portion (a second portion expansion force) and the second portion contracting force is less than a force required to contract the SM portion (a SM contraction force).

In some embodiments, there are a range of stable deployed configurations. In some embodiments, a tubular structure has a range of stable deployed diameters. In some embodiments, stable deployed diameters are between a SM portion shape memory diameter (e.g., in a memory state) and a second portion relaxed diameter.

In some embodiments, the structure has high resistance to radial crimping forces, for example, corresponding to a SM portion loading force. In some embodiments, loading or crimping of the SM portion follows a stress-strain curve including an elastic portion with strain proportional to stress, followed by a super-elastic portion where small increases in stress correspond in large strains (loading plateau). In some embodiments, the SM portion unloading plateau has high stress/forces, corresponding with high forces required to radially crimp the structure. A potential benefit of high forces required to crimp the structure, is structure resistance to collapse. In some embodiments, loading plateau forces of the SM portion are for example, between 50 and 1000 MPA, for example, between 200 and 700 MPA, for example, approximately 450 MPa.

In some embodiments, the structure elastically deforms under low strain. In some embodiments, under a low strain, the SM portion behaves elastically (e.g. remaining martensite). In some embodiments, under a low strain the second portion behaves elastically or plastically and/or does not interfere with the elastic behavior of the SM portion. For example, when a unidirectional crushing force is applied and removed, the structure returns to an original deployed configuration. In some embodiments, the reactive force (to the crushing force) of the second portion (e.g., a polymer portion), is almost zero, corresponding to a small strain of the polymer portion. Once local pressure P1 is removed, for example, as the polymer portion has not significantly changed in circumference, the SM portion returns to a pre-deformation deployed configuration.

In an exemplary embodiment of the invention, the SM material is selected to have a strong memory, so that the range over which this elastic behavior is exhibited is large enough for, for example, resistance to deformations of between 0.1 and 10% of the diameter of the structure. Such resistance can correspond to SM material strain of between 0.1% and 2%, for example, depending on stent design parameters.

In some embodiments, the SM portion includes temperature dependent characteristics. In some embodiments, the SM portion expanding force changes upon a temperature change.

For example, in some embodiments, a temperature change reduces the SM radial resistance force (e.g. below the contracting force of the second portion) and the structure collapses and/or self-crimps and/or otherwise deforms.

For example, in some embodiments, a temperature change increases the SM expanding force (e.g. above a radially contracting force of the second portion) and the structure expands and/or self-deploys.

In some embodiments the structure is tubular. In some embodiments, the structure is a tubular mesh or lattice with multiple apertures therein and a coverage percentage of, for example, between 1% and 70%, for example, between 10% and 50%, for example, between 15% and 25%. In some embodiments, the structure is shaped to be used as a stent. In some embodiments, the SM portion is tubular and/or the second portion is tubular.

In some embodiments, the structure includes a plurality of axial segments (e.g., between 2 and 10, for example, between 3 and 5). In some embodiments, segments are coupled by a plurality of connectors. In one design family, the SM portions are provided as discrete segments interconnected by the second portion. Optionally, this provides a plurality of bending points where properties of the second portion dictate the bending properties of the device, optionally increasing flexibility.

Optionally or alternatively, SM interconnectors are used. Optionally, the connectors are treated to not exhibit SM behavior at the working temperatures used.

In some embodiments, the structure is bifurcated, for example, in some embodiments, connectors between segments connect two structures (e.g. as described herein) to create a bifurcated structure.

In an exemplary embodiment of the invention, the SM segments are interconnected by an overlying tube comprising at least part of the second portion. The ends of this tube optionally extend past one or both ends of the outermost SM segments.

In some embodiments, an axial geometry enclosed by the structure, when in a relaxed state and/or uniformly expanded state is rotationally symmetrical (e.g., to within 10% variation in diameter at each axial location and/or ignoring axial bending). For example, in some embodiments, a tubular structure has a circular axial enclosed geometry. In some embodiments, an axial geometry enclosed by the structure, varies at different points along a structure length. For example, in some embodiments, different segments have different axial geometries enclosed by the structure. For example, a structure with a first tubular segment and a second tubular segment has, in some embodiments, a first segment deployed diameter larger than a second segment deployed diameter and/or having a different design (e.g., surface pattern). A potential benefit of a different enclosed axial geometries/properties along a structure length is better conformability of the deployed structure (e.g. to a lumen), as compared to a stent with uniform axial behavior.

In some embodiments, an axial geometry enclosed by the structure at one or more points along a structure length is asymmetrical, for example, the axial geometry enclosed by the structure is oval. A potential benefit of asymmetrical enclosed axial geometries is good conformability of the deployed structure (e.g. to a lumen).

In some embodiments, one or more segment SM portion has a different treatment from other segments. In some embodiments, one or more segment SM portion and/or polymer portion has different geometry e.g. one or more of axial geometry, thickness, length and/or surface aperture pattern and/or dimensions.

In some embodiments, each segment includes a SM portion and a second portion. In some embodiments, connectors are flexible. A potential benefit of flexible segments is flexibility of the crimped stent for ease of deployment and/or conformability of the deployed stent to a lumen.

In some embodiments, connectors do not include SM material. In some embodiments, connectors include second portion material (e.g., such as polymer). In an exemplary embodiment of the invention, a first segment is connected to a second segment by between 1 and 7, for example, between 2 and 5, circumferentially arranged connectors. Different inter-segment portions may have different numbers and/or positioning and/or relative circumferential positioning of the connectors.

In some embodiments, connectors include SM material. In some embodiments connectors are formed of both SM material and material as used in the second portion (e.g., a polymer).

In some embodiments, the SM portion includes a shape memory alloy (SMA), for example Fe—Mn—Si, Cu—Zn—Al, Cu—Al—Ni, NiTi. In some embodiments the SM portion is nitinol (NiTi). In some embodiments, the SM portion includes a NiTi-based ternary alloy, for example NiTi—Cu, NiTi—Co, NiTi—Pd, NiTi—Pt, NiTi—Zr, NiTi—Hf.

In some embodiments, the second portion exhibits elastic hysteresis. In some embodiments, the second portion includes polymer or a high-recoil polymer. Exemplary polymers which may be used (e.g., with exact properties possibly selected according to the application, possibly using principles as described herein, include: Silicone elastomer, Silastic elastomer, Polyurethane, carbosil, Desmopan (Bayer), Carbothane (Lubrizol), Tecothane (Lubrizol), Tecoflex (Lubrizol), ChronoFlex® C; CarboSil (DSM), Texin (Bayer) etc.

In some embodiments, a method of use of a structure includes inserting the structure into a lumen in a crimped configuration and expanding the structure to a deployed configuration inside the lumen (e.g. expanding on an inflatable balloon and/or self-deploying e.g. upon a temperature change).

An aspect of some embodiments of the invention relates to an expandable structure exhibiting SM and/or elastic behavior which is deployed using balloon expansion over the range of deployment states where SM and/or elastic behavior is exhibited by the component parts of the structure. A potential benefit of balloon deployment is control of expansion speed, positioning and/or extent.

In some embodiments, the structure is expanded using a compliant balloon (e.g. using a low inflation pressure for example, using an inflation pressure of 0.1-5 atmospheres, or 0.3 to 2 atmospheres). A potential benefit of structure deployment using a compliant balloon is a highly conformed stent shape to lumen geometry.

In some embodiments, the structure is expanded using a non-compliant balloon (e.g. of 5-15 atmospheres, or 5-8 atmospheres, or 12-15 or 18 atmospheres, or about 8 atmospheres). A potential benefit of structure deployment using a non-compliant balloon is that the stent can be used to open and/or enlarge a lumen (e.g. a body lumen), according to the balloon size (e.g., combined PCTA and stenting, direct stenting).

In some embodiments, a method of use of a structure includes deploying the structure more than one time, for example, redeploying (e.g. for correct positioning), where the structure is crimped (e.g. self-crimped) in between deployments.

In some embodiments, a method of use of a structure includes removing the structure a time period after deployment, for example, by self-crimping the structure onto a deployment/removal device (e.g. a catheter).

An aspect of some embodiments of the invention relates to an expandable structure where a length of the structure remains substantially the same in crimped and deployed configurations. In some embodiments, the structure includes a plurality of coupled flexible members and a plurality of rigid members where the rigid members are orientated generally axially (e.g., a centerline thereof lying, within 30 degrees of parallel to the axis) along the structure. In some embodiments, axially orientated rigid segments are interconnected by connectors which can morph to accommodate difference in expansion of different segments. Optionally, each such segment optionally includes one or more of the struts described below.

In some embodiments, each rigid member is coupled to two other rigid struts and each coupling is by at least one flexible member. In some embodiments, when the structure expands and/or contracts (deploys and crimps respectively) the flexible members bend during contraction and unbend during expansion of the structure. In some embodiments, bending of the flexible members brings the rigid members together (crimping) and unbending pushes the rigid members apart (deploying).

An aspect of some embodiments of the invention relates to an expandable structure where the structure is kink resistant, the structure bends without closing the structure at a bend and/or substantially (e.g., by more than 20%, 10%, 5% or intermediate percentages) decreasing an axial geometry enclosed by the structure at the bend (e.g., the structure which is defined if all the apertures in the surface are filled in with sections that match a general curvature of the surface. In some embodiments, the structure includes a plurality of circumferential segments, where segments are coupled using connectors. In some embodiments, connectors are axially compressible and/or expandable. In some embodiments, at a bend, connectors expand at the outer side of the bend and/or contract at the inner side of the bend. In some embodiments, connectors each include one or more flexible strut, each flexible strut comprising a vertex around which the strut bends axially to compress the connector. In some embodiments, one or more connector includes at least one rhombic shape or other closed shape. Optionally, the shape increases a flexibility of radially resistant surfaces and/or provides such flexibility between them).

Exemplary Structure with Stable Crimped and Deployed Configurations

Referring now to the drawings, FIG. 1A is a simplified schematic cross sectional view of a structure in a crimped configuration within a lumen 100, according to some embodiments of the invention. In some embodiments, the structure is delivered to lumen 100, and/or a target portion of lumen 100, by a deployment device 102 (e.g. catheter). In some embodiments, the structure includes a SM portion 104 coupled to a resistive second portion 106, for example, and elastic portion (e.g. polymer). In some embodiments the portions are coupled such that SM portion 104 is contained within or held by second portion 106.

In an exemplary embodiment of the invention, the lumen is a body lumen and the stent is formed of and/or coated with bio-compatible materials. In an exemplary embodiment of the invention, the lumen is a natural lumen such as a blood vessel (e.g., artery or vein), part of GI tract (e.g., esophagus, stomach, duodenum, small intestine, large intestine or rectum), urethra, ureter, part of a kidney, bronchi and/or sinus cavities. Optionally, the stent is provided sterile, optionally in sterile packaging and/or with instructions for use. Optionally or alternatively, the stent is used for artificially formed lumens, such as to separate tissues and/or for apertures formed in organs (e.g., the skin).

The application may determine one or more desirable stent properties, such as one or more of length, crimped diameter, maximum deployed diameter, range of stable diameters, degree of conforming, crush resistance and/or maximum applied radial force. In an exemplary embodiment of the invention, such properties are achieved using selection methods as described herein. For example, once stent properties are known, various options for design and properties of the SM portion and second portion can be matched to see which pairing provides a desired result.

Optionally, a search is made of the space of such pairings to find a best or satisfactory match between the stent design and the properties. As can be understand, the above properties can be modified, for example, by selecting portion strength, amount of induced strain and/or relaxed geometry. In an exemplary embodiment of the invention, the geometry of the stent is selected according to the desired amount, uniformity and/or location of induced strain (and/or e.g., affect of crimping on stent behavior and/or properties when deployed of a crimped stent). As noted herein, the amount of strain affects self-expansion force, in some stents according to exemplary embodiments of the invention. So, for example, a stent where more of the strain is concentrated at certain joints, will exhibit a lower self-expansion than a stent where the strain is more evenly spread over the stent (e.g., when entire struts are deformed, rather than just joints thereon) and, hence, in general lower and less affecting (reducing) of the expansion forces. In an exemplary embodiment of the invention, designs are selected (e.g., as appropriate) where 10%, 20%, 40%, 70%, 80% or intermediate or greater or smaller percentages of the stent carry at least 50% or 80% of the strain. In accordance with some embodiments of the invention, greater percentages of the stent carrying strain generally indicate a more uniform straining and hence a lesser reduction in self-expansion forces.

For example, for smaller blood vessels (lower extremity, for example) stent (total, composite) thickness can be 0.05-0.5 mm thickness, for example, 0.08-0.3 mm, for example, 0.1-0.15 mm in deployed condition with length, for example, up to 150 mm (e.g., 20, 40, 80 or intermediate or greater length), and/or with surface coverage of between 5% and 60%, for example, between 10-30%. For large vessels (SFA) or GI (biliary & esophageal) SM portion is optionally 0.1-0.9 mm, for example, 0.15-0.4 mm thick and Poly portion is 0.05-0.6 mm, for example, 0.1-0.4 mm thick (e.g., varied between normally open and normally closed stents), length, for example, up to 200 mm (e.g., at least 10, 20, 40, 80, 150 or intermediate length in mm), and/or surface coverage from 20 to 95%, for example, between 25 and 45%.

In some embodiments, the crimped structure is small enough to be inserted into a lumen 100, e.g. thinner than a minimum distance between lumen walls 108, 110. In some embodiments, the crimped structure is 3.5-4.5 mm diameter or 3-5 mm diameter. In some embodiments, the crimped structure is less than 3.5 mm in diameter, e.g. 1-1.5 mm. In some embodiments, the crimped structure is more than 4.5 mm in diameter. Crimping ratio can be (ratio between crimped and deployed state), for example, between 1:2 and 1:10, or intermediate numbers, or greater, depending on the stent design.

Figure 1B:
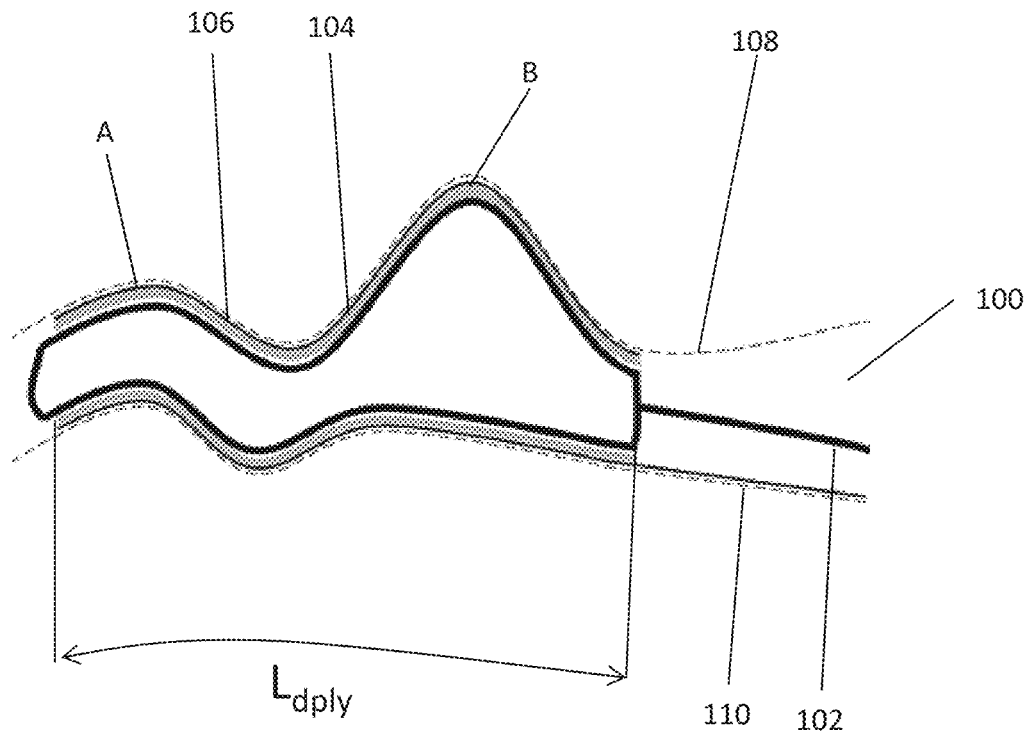
FIG. 1B is a simplified schematic cross sectional view of a structure in a deployed configuration within a lumen, according to some embodiments of the invention.

FIG. 1B is a simplified schematic cross sectional view of a structure in a deployed configuration within a lumen 100, also showing optional adaptation to the lumen, according to some embodiments of the invention.

In some embodiments, the structure is expanded into a deployed configuration by a deployment device 102. In some embodiments, the structure is deployed by expansion of at least a portion of deployment device 102, for example, by inflation of a balloon.

FIG. 1B shows a possible consequence of structure balance in a range of configurations, e.g. a range of deployed diameters. In some embodiments, the structure, in a deployed configuration, has more than one diameter and/or axial geometry enclosed by the structure along a structure length: a structure transverse dimension at point A along length $L_{dply}$ of the structure is smaller than a structure transverse dimension at point B.

Apparent Composite Stents of the Art

Figure 2:
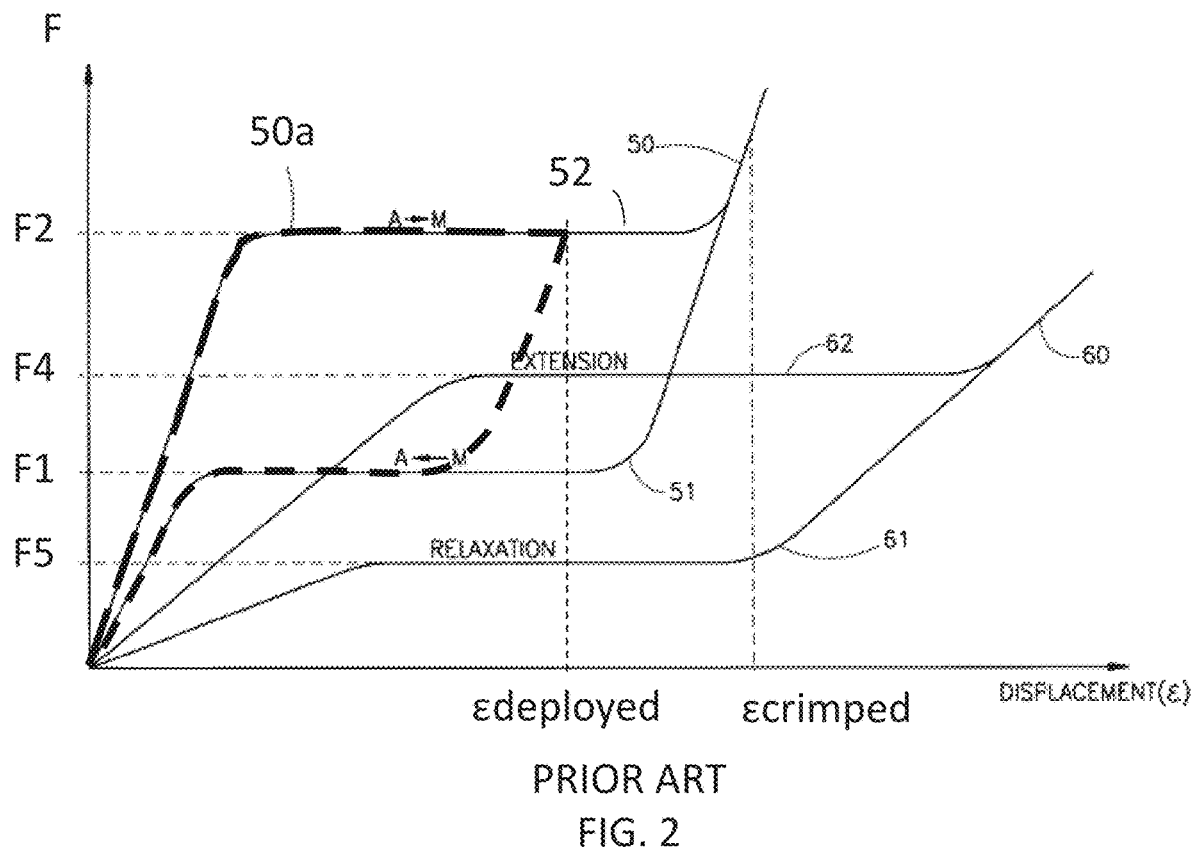
FIG. 2 presents a plot of applied force, F, with strain, $\varepsilon$, for a SM portion and for a plastic material portion of a composite stent apparently described in the art.

Described in the art are composite stents including a SM portion and a plastic portion, however, as will be explained below, it is not clear that such are possible. FIG. 2 presents a plot of applied stress, F, with strain, ε, for a SM portion and a plastic material portion of a composite stent described in the art. Hysteresis plot 50 shows the stress-strain relationship of the SM portion, where lower curve 51 corresponds to expansion of the stent (unloading of the SM portion) from the crimped configuration and where upper curve 52 corresponds to crimping of the stent. Hysteresis plot 60 shows the stress-strain relationship of the plastic portion where upper curve 62 corresponds to expanding of the stent and lower curve 61 corresponds to crimping of the stent.

Of note is hysteresis plot 50a, in particular, the lower curve, corresponding to expansion of the stent from a deployed configuration where the expanding force, F1 of the SM portion in the crimped configuration is the same as the expanding force of the SM portion in the deployed configuration.

The stent does not expand from a crimped configuration, where strain=εcrimped, since expansion of the SM portion exerts a force F1 which is less than the force required to expand the plastic portion, F4, F1<F4.

In a deployed configuration, e.g. εdeployed, the stent is stable, the stent does not expand, as F1<F4, and the stent does not collapse, as the relaxation or contraction force of the plastic portion, F5, is less than the force needed to crimp the SM material, F2 (F5<F2).

To expand or deploy the stent from the crimped configuration scrimped, a force greater than or equal to, F=F1−F4 is applied.

Generally, for most materials, the upper and lower parts of the stress/strain hysteresis curve are similar, for example, F2=F1+δ, F4=F5+δ where δ is small. Therefore, although, theoretically, a match between a SM material and a plastic (or other material) such that F1<F4 and F2>F5 in the deployed configuration and where F1<F4 in the crimped configuration might be found, the inventors are not aware of any practical match. Even were such a match found, the size of the overlap is very small, effectively dictating a narrow or single range of stable diameters. In some embodiments of the invention, material treatment and/or stent design are selected to increase the possibility of a match with practical results, for example, as shown in the examples below.

Figure 3:
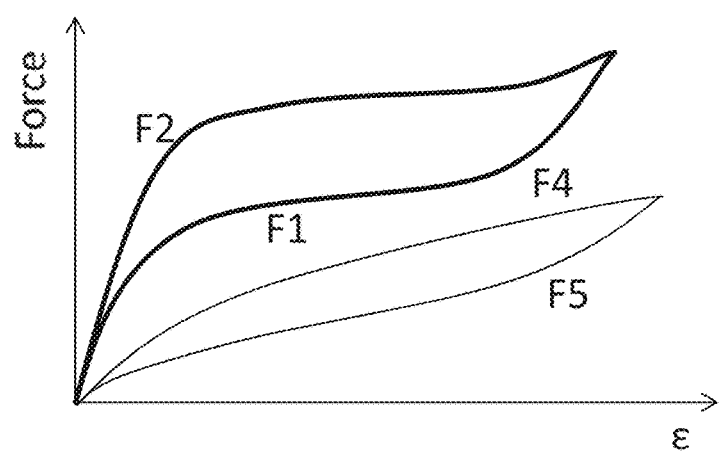
FIG. 3 presents a plot of applied force, F, with strain, $\varepsilon$, for materials for a composite stent apparently described in the art.
Figure 4:
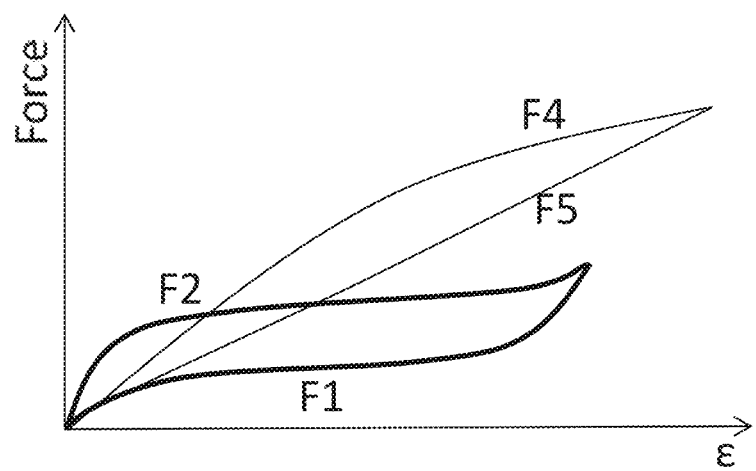
FIG. 4 presents a plot of applied force, F, with strain, $\varepsilon$, for materials for a composite stent apparently described in the art.

FIG. 3 and FIG. 4 show two examples of ineffective material matching.

FIG. 3 presents a plot of applied force, F, with strain, ε, for materials for a composite stent. F2>F5, but F1>F4, so a composite stent using these materials is stable when deployed, but is not stable in the crimped configuration.

FIG. 4 presents a plot of applied force, F, with strain, ε, for materials for a composite stent. F1<F4, but F2<F5, so a composite stent constructed using these materials is stable when in the crimped configuration, but the deployed stent is not stable and collapses back to the crimped configuration.

As explained herein (e.g., FIGS. 5 and 6), in an exemplary embodiment of the invention, the properties of the SM material are modified such that a practical match is more easily found.

Exemplary Strain Dependent Material Characteristics

Generally, shape memory alloys transform from martensite crystal structure to austenite crystal structure upon heating. When heating, in a range of transformation temperatures between a transformation start temperature As and a transformation finish temperature Af (where As<Af), the alloy is neither austenitic or martensitic, and exhibits superelastic material characteristics. As the shape memory alloy is heated further, above Af, the memory alloy eventually reaches a temperature, Md, a maximal temperature when martensitic transformation occurs at stress.

Shape memory alloy transformation temperatures (e.g. As, Af) are generally known to be dependent from applied stress and are somewhat dependent on applied strain, As=As(ε), Af=Af(ε). However, generally, the influence of strain on transformation temperatures (where the strain is within the limit of SM devices being used, e.g., 0 to 8%) is small, e.g. up to about 1-2° C.

In some embodiments, a SM portion is treated such that transformation temperatures show high strain dependence. For example, the influence on transformation temperature can be, for example, 3, 4, 5, 7, 8, 10, 15, 20 degrees Celsius or intermediate or greater difference in transformational temperature, for shape memory in the 0-8% strain range.

In some embodiments, treatment is heat treatment, e.g. as described below. In some embodiments, a SM portion is treated and sized such that a difference in strain between a crimped configuration and a deployed configuration generates a transformation temperature change the SM portion expanding force such that the mechanical properties of the SM portion are as desired in relation to the second portion (e.g., as described above) in the crimped and deployed configuration. For example, in some embodiments, at 3% strain As=15° C. and Af=25° C., whereas, at 7% strain As=28° C. and Af=32° C.

In some embodiments, transformation temperatures, when the structure is in a crimped configuration, A's, A'f, are different to transformation temperatures, when the structure is in a deployed configuration. In some embodiments A's>As and/or A'f>Af (e.g., by the above noted differences).

Figure 5:
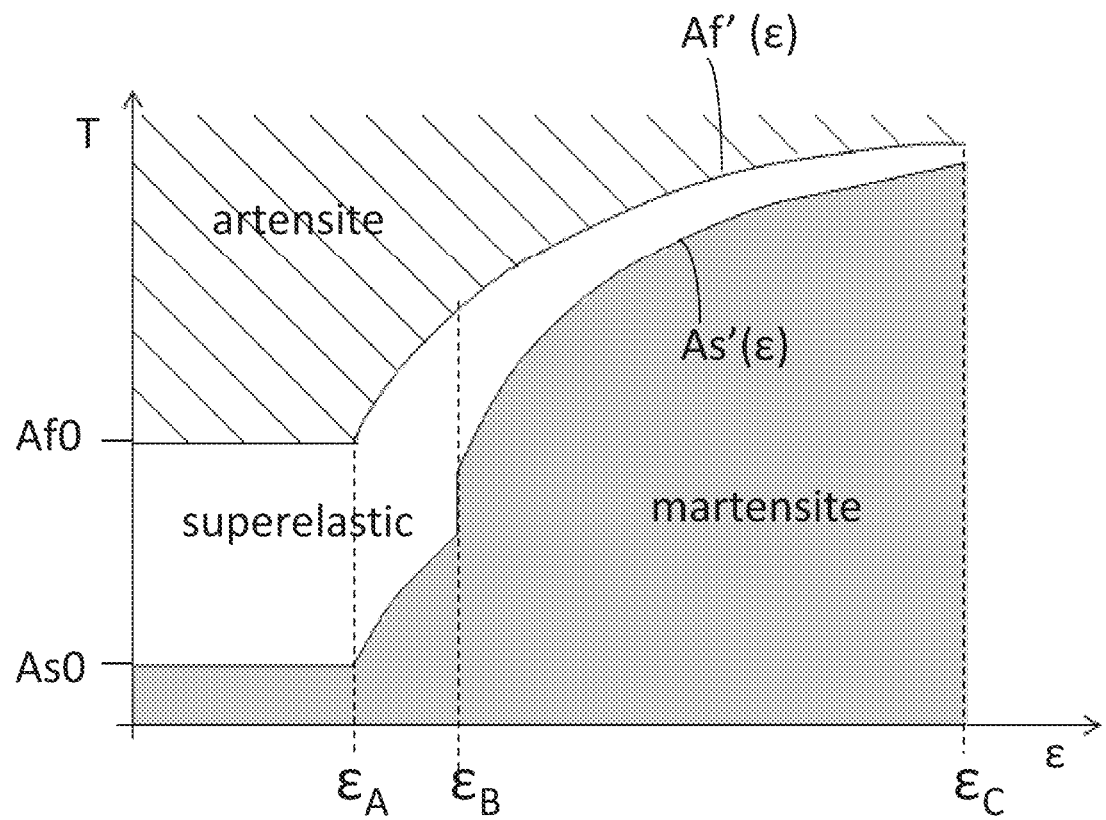
FIG. 5 presents plots of shape memory material austenite transformation start temperature, $A_s$ and austenite finish temperature $A_f$, with strain, for stent materials used according to some embodiments of the invention.

FIG. 5 presents plots of shape memory material austenite transformation start temperature, As, and austenite transformation finish temperature, Af, with strain, for stent materials used according to some embodiments of the invention. FIG. 5 shows that, below temperature As'(c) the material is martensite (solid gray shading), above temperature Af'(c) the material is austenite (striped) and, above temperature As'(c) and below temperature Af'(c) the material is superelastic (white).

Figure 6:
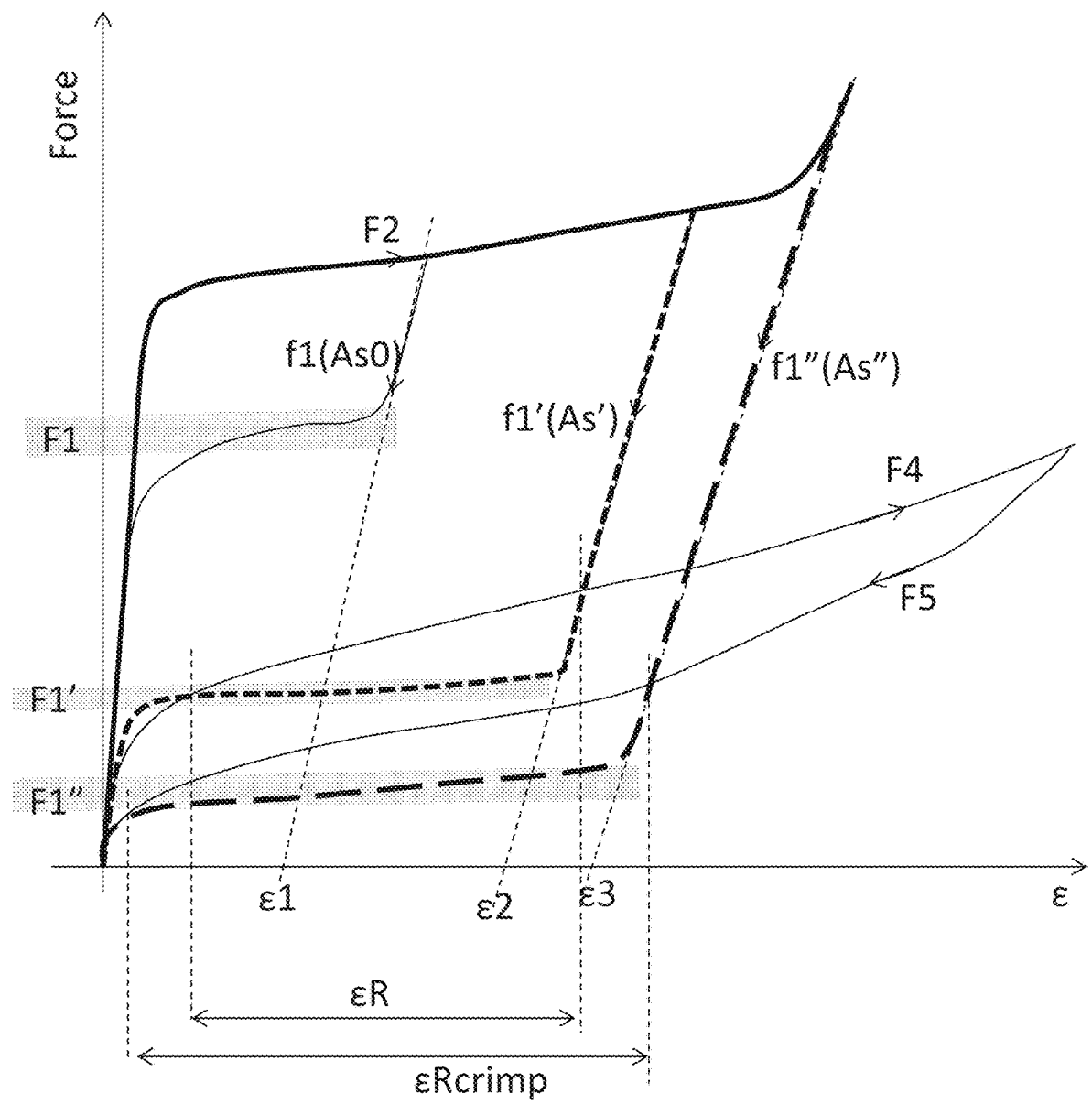
FIG. 6 presents a plot of a force-strain hysteresis curves for a SM portion and a force-strain hysteresis curve for a polymer portion, according to some embodiments of the invention.

It should be noted with respect to FIGS. 5 and 6 (and some other charts herein), that what is shown are the shape-memory properties of the material from which the SM portion is constructed in accordance with some embodiments of the invention. However, in the body, actual forces are applied by the stent, not by component materials. The use of diagrams such as FIGS. 5 and 6 allows the effect of the stent structure to be ignored. It is noted, however, that some embodiments of the invention utilize the stent structure and/or stent crimping/deployment state, to affect how the material acts, for example, stent crimp amount and/or design can affect which part of FIG. 6 is traversed.

Referring to FIG. 5, for example, at a temperature Af0, for different strains, $\varepsilon_A$, CB the shape memory material is at a different stage in the transformation; under strain CA the alloy crystal structure is at the end of the transformation (at a border between superelastic and austenite), and under strain CB, the crystal structure is at the beginning of the transformation (at a border between superelastic and martensite). The differences in crystal structure are reflected in material characteristics, at the same temperature, for different applied strains.

In some embodiments, at a temperature range between room temperature and body temperature (e.g. 18° C.-39° C.), increasing the strain on a structure initiates a martensitic transformation in a SM portion of the structure, and reduces the expanding force of the SM portion. In some embodiments, increasing deforming strain on the structure and/or SM portion causes, for example decreasing of the mechanical hysteresis curve lower plateau. In an exemplary embodiment of the invention, a design can use these properties to select a desired curve, within the range possible for the material.

FIG. 6 presents a plot of stress-strain hysteresis curves for a SM portion and a polymer portion, according to some embodiments of the invention. It should be noted that the strain scale of the polymer plot is not the same as the SM plot, as polymers can often work under strain of 400-500%, while Nitinol may only work with strain up to 8%. In some exemplary embodiments of the invention, this difference in strain capability is used to provide different structures for the SM and second portions, with the SM being designed to reduce strain in all parts of the device to below 8%. A polymer section, for example, can have a small relaxed diameter (corresponding to desired crimp diameter) and still allow a great increase in diameter (e.g., a factor of 10 or more, such as 15 or 20) thereof during deployment.

Illustrated are three SM unloading curves $f_1(A_s)$, $f_1'(A_s')$, $f_1''(A_s'')$ each associated with unloading from a different strain on the SM portion: $F_1$ is associated with unloading from strain $\varepsilon_1$, $F_1'$ with $\varepsilon_2$, and $F_1''$ with $\varepsilon_3$, where $\varepsilon_1 < \varepsilon_2 < \varepsilon_3$.

Each unloading curve includes an unloading plateau, $F_1$, $F_1'$, $F_1''$, which, for simplicity, is referred to as a single force value.

Exemplary Balance of Contracting and Expanding Forces

Figure 7:
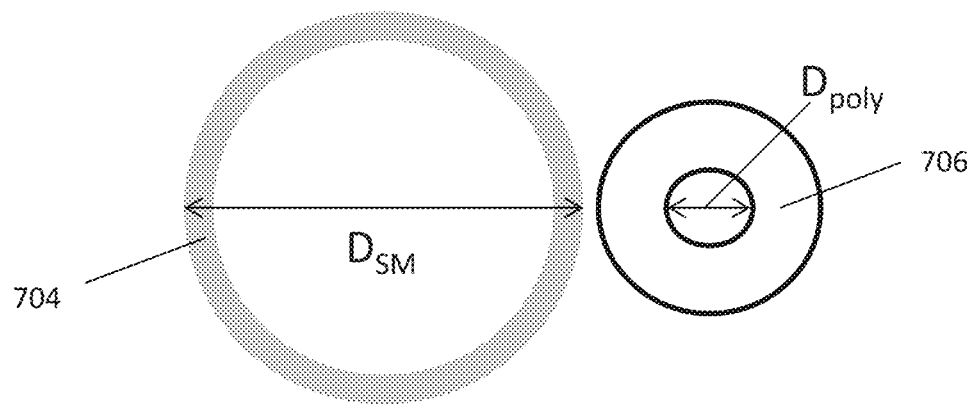
FIG. 7 is a simplified schematic of an uncoupled SM portion and a polymer portion, according to some embodiments of the invention.

In some embodiments, a radially expanding force of a SM portion is balanced by a radially contracting force of a polymer portion. FIG. 7 is a simplified schematic of an uncoupled SM portion 704 and a second portion 706, according to some embodiments of the invention.

In some embodiments, SM portion 704, has a relaxed (e.g. shape memory) diameter, which is larger than that of a relaxed diameter of second portion 706; $D_{SM} > D_{poly}$. In some embodiments, coupling of SM portion 704 and second portion 706, for example, corresponds with stretching of second portion 706 and/or compression of SM portion 704. For example, in some embodiments, the polymer relaxed diameter is 75% or less, 50% or less, 25% or less, than the SM relaxed diameter. For example, in some embodiments $D_{SM}$ is approximately 12 mm and $D_{poly}$ is approximately 3 mm.

In some embodiments, for example, for force equilibrium at deployed diameters, $D_{SM}$ is larger than the largest deployed diameter.

In some embodiments, expanding a structure where SM portion 704 and second portion 706 are coupled such that and SM portion 704 is compressed and second portion 706 is stretched, corresponds with unloading or relaxing the SM portion and extending or loading the polymer portion. Referring now back to FIG. 6, expanding the structure corresponds with moving along curve F4 for the polymer and, depending on the strain applied to the SM portion, moving along one of the unloading curves f1(As), f1'(As'), or f1''(As'').

In some embodiments, radially compressing, closing or crimping the structure corresponds with loading the SM portion and relaxing the polymer portion. Referring to FIG. 6, crimping the structure corresponds with moving along curve F5 for the polymer and moving along curve F2 for the SM portion.

In some embodiments of the invention, using a polymer portion to offset some of the SM portion properties allows a stronger SM material to be used, for example, more material or material with a stronger memory. In an exemplary embodiment of the invention, this translates into an elongation of the elastic loading of the curve in FIG. 6. Optionally, this curve is elongated by 20%, 40%, 50%, 60%, 80% or more relative to what is used for a same stent without the polymer layer.

Exemplary Heat Treatment

In some embodiments, a SM portion is treated such that, in a crimped configuration, the transformation temperature is at least 5° C. above the transformation temperature in a deployed configuration. For example, in some embodiments, a crimped configuration transformation temperature, Af'=22° C. and a deployed configuration transformation temperature, Af'=15° C.

In some embodiments, a SM portion is treated such that, in a crimped configuration, where $\varepsilon = \varepsilon_3 = 7\%$, D=2 mm, an unloading stress, F1'', is approximately 50 MPa.

In some embodiments, a SM portion is treated such that, in a deployed configuration, where $\varepsilon = \varepsilon_2 = 2\%$, D=10 mm, an unloading stress, F1', is approximately 300 MPa.

In some embodiments, a SM portion is treated and/or a SM portion material is selected such that, a loading, resisting (crimping) stress, F2, is approximately 450 MPa.

Values intermediate, smaller and/or greater than the above values can be achieved as well and are limited only by the material properties, the above values being only exemplary.

In some embodiments, a SM portion is heated to a high temperature, then subjected to a solution treatment, constrained and subjected to a memorizing treatment and then to an aging treatment.

In some embodiments, a SM portion is subjected to a solution treatment, to a shape setting treatment and an aging treatment.

Generally, solution treatment is where a metal portion is heated to a temperature high enough to allow a constituent of the metal to enter into solid solution, and is then cooled rapidly (e.g. using water quenching) to hold that constituent in solution. Generally solution heat treatments soften.

Generally, memorizing treatment, or shape setting forms the material into a new memory shape. Memorizing treatment generally involves firmly constraining the material into a new shape (e.g. in a fixture or on a mandrel) and then performing a heat treatment. The heat treatment time should be such that the material reaches the desired temperature throughout its cross-section. The time will depend on the mass of the fixture and material, and the heating method.

Generally, aging treatments are done to raise the austenite finish (Af) temperature of superelastic Nitinol components. Generally, aging is done by heat-treating to about 300-480° C. for extended periods. Generally, longer aging treatments are associated with higher Afs. For example, in some embodiments, a SM portion is subjected to the treatment described in Example 2 of U.S. Pat. No. 5,882,444: The SM portion is heated to 500° C. for 1 hour and then to a solution treatment at 650° C. for 20 mins. The SM portion is then constrained and subjected to a memorizing treatment at 520° C. for 30 mins, and then to aging treatment at 400° C. for 2 hours.

Other shape memory setting treatment and/or transformation temperature tailoring treatments of the art and/or other parameter values are suitable for use and are within the scope of some embodiments of the invention. In some exemplary embodiments of the invention, what is important is that the material be shown to exhibit a change in force due to applied strain, independent of the treatment method that achieves it; and that this change in force be utilized in stent design and/or usage.

In an exemplary embodiment of the invention, parameter values are selected according to a desired effect on SM properties. Optionally, after applying the treatment, SM properties are tested, for example, to measure the hysteresis curve of FIG. 6, or just to detect a difference in applied force as a function of strain, for example, at 2, 3 or more points of strain, to determine if the parameters yield a suitable effect (for example, effects as described herein). Optionally, the testing is done on a complete stent, or possibly only on a SM part of such a stent or other structure.

Exemplary Crimped Configuration

In some embodiments, in a structure crimped configuration, the structure is highly compressed and SM portion experiences a large (e.g., between 4 and 7%) strain, for example, a strain $\varepsilon_3$ corresponding with SM material behavior from unloading curve f1''($A_s$''). For example, in some embodiments, a diameter of the crimped structure is less than a fifth of $D_{SM}$ or up to a tenth of $D_{SM}$ or less than a tenth of $D_{SM}$ or intermediate fractions of $D_{SM}$.

Referring to FIG. 6, radially expanding forces of the crimped SM portion are low, F1'' is lower than the force required to expand the polymer, F4. In some embodiments, F1" is approximately 50 MPa. This represents a stable crimped configuration.

Figure 8A:
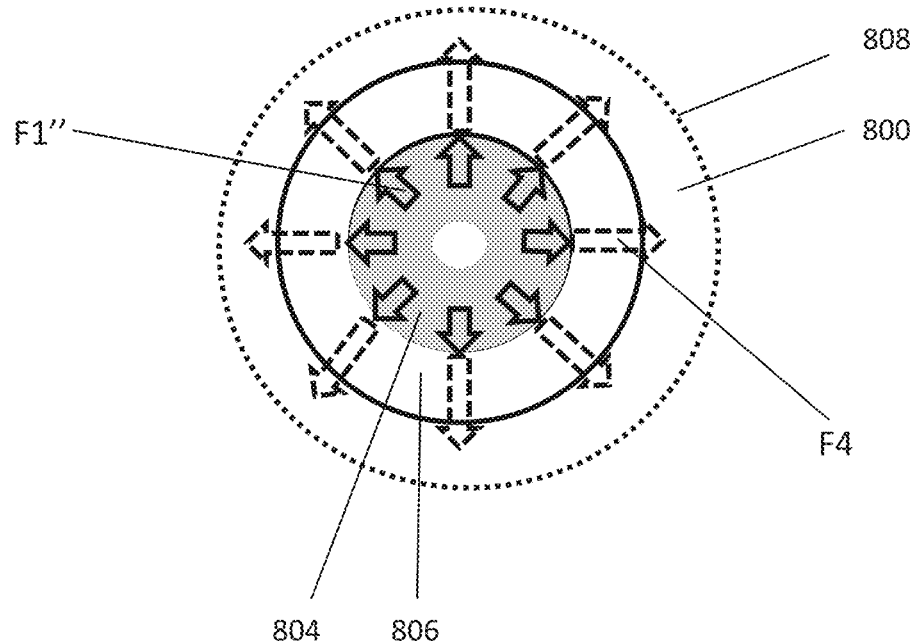
FIG. 8A is a simplified schematic cross sectional view of a structure in a crimped configuration, according to some embodiments of the invention.

FIG. 8A is a simplified schematic cross sectional view of a structure in a crimped configuration, according to some embodiments of the invention. The structure is optionally disposed within a lumen 800 (lumen includes lumen walls 808). In some embodiments, for example, for force balance, a radially expanding force F1" of a SM portion 804 is less than a force F4 needed to expand a second portion 806; F1"<F4. In the crimped configuration, force balance between the SM and polymer portion, for example, means that the stent stably remains in the crimped configuration, e.g. for accurate and safe deployment. Optionally or alternatively, the stent remains in stable configuration also during partial expansion thereof. Further, it is possible to selectively inflate/expand only a part of the device e.g., so as to engage the lumen, while other parts of the device are less, or not, deployed.

Exemplary Deployment

In some embodiments, to expand or deploy the stent from the crimped configuration, a force greater than or equal to, Fexpansion=F4−F1" is applied. For example, in some embodiments, expansion force is applied to the structure by a deployment device (e.g. by filling/inflating a balloon deployment device). In some embodiments, Fexpansion is low. A potential advantage of low Fexpansion is ease of deployment. It should be noted that the SM portion can help with the deployment the Polymer portion, so, overall, a lower deployment force is needed and/or lower stress polymer can be used (as after deployment it is supported by the SM portion.

In some embodiments, a structure is mounted directly on a balloon deployment device for direct stenting.

In some embodiments, a structure is expanded and/or deployed using a compliant balloon (e.g. using low pressure). A potential benefit of structure deployment using a complaint balloon is a highly conformed stent shape to lumen geometry.

In some embodiments, a structure is expanded and/or deployed using a non-compliant balloon (e.g. using high pressure). A potential benefit of structure deployment using a non-compliant balloon is that the stent can be used to open and/or enlarge a lumen (e.g. a body lumen), according to the balloon size. Optionally, some amount of recoil (e.g., 10%, 20%, 30% or intermediate values) is designed into the stent itself, by selecting a suitable match between SM and polymer hysteresis and applied forces and stent design. In other embodiments, recoil is substantially eliminated by such suitable selection.

Figure 8B:
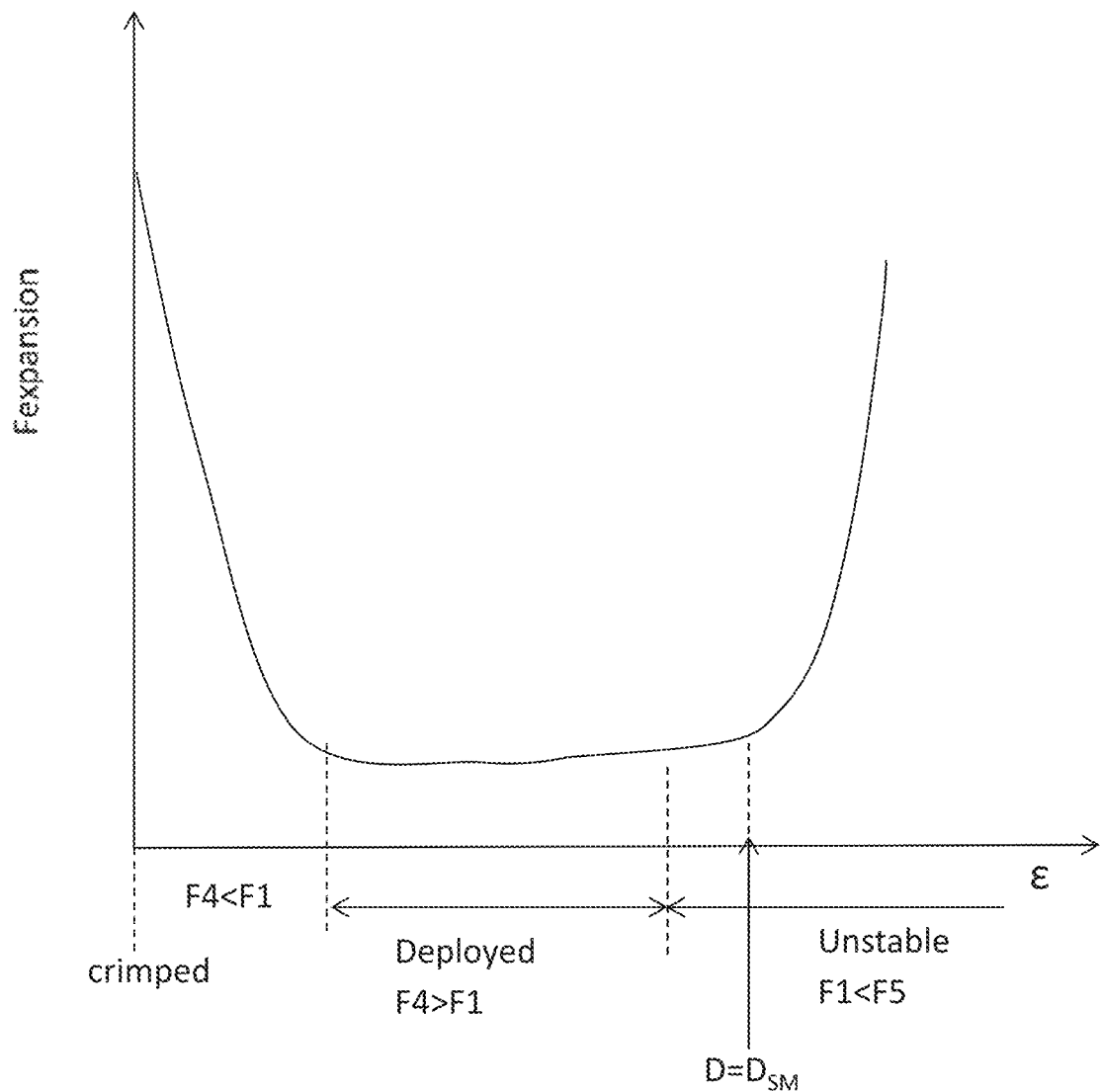
FIG. 8B presents a plot of applied expansion force, Fexpansion, with strain, $\varepsilon$, for a composite structure, according to some embodiments of the invention.

FIG. 8B presents a plot of applied expansion force, Fexpansion, with strain, ε, for a composite structure, according to some embodiments of the invention.

In some embodiments, Fexpansion is higher between crimped (ε=0) and deployed configurations where F4>F1.

In some embodiments, Fexpansion is fairly constant between deployed diameters. In some embodiments, Fexpansion increases (e.g. slightly) between deployed diameters, for example, as the force required to expand the polymer portion, F4, increases with structure diameter. In some embodiments, Fexpansion goes up and down, but within a desired range (e.g., of low force values).

In some embodiments, Fexpansion rises above SM portion relaxed strain, where structure diameter=$D_{SM}$.

In some embodiments, the structure is unstable below D=$D_{SM}$, for example, when the SM portion diameter approaches $D_{SM}$, F1 reduces. Once F1<F5 the structure is unstable and collapses, under the polymer portion relaxation force, F5.

Figure 8C:
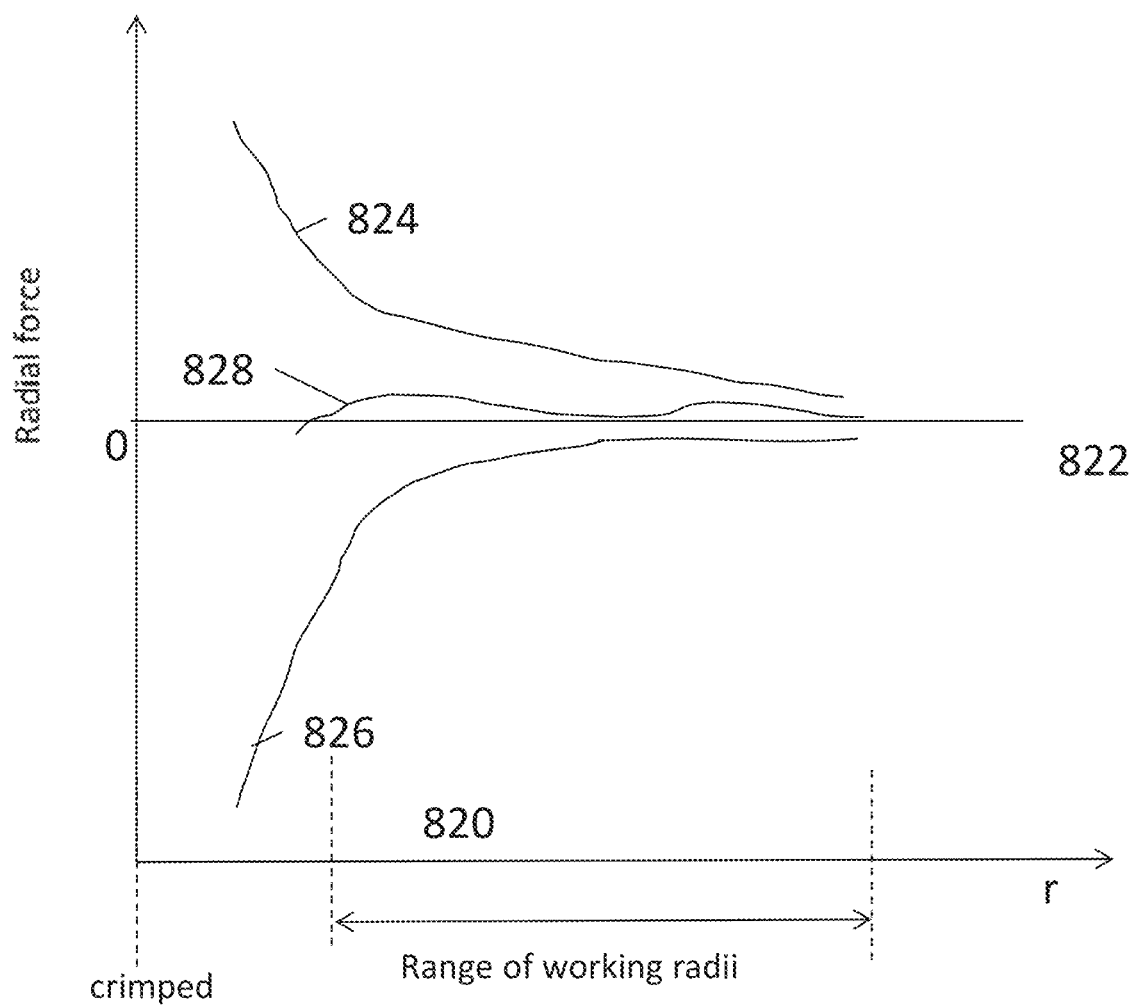
FIG. 8C is a chart showing the balancing between a force of expansion applied by a SM portion and a force of contraction applied by a second portion, in accordance with some embodiments of the invention.

FIG. 8C is a chart showing the balancing between a force of expansion applied by a SM portion and a force of contraction applied by a second portion, in accordance with an exemplary embodiment of the invention. In an exemplary embodiment of the invention, various behaviors of force applied by the stent and/or forces resisted by the stent can be achieved by varying the stent (or other structure) parameters.

In FIG. 8C, magnitude indicates size of force and sign, its direction. In a schematic case, for a range of working diameters 820, it is desirable that a total applied force (828) by the stent is close to zero (822). When force 826 is positive, this means that the stent tends to expand on its own. As can be seen, any such tendency is much smaller than the tendency which would be provided if only the SM portion existed (force 824). This is due to the counteracting effect of force 826 applied by the second portion. In design, one may, for example, select a desired range for force 828 and/or a desired range of diameters 820, and proceed to design/select stent portions that have force graphs which when combined yield the desired result. In some cases, one or both of force graphs 824 and 826 is given and only other parts may be modified.

Referring specifically to force graph 824, the magnitude of the force can be modified, for example, using strain effect as described above, using more or less material and/or different strength of SM portion design. The range of diameters over which force is applied in a positive way can depend, for example, on the relaxed diameter selected for "memory". The shape of the line can depend on the actual geometry of the stent SM portion. For example, diamond-type designs apply different amounts of force at different states of deformation, due to the angle between the struts (when the deformation is at the angle). The shapes of such force charts are known for a wide range of shapes and one can choose a shape according to a desired shape of graph. In an exemplary embodiment of the invention, the graphs (designs) are selected according to an expected amount of strain, or vice versa—strain is selected in order to provide the desired shape of graph. Further, by providing a composite design (e.g., two sets of deforming shapes, each with different strength and/or memory), graph 824 can be an overlay of two such graphs and be, for example, non-monotonic. Such selections can also be made for the second portion. In general, if the design of the two portions is different, the shape of 826 and 824 will not be mirror images of each other.

Such selection can be, for example, manual. Alternatively, modeling software (e.g., numerical simulation, such as FEA and/or other numerical methods) can be used to select matching structures and/or parameters that meet a desired result.

Force 828 need not be monotonic. His may result in there being several "sweet spots", diameters that are easier to achieve by expansion.

It is also noted that force 828 may be non-zero (though generally as small as desired) or even somewhat negative. In an exemplary embodiment of the invention, the stent is stable in diameter due to one or more of the following considerations:

First, the forces shown are not pure forces and are generated in reaction to the forces applied to the parts of the stent. This means that the small amount of hysteresis, for example, in the second portion, may be enough to resist changes in diameter due to small apparent forces 828.

Second, the blood vessel (or other lumen) may be allowed to apply some resisting force. Generally, in many lumens some such force is desirable to assist in anchoring the stent in the lumen (e.g., by friction or embedding and/or to allow the stent to react to slow and/or fast changes in lumen diameter). For example, the force may be on the order of 30%, 20%, 10% or less or intermediate percentages of the force applied by the SM portion alone.

Third, the stent may include a third (or more) portion which exhibits plastic deformation, resistance to which deformation supplied the force which zeros force 826. Optionally, the stent is not formed of more than 5, optionally 4, 3 or 2 different materials and/or materials with different treatment.

FIG. 8C does not pertain to what happens to force 828 outside range 820. Depending on the properties selected for forces 824 and 826, this may cause expansion or self-crimping of stent at low radiuses and/or at high radiuses.

Exemplary Deployed Configuration

In some embodiments, structure deployed configurations include a range of diameters less than $D_{SM}$. In some embodiments, (for example, because the diameter is less than $D_{SM}$), in deployed configurations, the SM portion is under a low level of strain, for example, a strain $\varepsilon_2$. In some embodiments, deployed strains are 1-4%. In some embodiments, a range of deployed structure diameters is 5-12 mm.

Referring to FIG. 6, when the SM portion is under strain $\varepsilon_2$, unloading (expanding) of the SM portion follows curve $f_1'(A_s')$. Loading of the SM portion follows curve F2. Unloading or relaxing of the polymer portion follows curve F5 and loading or extension of the polymer portion follows F4.

Figure 9A:
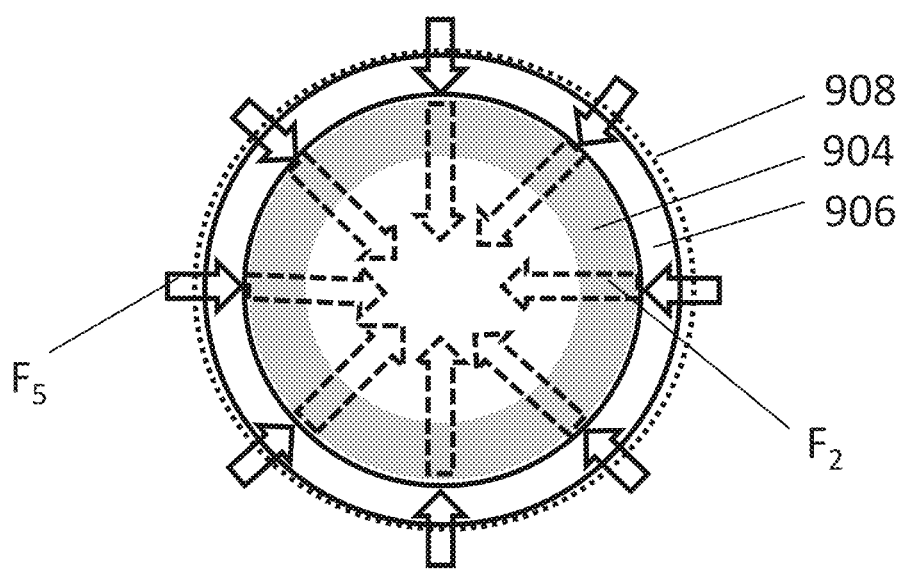
FIG. 9A is a is a simplified schematic cross sectional view of a structure in a deployed configuration, according to some embodiments of the invention and forces showing a contracting force balance.

In some embodiments, in deployed configurations, a force equilibrium or balance prevents the structure from collapsing, closing radially and/or crimping. FIG. 9A is a simplified schematic cross sectional view of a structure in a deployed configuration, according to some embodiments of the invention. In some embodiments, the balance is between the relaxation force F5 of the second portion 906, which is smaller than the loading force required to collapse or crimp the SM portion 904, F5<F2.

Figure 10:
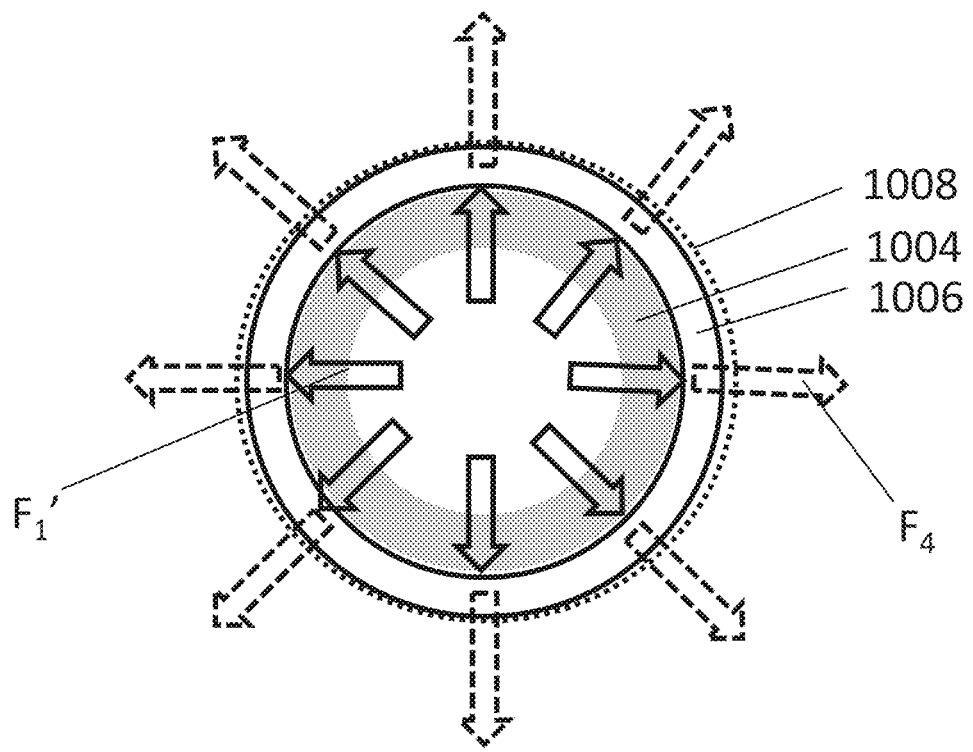
FIG. 10 is a simplified schematic cross sectional view of a structure in a deployed configuration, according to some embodiments of the invention and forces showing an expanding force balance.

In some embodiments, in deployed configurations, a force equilibrium or balance prevents the structure from expanding. FIG. 10 is a simplified schematic cross sectional view of a structure in a deployed configuration, according to some embodiments of the invention. In some embodiments, the balance is between the radially expanding force of a SM 1004 portion F1', which is smaller than the force required to expand F4 a second portion 1006.

In some embodiments, in a deployed configuration, a structure exerts substantially zero outwards force on a lumen. F1'−F4~0. In some embodiments F4 is reactive to F1', so it comes exactly to same value as F1' (potentially it can be larger).

In some embodiments, there are a wide range of deployed configurations, (e.g. deployed diameters) corresponding with a wide range of stable or balanced strains £ (shown on FIG. 6) where F1'<=F4 and F2>=F5.

Exemplary Crimp Resistance

In some embodiments, the structure, in a deployed configuration, is resistant to crimping and or closing. In some embodiments, for example, if the structure is circular in cross section, the structure has radial resistance to crimping. In other structures or sub-structures, such as a beam, crimp resistance is a resistance to bending and/or torsion.

Referring to FIG. 6, although forces required to radially compress or crimp the polymer portion is relatively low, F5, forces required to radially compress or crimp the SM portion are large, F2. Referring to FIG. 9A, a minimum force required to close or crimp the structure is Fcrimp=F2−F5.

In some embodiments, a force resisting radial collapsing, radial resistance, is substantially constant in structure deployed configurations (e.g., for example, selected using the methodology of FIG. 8C). In some embodiments, a force resisting radial collapsing increases with radial collapsing (decreases with strain), for example, because of decreasing F5 with strain.

Figure 9B:
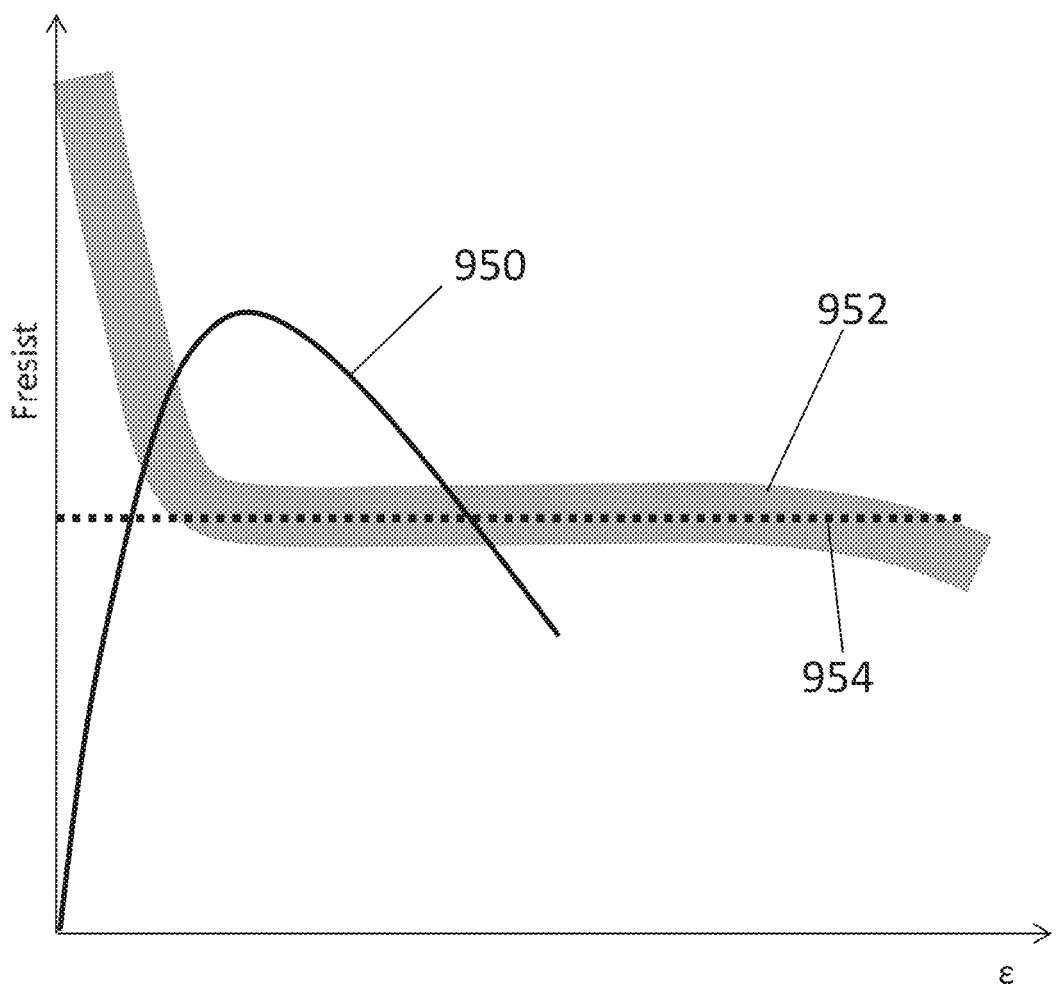
FIG. 9B presents plots of crush resistance (Fresist) with strain $\varepsilon$, according to some embodiments of the invention.

FIG. 9B presents plots of crimp resistance, Fresist, with strain, $\varepsilon$, according to some embodiments of the invention. For example, if the structure is circular in cross section, $\varepsilon = \Delta D/D$, where $\Delta D$ is the change in diameter of the structure where D is the diameter of the structure in the crimped configuration.

Schematically illustrated in FIG. 9B are a radial resistance of steel 950, a radial resistance of structures and/or stents 952, according to some embodiments of the invention and an ideal radial resistance 954 (constant radial resistance for all diameters). In some embodiments, at $\varepsilon=0$ and the structure is crimped, Fresist is at a maximum. As strain increases to deployed diameters, Fresist falls to a plateau, dropping after the plateau. In an exemplary embodiment of the invention, various parameters of the stent, for example, properties of the SM portion, properties of the second portion and/or a match between them, are selected to achieve a desired shape and/or length of the plateau and/or a desired small angle of inclination (and/or range of variance) thereof.

Exemplary Crush Resistance

Figure 11:
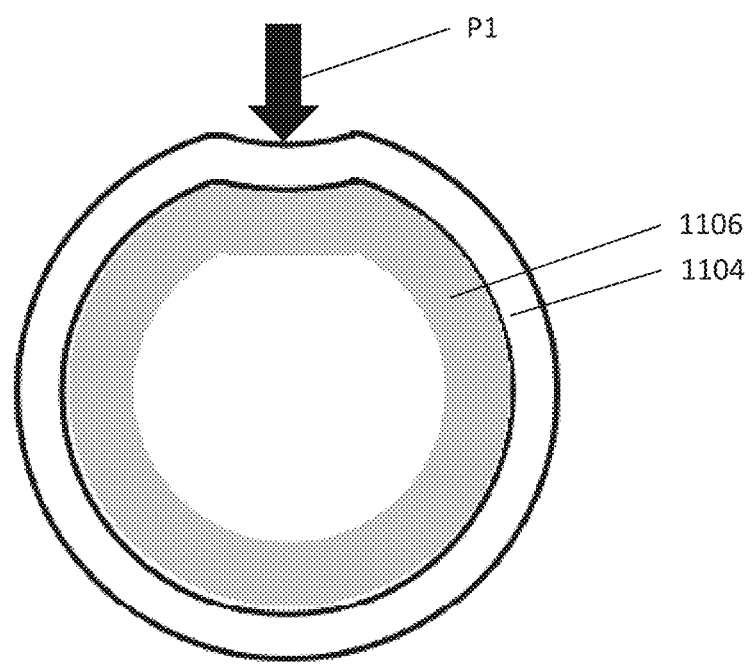
FIG. 11 is a simplified schematic cross section of a structure in a deployed configuration, undergoing a local deformation, according to some embodiments of the invention.

In some embodiments, the structure has low resistance to a local pressure applied to the structure. FIG. 11 is a simplified schematic cross section of a structure in a deployed configuration, undergoing a local deformation, according to some embodiments of the invention. In an exemplary embodiment of the invention, a local deformation is one applied to less than 30%, 20%, 10% or other percentage, for example intermediate, as desired, of the diameter of the structure. In an exemplary embodiment of the invention, during crushing only the diameter changes and not the circumference of the structure. Possibly, this avoids a change in force applied by the polymer layer, while still affecting the force applied by the SM portion.

For example, in some embodiments, local pressure P1, applied to the structure corresponds with low strain on the SM portion. In some embodiments, a local pressure corresponds with low strain on the SM portion. In some embodiments, referring to FIG. 6, a local crushing pressure is approximately ⅓ of F2. In some embodiments, a local crushing pressure results in strains of approximately 0.1-1.5%, or less, for example, about 1% corresponding to classic elastic (austenite) SM portion reactive force (F2 before the plateau). In some embodiments, the reactive force (to the crushing force) of the polymer, F5, is almost zero, corresponding to a small strain of the polymer portion. Once local pressure P1 is removed, for example, as the polymer portion has not significantly changed in circumference, the SM portion returns to a pre-deformation deployed configuration.

In an exemplary embodiment of the invention, various parameters of the stent may be varied in order to achieve a desired crush resistance. For example, the SM portion design may be changed to make it to make it stiffer or use thicker SM material, giving a higher crush resistance. In such a case poly design may be changed to restore balance of forces.

Exemplary Second Portion, Additional Portions

In some embodiments, the second portion is a high recoil elastic (e.g. a high recoil polymer). In some embodiments, the second portion is extended such that it applies sufficient contracting force to balance the SM portion expanding force. In some embodiments, for example, in deployed configurations, the second portion is elastically extended from a relaxed diameter to, 100-600%, 200-500%, 300-400%.

In some embodiments, the second portion is elastic, including elastic hysteresis, as described above, where F4≠F5, for example, there being a difference of at least 10% 50%, 100%, 300% or intermediate percentages between F4 and F5. In some embodiments, the second portion is elastic, where F4=F5, for example, there being less than 10%, 5%, 3% or intermediate percentage of difference between F4 and F5.

In some embodiments, the second portion is shape memory as well, however, this may limit its range of expansion.

Optionally, in some embodiments, the second portion, and/or an additional portion is plastic, for example, plastically deformed during deployment e.g. gold. In embodiments where the second portion is plastically deformed during deployment, the second portion resists expansion of the SM portion.

In some embodiments, a structure includes more than two portions.

For example, in some embodiments, a structure includes three portions including a SM portion, a polymer portion with high recoil and an additional portion and/or layer, which is plastically deformed by deployment.

For example, the structure is deployed, plastically deforming an additional outer portion, upon a temperature change the SM portion and polymer portion self-crimp, for example, leaving the outer portion within the lumen.

For example, the structure is deployed, plastically deforming an additional portion disposed within said elastic second portion, the plastically deforming portion for example providing additional resistance to expansion (e.g. to increase control of expansion).

In an exemplary embodiment of the invention, the portions are arranged as layers, however, this need not be the case and depending on the mechanical coupling the two or more portions may be interleaved or provided side by side.

Exemplary Outward Radial Force (ORF)

In some embodiments, for example, as the radially expanding force of the SM material and the radially contracting force of the polymer are balanced, an outward radial force (ORF) of the structure outwards, when the structure is in a deployed configuration (e.g. a force outwards on the lumen from the deployed structure) is substantially zero (see also FIG. 8C).

Figure 12:
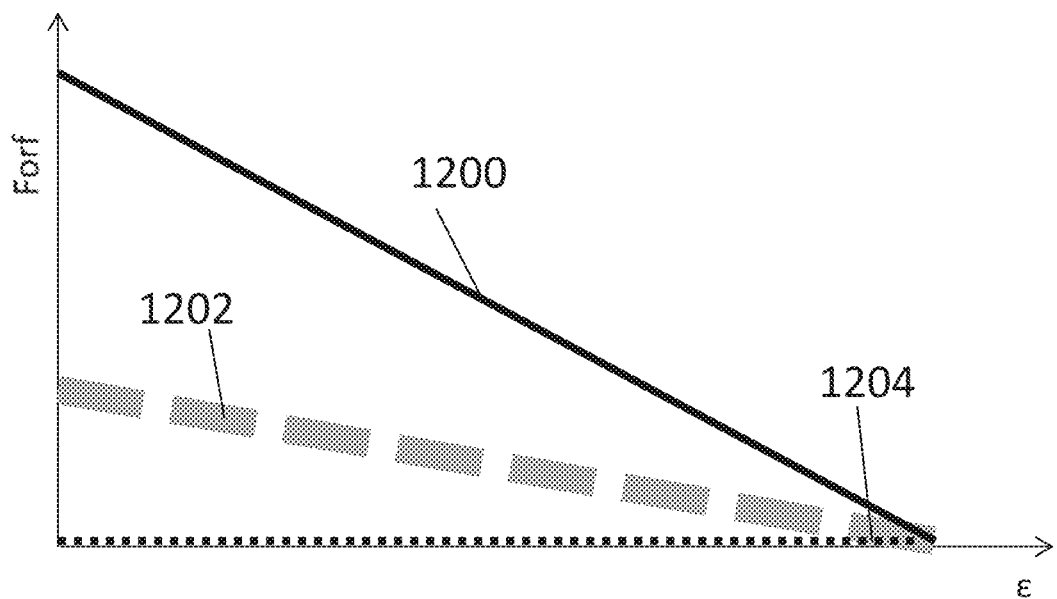
FIG. 12 presents plots of outwards force from the structure (pushing force, Fpush) with strain $\varepsilon$, according to some embodiments of the invention.

FIG. 12 presents plots of outwards force from the structure, Forf, with strain ε. For example, if the structure is circular in cross section, $\varepsilon = \Delta D/D$, where $\Delta D$ is the change in diameter of the structure and D is the diameter of the structure in the crimped configuration.

Schematically plotted in FIG. 12 are; a pushing force of stents of the art 1200, a pushing force of structures and/or stents 1202 according to some embodiments of the invention and an ideal pushing force 1204 (e.g. zero pushing force for all stent diameters).

In some embodiments, Forf is highest in the crimped configuration, where strain, ε=0. In some embodiments, as the structure is expanded (or independently expands), Forf decreases, until Forf=0 at a strain where D approaches $D_{SM}$.

In some embodiments, Forf is minimal at $D=D_{SM}$, for example, due to selection of the polymer portion contracting force.

In some embodiments, Forf is about 0.1N when ε=50%. This is in comparison with Forf=2-5N at ε=50% of self-expanding biliary or SFA stents of the art.

Exemplary Self-Crimping

In some embodiments, temperature related material characteristics of the SM portion are used to close or crimp the structure from a deployed configuration. Referring back to FIG. 5, in a deployed configuration the SM portion is superelastic, upon cooling below $A_s'$, for example, by spraying or washing the structure with cold saline solution, or otherwise cooling the structure directly or indirectly (e.g., cooling surrounding tissue and/or fluids) the SM material transforms to an easily deformable martensite crystal structure. At this point, the second portion can collapse the structure and meet little resistance.

Figure 13:
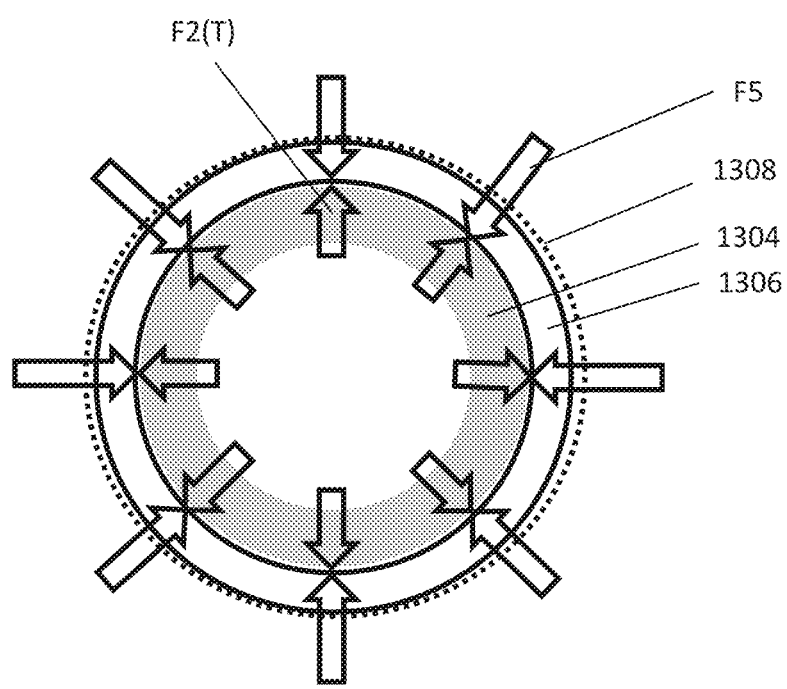
FIG. 13 is a simplified schematic cross section of a structure in a deployed configuration, and forces on the structure upon a temperature change, in accordance with some embodiments of the invention.

FIG. 13 is a simplified schematic cross section of a structure in a deployed configuration, and forces on the structure upon a temperature change. In some embodiments, for example, at a low temperature (e.g. 10° C.), the radial resistance force of the SM portion, which is dependent on temperature, F2(T) is less than the relaxation force F5(T) of the polymer and the structure collapses.

In some embodiments, self-crimping is initiated without changing the temperature of the structure. In some embodiments, the structure is over-expanded (e.g. to above $D_{SM}$) such that the SM portion provides a low or substantially no radially resisting force. The structure is no longer balanced, and the structure closes or collapses under the polymer relaxation force F5. The amount of over expansion may depend on the design. For example, 10%-20% may be sufficient for some designs, which for some normally-closed designs an increase of 500-700% may be needed. In an exemplary embodiment of the invention, the diameter at which self-crimping occurs is determined at design time and is, for example, between 110% and 600%, for example, between 130% and 200% of the maximum stable deployed diameter.

In some embodiments, a self-crimped structure diameter is larger than a minimal crimped structure diameter. This may be for example, as, in some embodiments, the stent is crimped at high strain by external crimper corresponding to low SM portion expanding force and correspondingly a low crimped diameter. Whereas, in some embodiments, for example, the polymer relaxation force responsible self-crimping is lower than forces applied by an external crimper, so SM portion strain is lower than externally crimped strain, SM portion expansion force is higher, resulting in a larger diameter.

Exemplary Self-Deployment

In some embodiments, temperature related material characteristics of the SM portion are used to open or deploy the structure, optionally without applying external force to the structure. In some embodiments, the structure is heated (e.g. using heated saline, microwave heating) and at least a part of the SM portion transforms from martensite to austenite crystal structure. In some embodiments, the austenite SM includes a higher radially expanding force than the polymer expansion force F4 and the structure expands. In some embodiments, the structure, upon heating, self-expands or self-deploys to fill the lumen, in some embodiments, the structure expansion is stopped and/or limited by resistive forces of the lumen. In some embodiments, unlike self expanding stents of the art, as the structure cools (e.g. to body temperature) the outwards force of the structure on the lumen reduces as the SM portion transforms from austenite to superelastic behavior, until there is substantially no outwards force on the lumen, for example, as the SM radially expanding force is balanced by the polymer radially contracting force. In an exemplary embodiment of the invention, heating is provided in bursts so as to provide better control over expansion. For example, between 2 and 10, for example, between 3 and 5 bursts may be used to incrementally expand a structure.

Exemplary Two-Way Shape Memory

In some embodiments, a SM portion includes a two-way shape memory, for example of a type known in the art. As previously described, the first shape memory corresponds with $D_{SM}$. In some embodiments, a second shape memory is invoked upon cooling a crimped structure. In some embodiments, a structure crimps to a second shape memory structure diameter, the structure contracts on cooling to a second shape memory configuration. A potential benefit of two-way shape memory for self-crimping is a reduced structure crimped configuration size, for easy and safe insertion and/or removal of the structure.

Figure 14A:
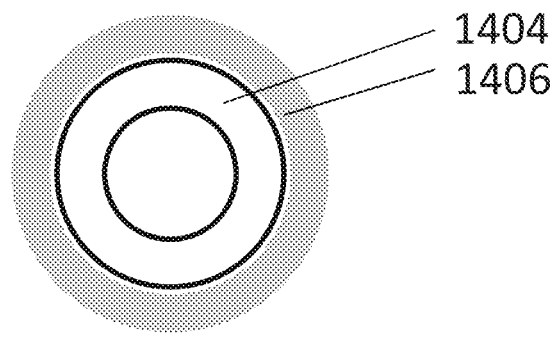
FIG. 14A is a simplified schematic cross section of a structure in a crimped configuration, according to some embodiments of the invention.

FIG. 14A is a simplified schematic cross section of a structure in a crimped configuration, according to some embodiments of the invention.

Figure 14B:
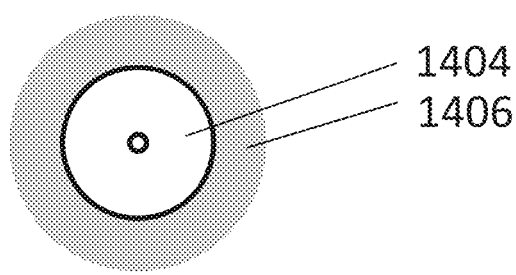
FIG. 14B is a simplified schematic cross section of the structure of FIG. 14A where the SM portion has two way shape memory structure in a crimped configuration, according to some embodiments of the invention.

FIG. 14B is a simplified schematic cross section of the structure of FIG. 14A where the SM portion has two way shape memory structure in a crimped configuration, according to some embodiments of the invention. The manufacture and construction of the SM portion and the second portion of the structures illustrated in FIG. 14A and FIG. 14B are optionally the same (e.g., material type, structure type, thickness and/or heat treatment). However, the SM portion illustrated in FIG. 14B has been set to have a second shape memory, of smaller diameter than the first shape memory. Upon cooling, the crimped structure diameter of the structure illustrated in 14B is smaller than a crimped structure diameter of the structure in FIG. 14A.

Exemplary Method of Use of the Structure

Figure 15:
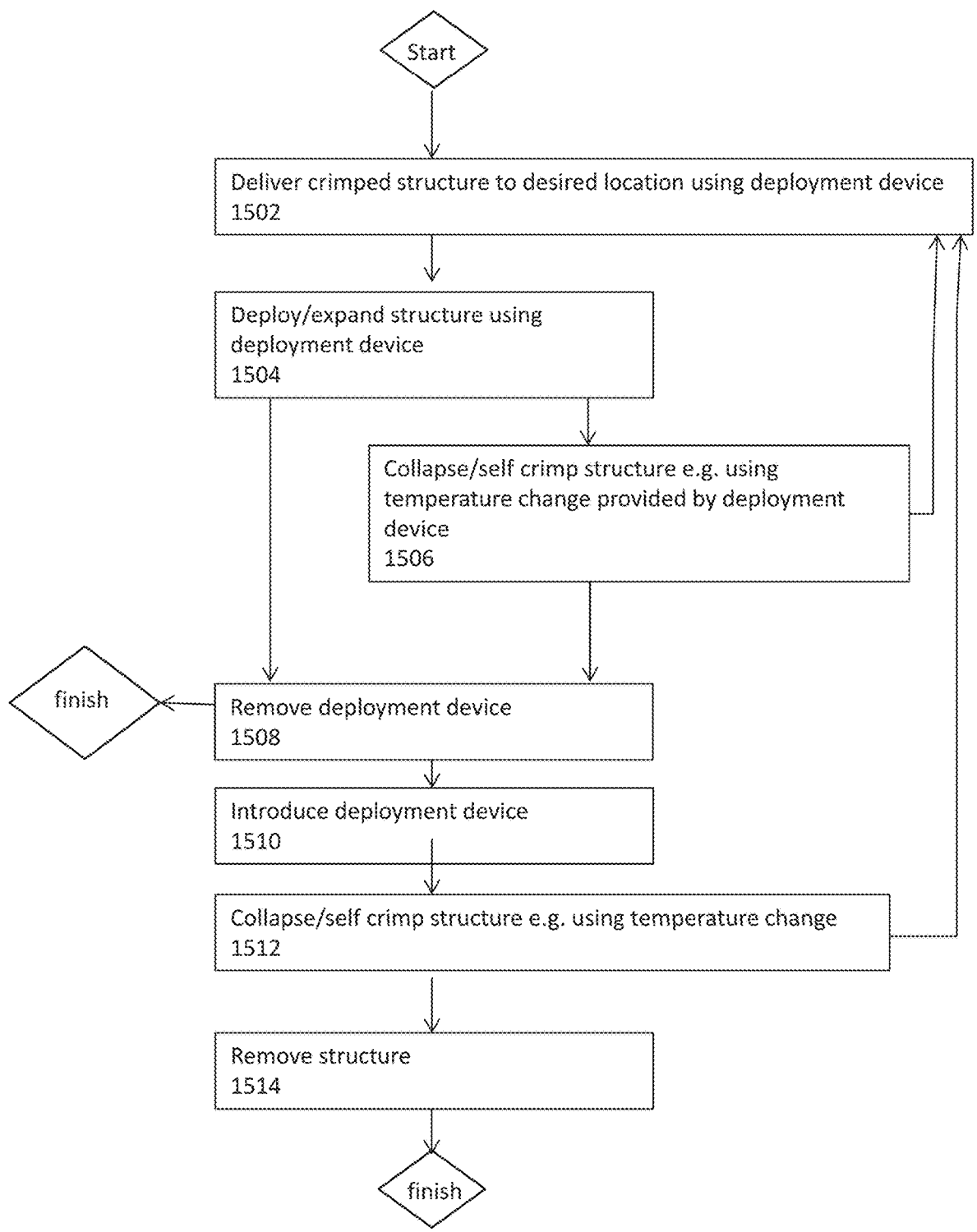
FIG. 15 is a flow diagram of methods of use of a structure, according to some embodiments of the invention.

FIG. 15 is a flowchart of an exemplary method of use of a structure, according to some embodiment of the invention. Crimp structure onto positioning device.

At 1502, the crimped structure is delivered to desired location using a deployment device (e.g., a balloon catheter on which the structure is mounted, optionally by direct crimping thereon. Optionally, manufacturing comprises self-crimping the stent unto the balloon, for example, using one of the method described herein above.). At 1504, the structure is deployed (expanded), using deployment device. For example, in some embodiments, the deployment device manually expands the structure (e.g. by filling and/or inflating a balloon). Alternatively, or additionally, in some embodiments, the deployment device expands/deploys the device by initiating a temperature change (e.g. using heated/cooled saline).

Optionally, at, 1506 the structure is collapsed or self-crimped, e.g. by a temperature change initiated by the deployment device. Optionally, at 1502, the structure is delivered to a desired location, e.g. repositioned before, at 1504, being re-deployed. Optionally, at, 1508, the deployment device is removed.

Optionally, for example, after a time duration, at 1510 a deployment device is reintroduced, at 1512, the structure is collapsed or self-crimped, e.g. by a temperature change initiated by the deployment device and, at 1514 the structure is removed (e.g. on deployment device).

In an exemplary embodiment of the invention, during deployment, the structure is expanded and crimped multiple times, for example, expanded n a first location and based on an indication location is incorrect (anatomical image and/or functional effect), the stent is collapsed and repositioned. This may be especially useful for devices such as heart valves or aortic-arch stents or connecting stent grafts where exact positioning is often critical, yet not easy in a beating heart and/or at the end of a catheter. In an exemplary embodiment of the invention, the structure is expanded (and collapsed as needed in between) at least twice, for example, up to, for example, 3, 5, 10 or more or intermediate number times.

Exemplary Structures

Circumferential Segments

Figure 16:
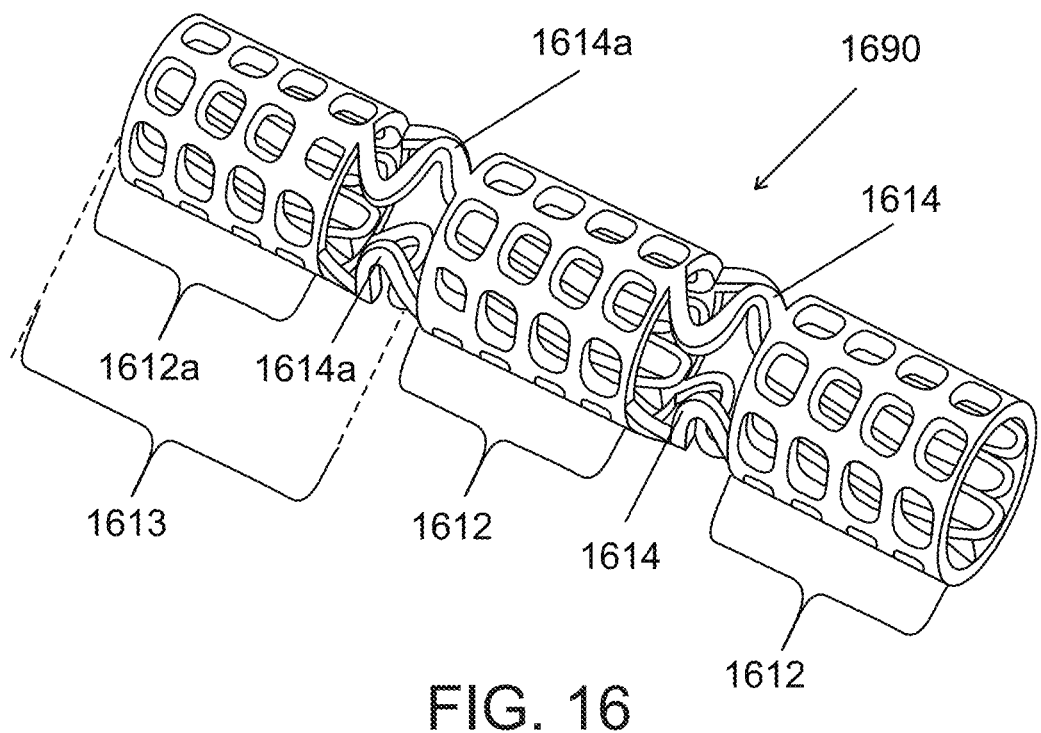
FIG. 16 is a simplified schematic of an exemplary structure in a crimped configuration, according to some embodiments of the invention.
Figure 17:
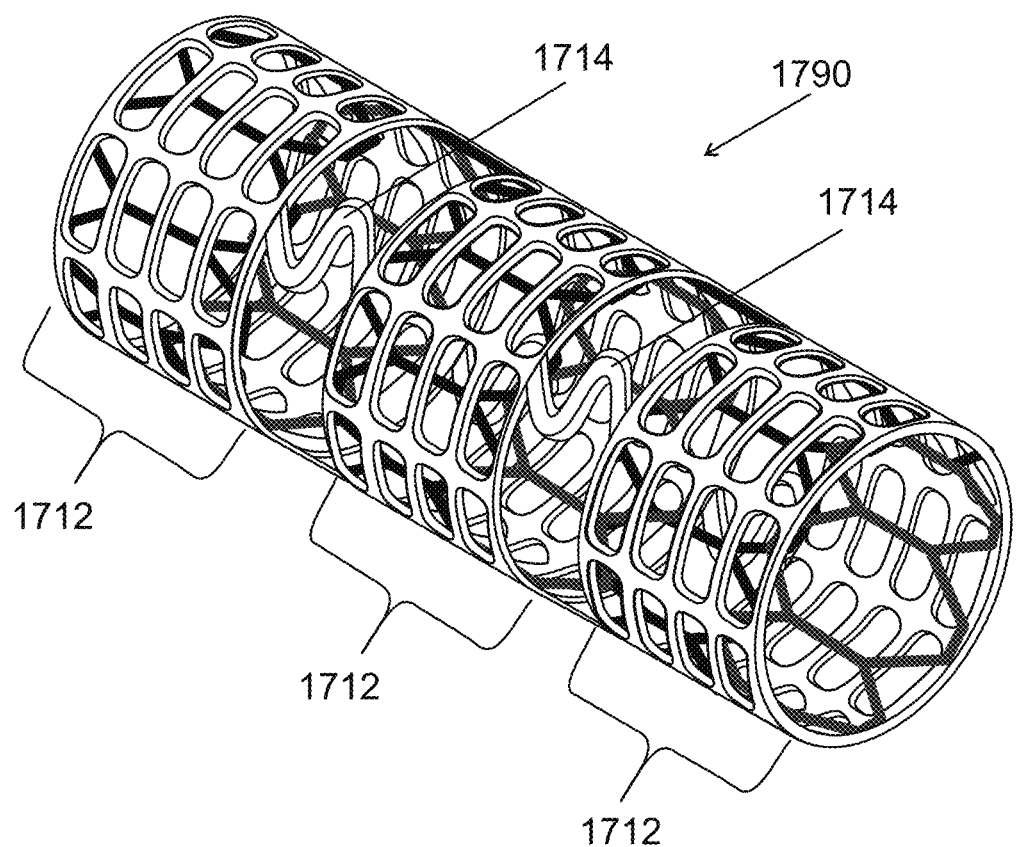
FIG. 17 is a simplified schematic of an exemplary structure in a deployed configuration, according to some embodiments of the invention.

FIG. 16 is a simplified schematic side view of a crimped structure 1690, according to some embodiments of the invention. FIG. 17 is a simplified schematic side view of a deployed structure 1790, generally corresponding to structure 1690, according to some embodiments of the invention.

In some embodiments, stent 1690, 1790, includes more than one segment. In some embodiments, segments are circumferential segments 1612, 1712. In some embodiments, circumferential segments 1612, 1712 are coupled by axial connectors 1614, 1714. In other embodiments, segments may have other shapes, such as patches, axial sections and/or sections with both axial and partial circumferential extent and/or combinations of any of the above. Also as noted below, structures using the principles described herein can be non-tubular, for example, ring shaped, helical, beam shaped (e.g., straight or curved) and/or spherical or ellipsoid-like.

In FIG. 16, FIG. 17, FIG. 18, FIG. 19, FIG. 20, and FIG. 21 SM material is illustrated as black (inner layer, generally thinner) and polymer material, is illustrated as grey (outer layer, generally more robust). In some embodiments of the invention, the structures do not include both a SM layer and a second portion layer, for example utilizing materials and designs as known in the art, other than segmented design and connector design as described herein. It is noted, however, that there is a synergy between these designs and the use of a two portion stent with a SM portion and a second portion.

In some embodiments, a connector length compensates for a change in segment length (e.g. change in axial length of section 1612), for example, maintaining an overall structure length (e.g. upon expanding or contracting the structure). For example, if an axial length of segment 1612a reduces (e.g. upon deployment) in some embodiments, connectors 1614a extend such that an axial length 1613 remains the same. Optionally, this extension if "programmed" into the connector, as a shape memory. Optionally or alternatively, this modification is imposed by a balloon or other deployment structure restraining axial length changing of the device. Optionally, the deployment structure includes a plurality of elements, such as hooks or rings which engage structure 1690 and resist axial contracting and/or elongation thereof, during deployment.

Optionally, at least two segments each include a different enclosed geometry and/or area, optionally in a crimped and/or deployed configuration.

Optionally or alternatively, at least two different segments include and/or are formed of different materials and/or have different geometries and/or different axial lengths.

In some embodiments, one or more connectors 1614, 1714 include polymer only. In some embodiments, a potential advantage of polymer only connector/s, is a flexible connection between segments, for example, providing high stent flexibility (e.g. for deployment) and/or high conformability (e.g. to a lumen). A potential advantage of a stent with high conformability is a low movement of the deployed stent within the lumen (migration resistance) and a corresponding low re-stenosis rate.

In some embodiments, one or more connectors 1614, 1714 include SM material only. In some embodiments, one or more connectors include SM material and polymer.

In some embodiments, one or more segment includes a different design, for example, for providing different support in different stent areas. In some embodiments, one or more segment has a SM portion with a different relaxed diameter, $D_{SM}$. In some embodiments, one or more segment has a polymer portion with a different relaxed diameter, $D_{poly}$. In some embodiments, one or more segment has a different pattern or cell structure for the SM portion and/or the polymer portion. For example, one or more segment including SM portion with a zigzag structure and one or more segment including a flattened eight sided shape.

Figure 18:
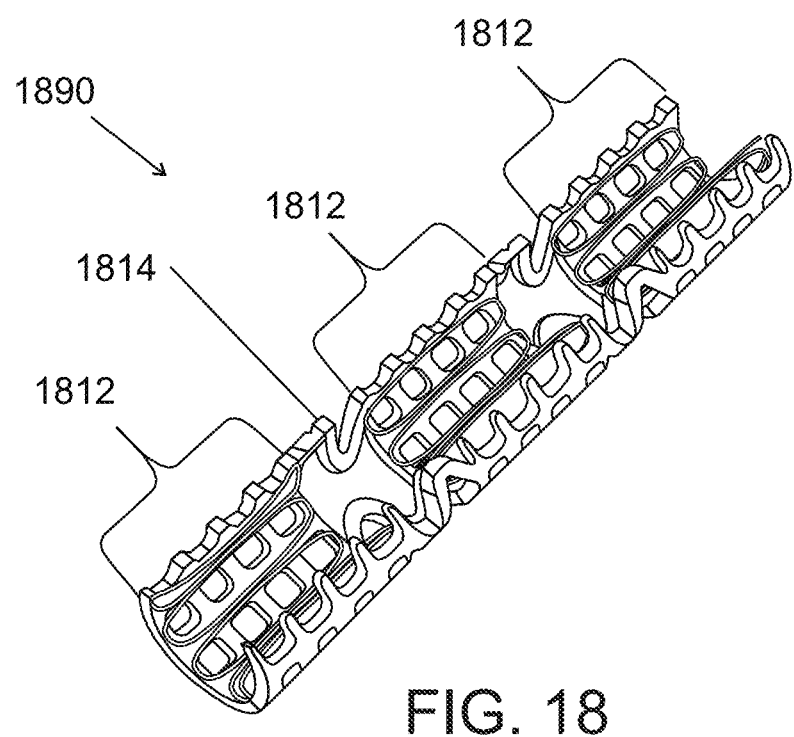
FIG. 18 is a simplified schematic cross section along a length of an exemplary structure in a crimped configuration, according to some embodiments of the invention.

FIG. 18 is a simplified schematic cross section along a length of an exemplary structure 1890 in a crimped configuration, according to some embodiments of the invention. As can be seen, optionally the SM layer has less material and/or lower surface coverage (and/or different design) than the polymer layer. Optionally, the stenting (or other structural) function is provided by the polymer layer with the SM portion acting to provide structural stability as described herein. This may be applied also in non-segmented stents.

Figure 19:
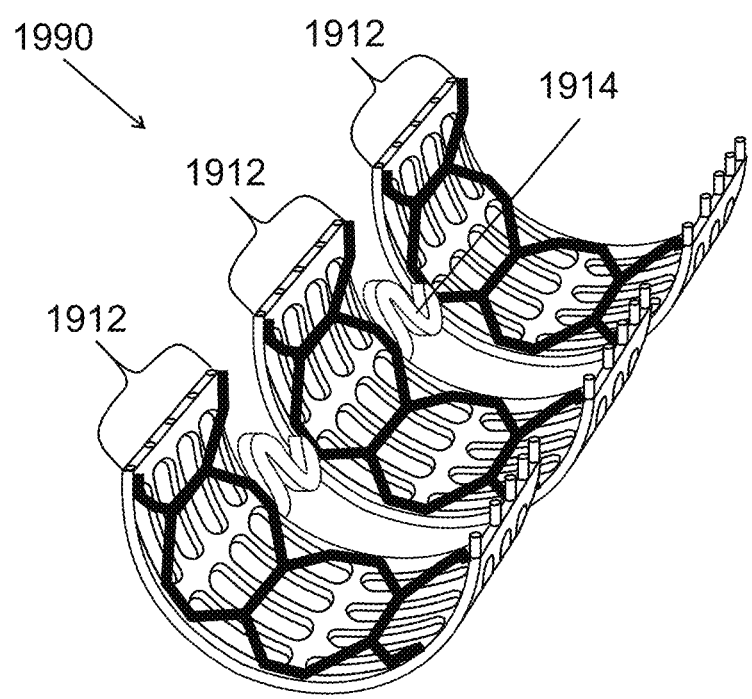
FIG. 19 is a simplified schematic cross section along a length of an exemplary structure in a deployed configuration, according to some embodiments of the invention.

FIG. 19 is a simplified schematic cross section along a length of an exemplary structure 1990 in a deployed configuration, according to some embodiments of the invention.

Figure 20:
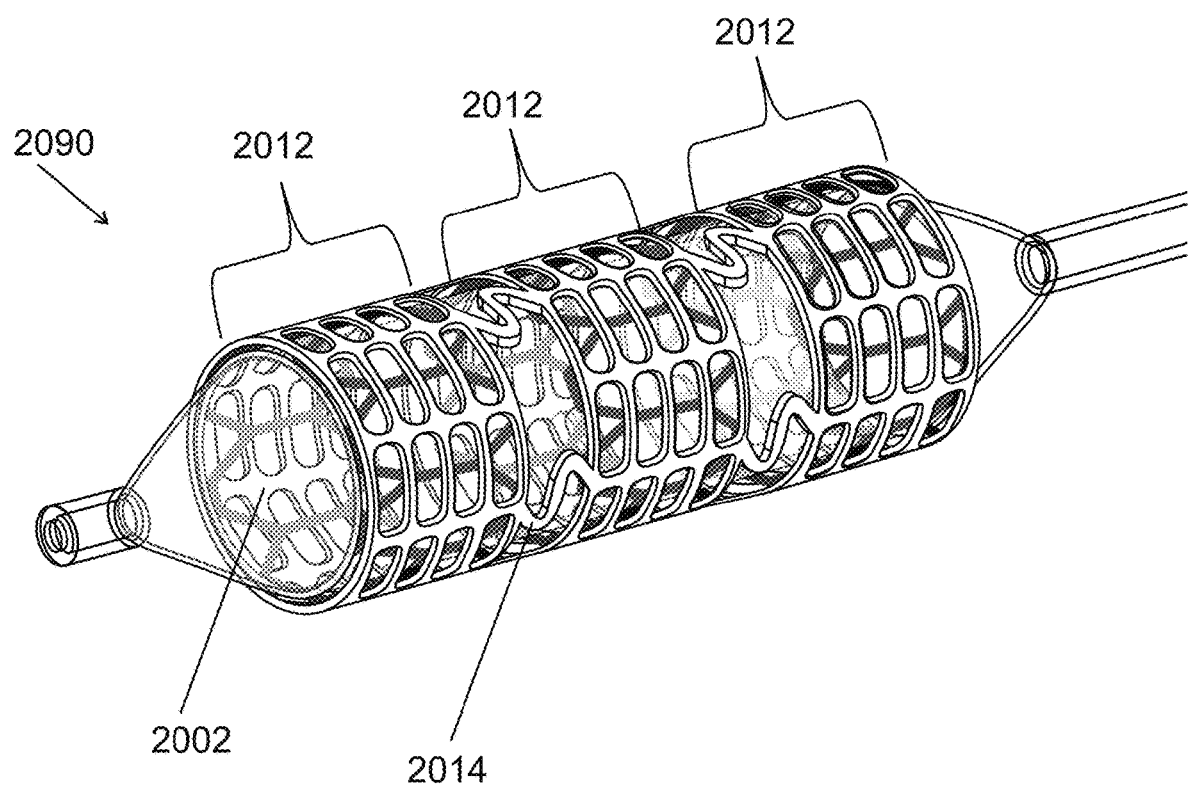
FIG. 20 is a simplified schematic side view of an exemplary structure in a deployed configuration, on a deployment device, according to some embodiments of the invention.

FIG. 20 is a simplified schematic side view of an exemplary structure 2090 in a deployed configuration, on a deployment device 2002 (e.g., a balloon catheter), according to some embodiments of the invention.

In some embodiments, as illustrated in FIG. 16, FIG. 17, FIG. 18, FIG. 19 and FIG. 20 segments include a flattened eight sided shape, where the octagon flattens in the crimped configuration and expands in the deployed configuration. Other numbers of sides and/or geometries may be used as well, in other embodiments.

In some embodiments, deployment device 2002 includes one or more stopper elements (e.g. a distal and a proximal stopper, e.g., at the end of the stent or past the end of the stent, not shown), which optionally engage the stent and prevent axial movement thereof. Optionally, the stoppers are in the form of balloons. Optionally or alternatively, one or both of the stoppers are in the form of rings which abut the stent and/or in the form of a protruding element which engages the stent, e.g., between struts thereof/in an aperture thereof. In some embodiments, deployment device 2002 includes a catheter. In some embodiments, mounting is by placing the stent on the balloon, between the stoppers and cooling to evoke self-crimping, such that upon a temperature change the structure self-crimps over the catheter between the stoppers. In some embodiments, one or more stopper prevents the stent from sliding (e.g. off) the deployment device (e.g. upon removal of the device from the body (and/or insertion thereinto).

In some embodiments, a distal stopper (e.g. on the free end of the retrieving catheter) is a small low pressure balloon. In some embodiments the distal stopper balloon is deflated when the deployment device is inserted into a deployed stent and is inflated, for example, before pulling the deployment device out of the body (e.g. either before or after crimping).

In some embodiments, deployment device 2002 includes one or more side holes through which a liquid (e.g. saline), in some embodiments, is flushed e.g. to initiate a structure temperature change. In some embodiments, the side holes are situated between stoppers. In some embodiments, such flushing is provided within the balloon (e.g., cooling or heating its contents, e.g., using an internal or external (to body) heater). Optionally or alternatively, flushing is provided from a port (e.g., an overtube such a guide catheter) proximal to the stent.

Figure 21:
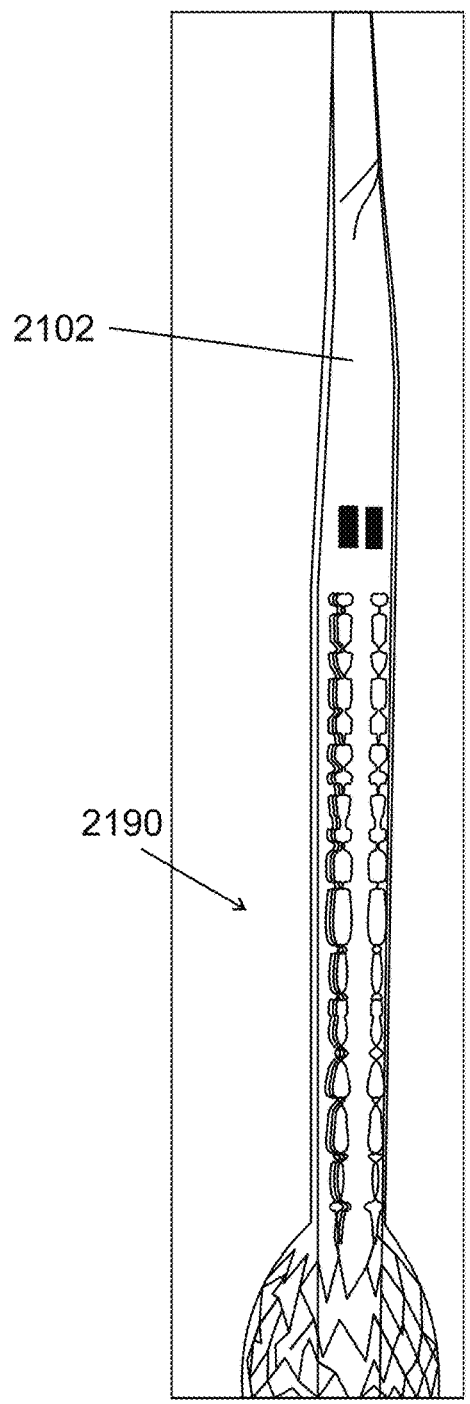
FIG. 21 is a photographic side view of an exemplary structure in a crimped configuration, on a deployment device, according to some embodiments of the invention.
Figure 22:
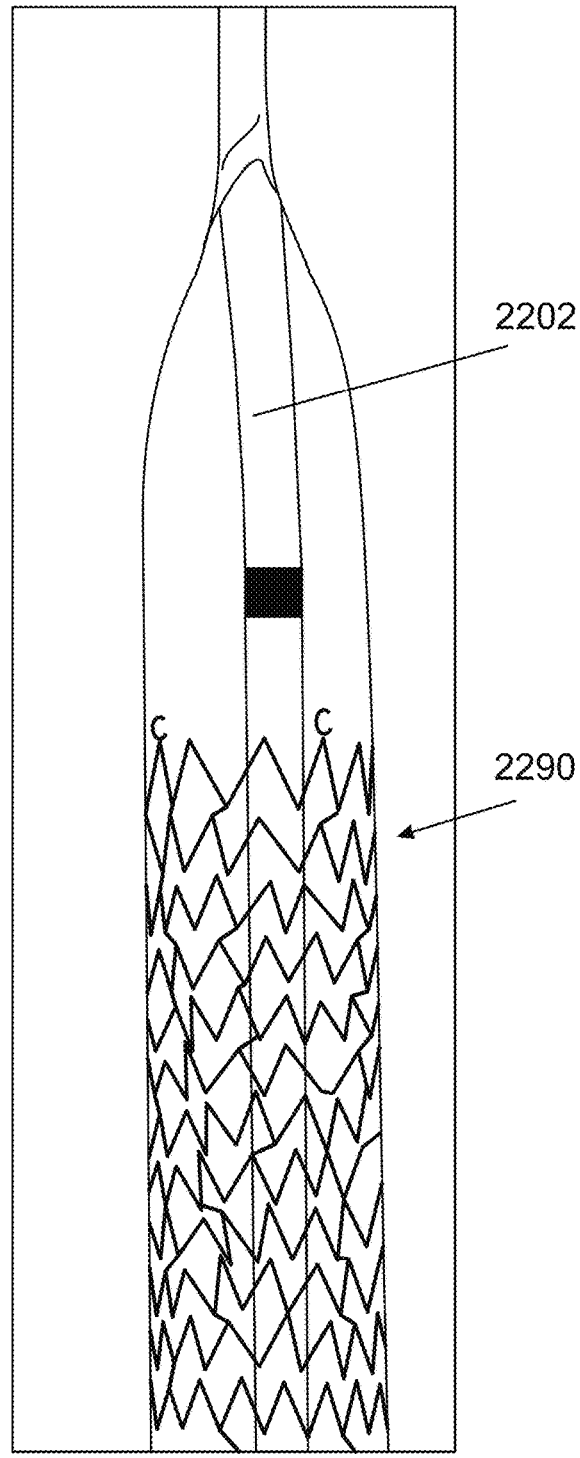
FIG. 22 is a photographic side view of the exemplary structure of FIG. 21 in a deployed configuration, on a deployment device, according to some embodiments of the invention.

In some embodiments, segments include a SM portion with folding zigzag structure. In some embodiments, closing of a stent is by bending at apexes of the zigzags. FIG. 21 is a photographic side view of a second exemplary structure 2190 in a crimped configuration, on a deployment device 2102, according to some embodiments of the invention. FIG. 22 is a photographic side view of the second exemplary structure 2290 in a deployed configuration, on a deployment device 2202, according to some embodiments of the invention. The embodiment illustrated in FIG. 21 and FIG. 22 includes a transparent polymer portion (not visible in the figures) which substantially covers (e.g. is cylindrical in shape) the SM portion, e.g. covering more than 80%, more than 90%, more than 95% or intermediate percentages of the SM portion. In some embodiments, a covering polymer portion includes small apertures.

Figure 38A:
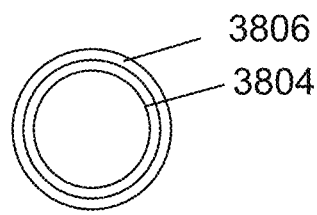
FIG. 38A is a simplified schematic front view of a crimped stent, according to some embodiments of the invention.
Figure 38B:
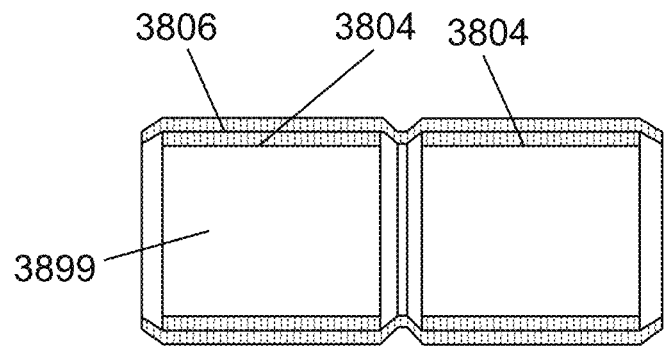
FIG. 38B is a simplified schematic axial cross section of a crimped stent, according to some embodiments of the invention.
Figure 38C:
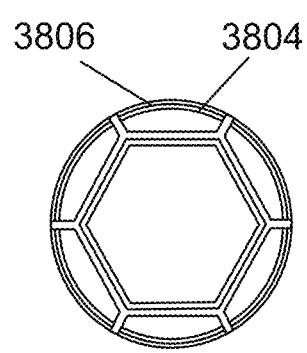
FIG. 38C is a simplified schematic front view of a deployed stent, according to some embodiments of the invention.
Figure 38D:
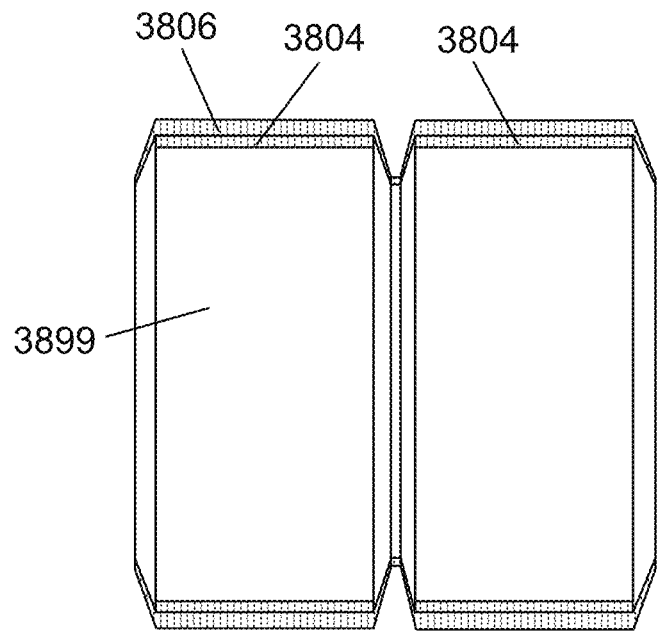
FIG. 38D is a simplified schematic axial cross section of a deployed stent, according to some embodiments of the invention.

In some embodiments, a structure includes more than one SM portion and a single second portion restraining and interconnecting the SM portions. FIG. 38A is a simplified schematic front view of a crimped stent, according to some embodiments of the invention. FIG. 38B is a simplified schematic axial cross section of a crimped stent, according to some embodiments of the invention. FIG. 38C is a simplified schematic front view of a deployed stent, according to some embodiments of the invention. FIG. 38D is a simplified schematic axial cross section of a deployed stent, according to some embodiments of the invention.

In some embodiments, parts of the second portion (e.g. connectors or a connecting sleeve) are not supported by a SM segment. In some embodiments unsupported second portion parts protrude into a structure lumen 3899. A potential benefit of unsupported second portion parts is reduction and/or elimination of SM segment axial movement within the structure lumen (e.g. by physically blocking movement). It should be noted that such axial migration prevent is possible even if there is only a single SM portion and a single polymer portion (e.g., design of FIGS. 38A-E), by the polymer portion radially contracting where it does not overlap the SM portion (e.g., at edges thereof and/or overlaying apertures therein) such that interference is created between said SM portion and said polymer portion. Optionally, the polymer portion extends a few mm or fractions thereof past the edge of said SM portion.

Figure 38E:
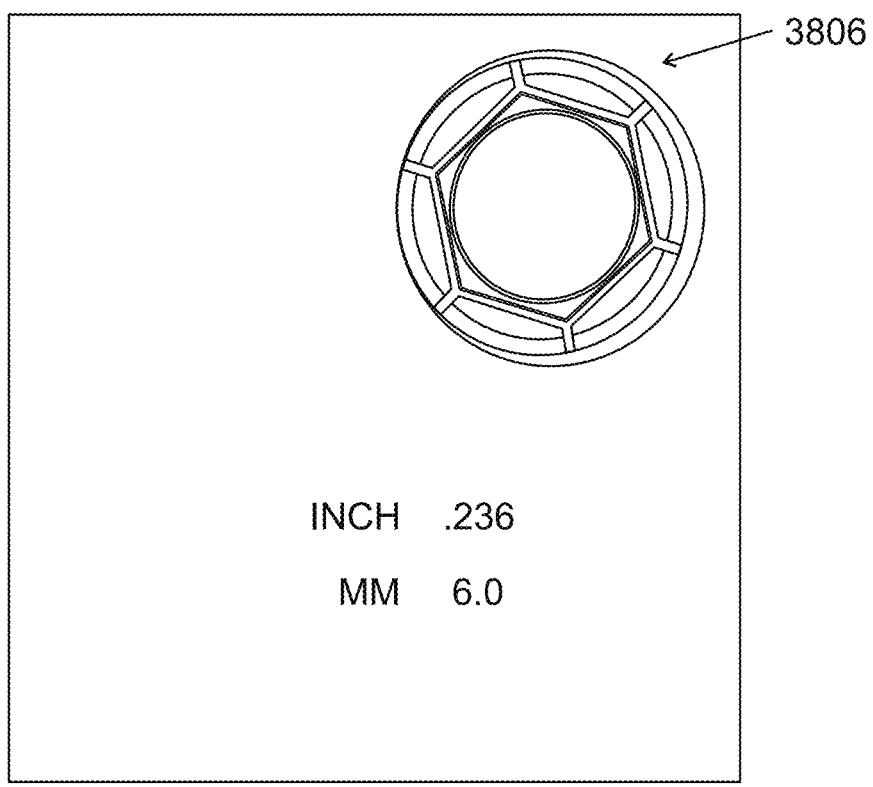
FIG. 38E is a photographic top view of an exemplary structure with a second portion protruding into a structure lumen, according to some embodiments of the invention.
Figure 39:
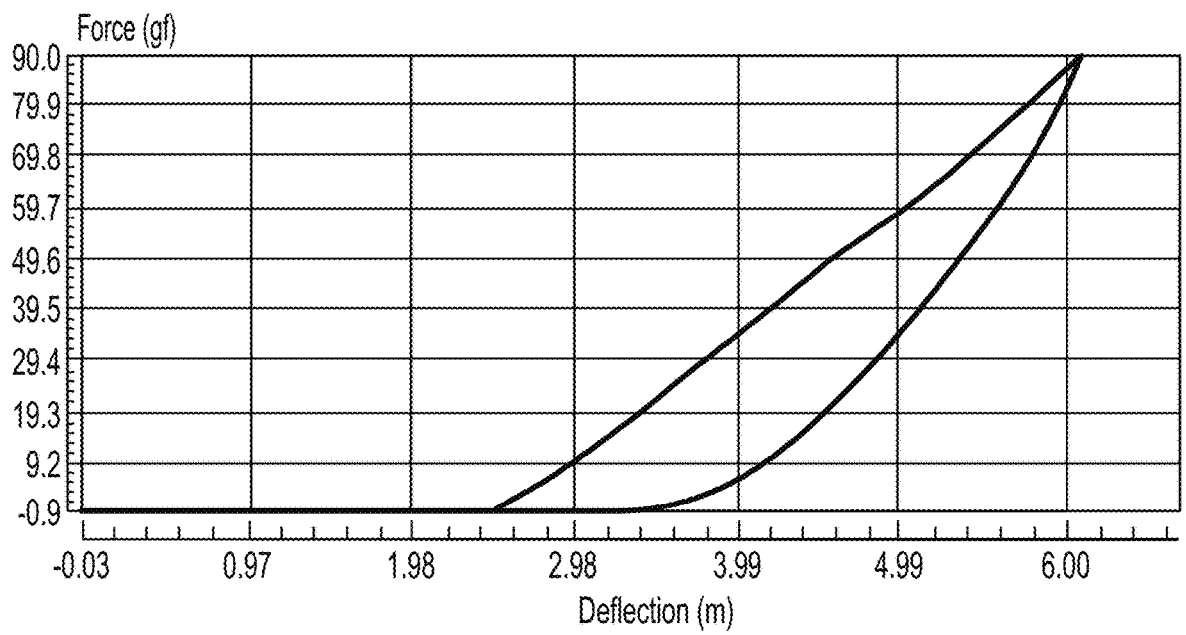
FIG. 39 presents a plot of measured crush resistance with deflection, in accordance with some embodiments of the invention.
Figure 40:
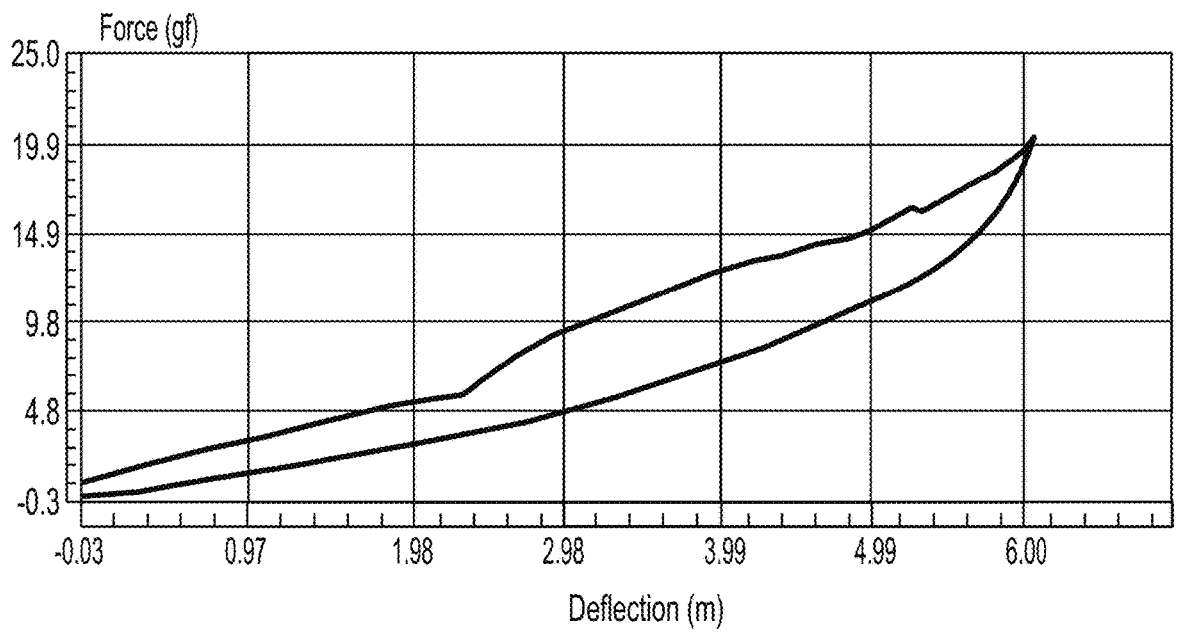
FIG. 40 presents a plot of measured crush resistance with deflection, apparently for a stent of the art.

In some embodiments, the second portion includes axial struts, correspondingly, for example, in some embodiments, the protrusion of the second portion into structure lumen 3899 is hexagon-like in shape as illustrated in FIG. 38C. FIG. 38E is a photographic illustration of a top view of an exemplary structure with a second portion protruding into a structure lumen, according to some embodiments of the invention.

Construction of the Structure

In some embodiments, the SM portion and/or the polymer portion are solid tubes with an internal structure lumen. In some embodiments, the SM portion and/or the polymer portion are formed of struts and/or are lattice-like and/or are mesh-like. In some embodiments, the SM portion and/or the polymer portion are tubular and are formed of struts/lattice/mesh. In some embodiments, a percentage of the tube surface which is delineated by a part of the structure, herein termed surface coverage, is between 10%-95%, or over 95%, or less than 10% or intermediate values, such as 20%, 40%, 60% or intermediate values. In embodiments with non-tubular structures, surface coverage relates to structure surface porosity and is, for example, between 10%-95%, or over 95%, or less than 10% or intermediate values, such as 20%, 40%, 60% or intermediate values. In an exemplary embodiment of the invention, the SM portion and second portion have different coverage percentages, for example, being different by a factor of 1.5, 2, 3, 4 or intermediate or greater factors (e.g., more second portion than SM portion coverage or vice versa).

Figure 41:
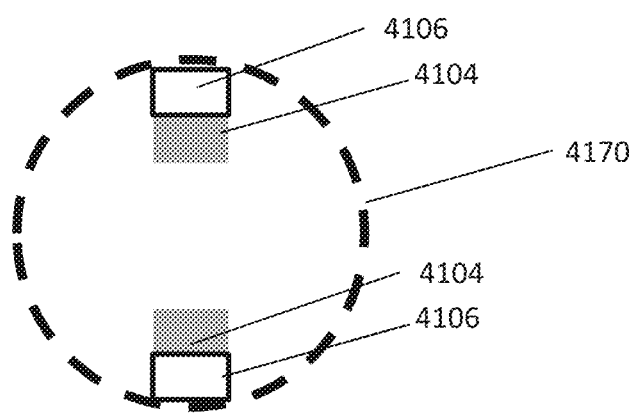
FIG. 41 is a simplified schematic cross sectional view of a structure, according to some embodiments of the invention.
Figure 42:
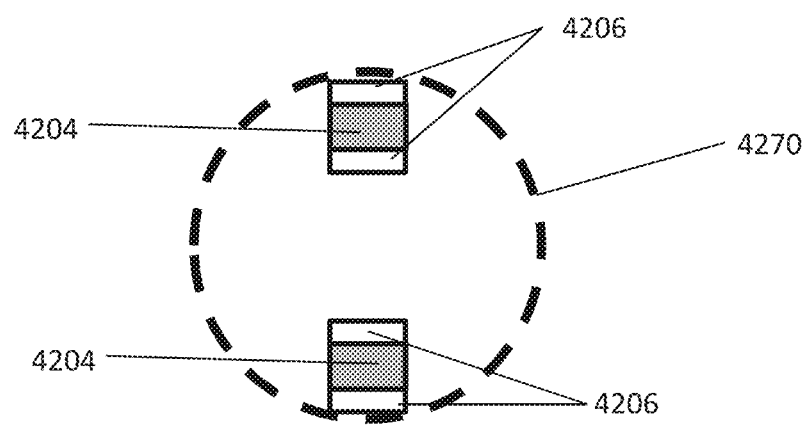
FIG. 42 is a simplified schematic cross sectional view of a structure, showing various layers therein, according to some embodiments of the invention.

FIG. 41 is a simplified schematic cross sectional view of a structure, according to some embodiments of the invention. FIG. 42 is a simplified schematic cross sectional view of a structure, according to some embodiments of the invention. FIG. 41 and FIG. 42. illustrate a feature of some embodiments, that, at any particular cross section, a portion of a tube surface 4170, 4270 is inhabited by a SM portion 4104, 4204 and a second portion 4106, 4206. In other embodiments, some parts of the cross-section have only one of the SM portion and second portion (this can be seen in FIG. 19, for example). Furthermore, in some embodiments, while each (or many) cross-sections include both SM material and other (second) material, they need not be located at the same circumferential position. For example, in FIG. 20, SM material is generally arranged at angles and second portion material is generally arranged parallel to the axis of the stent, so at most locations, two struts (of different layers) will meet at an angle and not overlap for much of their lengths. FIG. 41 shows an example where the second portion surrounds the first portion. FIG. 42 shows an example where each SM portion is sandwiched between two second portion-materials. This may be the result, for example, of embedding the SM portion in the second portion, or the result of use of multiple layers, possibly with different relaxed diameters and/or material properties. In other embodiments, the SM portion (e.g., at least 51% thereof) is surrounded on at least four cardinal sides by the second portion.

In some embodiments, the SM portion and/or the polymer portion are constructed and/or manufactured by cutting out portions of a solid tube. For example, in some embodiments, the structures of FIGS. 19-23 are constructed by cutting (e.g. laser cutting) out portions of the tubes.

Figure 23:
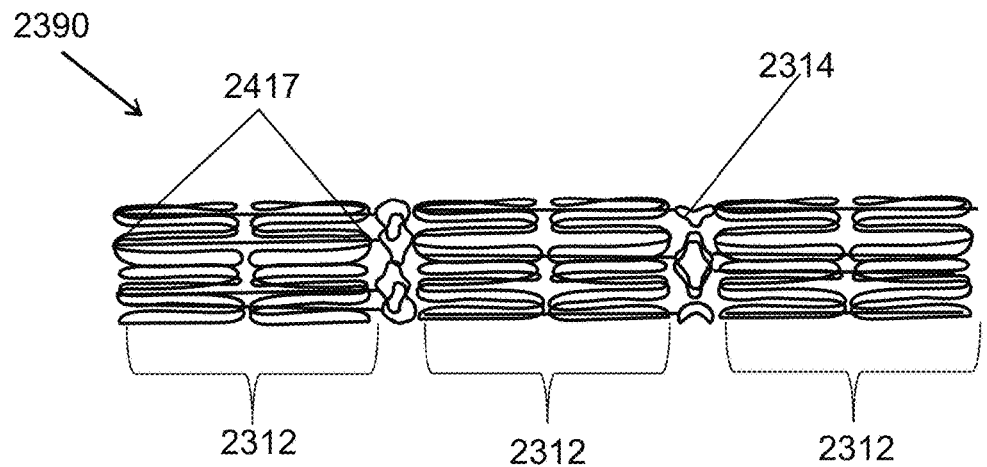
FIG. 23 is a photographic side view of an exemplary structure in a crimped configuration, according to some embodiments of the invention.
Figure 24:
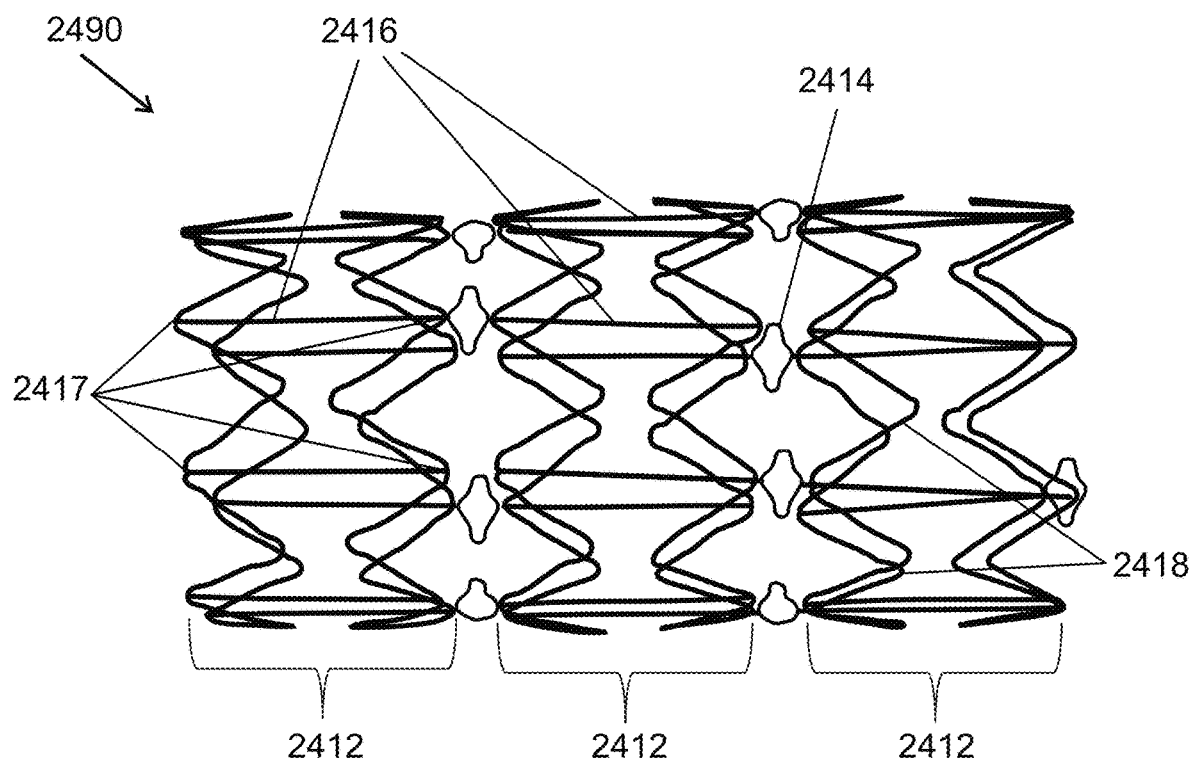
FIG. 24 is a photographic side view the exemplary structure of FIG. 23 in a deployed configuration, according to some embodiments of the invention.

In some embodiments, the structure is constructed by bending one or more wire or tape. FIG. 23 is a photographic side view of a third exemplary structure 2390 in a crimped configuration, according to some embodiments of the invention. FIG. 24 is a photographic side view of a third exemplary structure in a deployed configuration 2490, according to some embodiments of the invention. For example, in some embodiments, the structure illustrated in FIG. 23 and FIG. 24 is optionally constructed by bending and connecting (e.g. by welding) of wires and/or by laser of plasma or other cutting of a tube.

Figure 25:
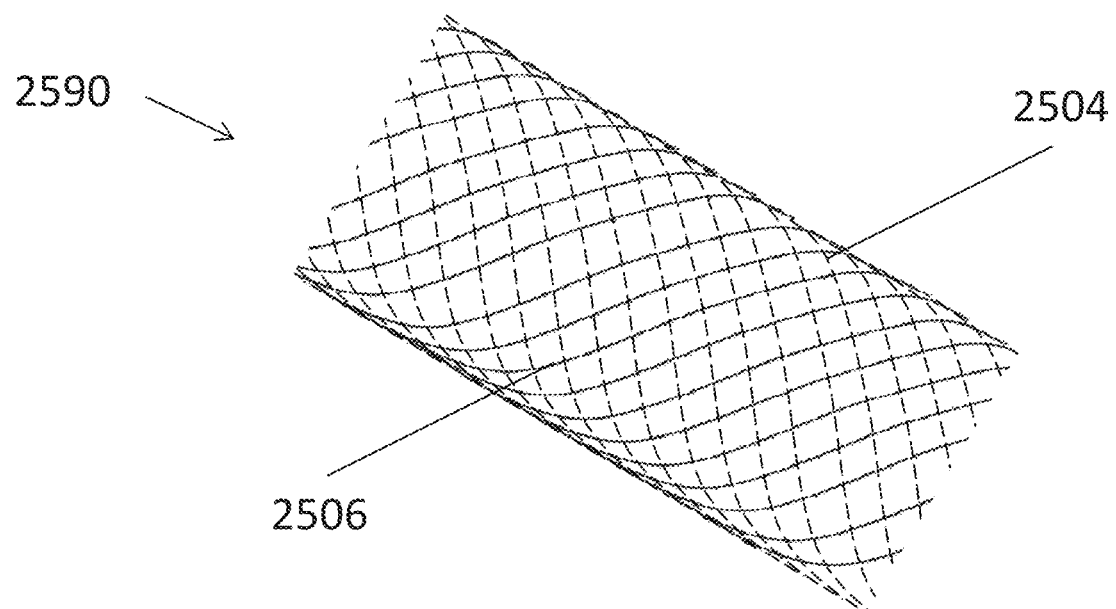
FIG. 25 is a simplified schematic side view of an exemplary braided structure, according to some embodiments of the invention.
Figure 26:
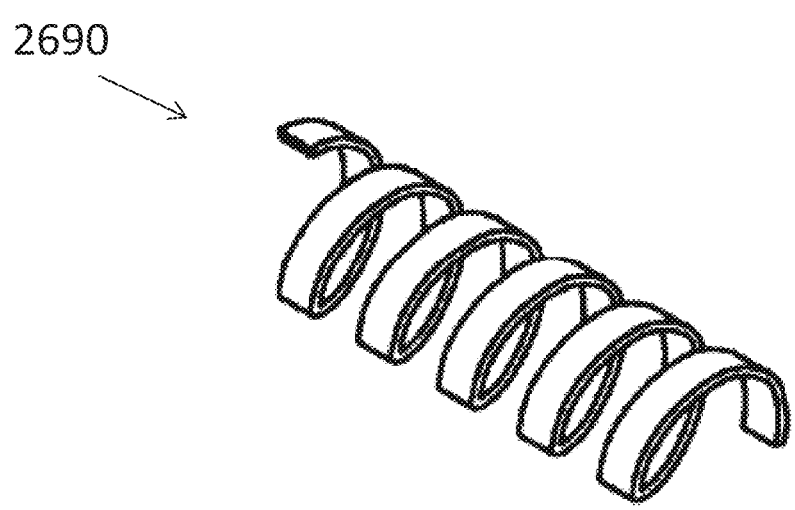
FIG. 26 is a simplified schematic side view of an exemplary coil structure, according to some embodiments of the invention.
Figure 30:
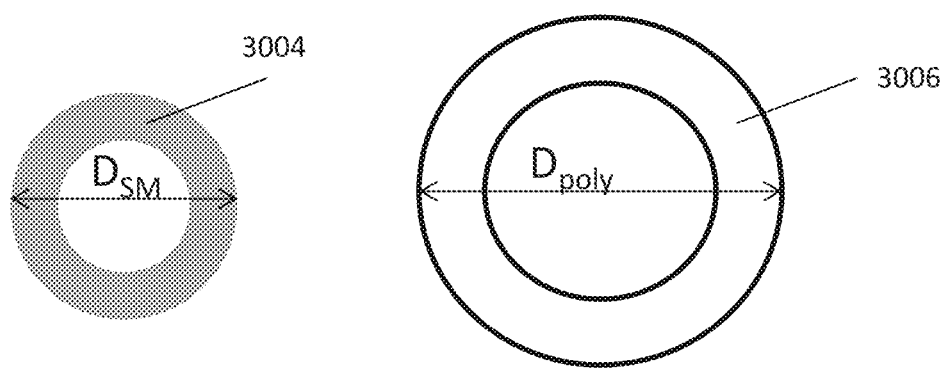
FIG. 30 is a simplified schematic of an uncoupled SM portion and a polymer portion, according to some embodiments of the invention.

In some embodiments, a structure is constructed by braiding or weaving. FIG. 25 is a simplified schematic side view of an exemplary braided structure 2590, according to some embodiments of the invention. SM material portions 2504 are illustrated using solid lines, second portions 2506 (e.g. are illustrated using dashed lines. In some embodiments, a structure (or part thereof) is constructed by winding a tape or wire into a desired shape, e.g. a coil. FIG. 26 is a simplified schematic side view of an exemplary coil structure 2690, according to some embodiments of the invention. Optionally, the coil is formed of a SM material covered by or adhered to or otherwise connected to a polymer or other "second" layer.

Coupling of Portions

In some embodiments, the SM portion is coupled to the polymer portion by tension (e.g., in combination with friction and/or interference using deformation caused by tension). For example, in some embodiments, a SM portion is compressed and/or a polymer portion is expanded and the SM portion is placed within the polymer portion, expanding and contracting forces holding the two portions together.

In some embodiments, the SM portion is coated in polymer (e.g. the SM portion is imbedded in polymer). FIG. 27 is a simplified schematic cross section of a structure with more than two portions, according to some embodiments of the invention. In some embodiments, the structure illustrated in FIG. 27 is constructed by coating a SM portion 2704 (e.g. dip coating), for example, with polymer 2706.

In some embodiments, a structure includes a non-circular cross section, optionally in a crimped and/or a deployed configuration, for example, one or more angles (possibly rounded, possibly with a sharp edge, but with a radius of curvature of less than ¼ of that of the device as a whole) and/or a non-symmetrical cross section. FIG. 28 is a simplified schematic cross section of a structure 2890, according to some embodiments of the invention, showing such sharp bends.

In some embodiments, expansion of the structure is non-radial. For example, the structure illustrated in FIG. 29, in some embodiments, expands substantially more in an x-direction (e.g. by a factor of 1.5, 2, 3, or more, and possible does not expand in a y-direction).

Exemplary Normally Relaxed SM Portion

In some embodiments, the SM portion is relaxed in the crimped configuration and does not exert an expanding force on the polymer portion in the crimped configuration.

In some embodiments, the SM portion is in the austenitic state in the crimped configuration ("normally closed"). Upon, for example, balloon deployment, the SM portion transforms into martensite, due to applied strain, with A'f deployed>Tbody>Af crimped and remains in this state at body temperature, so that SM portion remains in the deployed configuration.

In some embodiments, raising a temperature of the stent causes the SM portion to transform from martensite into austenite phase, and SM portion radial resistance force is less than polymer relaxation force, so the SM portion returns to its crimped austenite shape and the stent collapses, possibly returning to the initial crimped or closed configuration.

In some embodiments, a structure normally closed SM portion is treated to generate a two way shape memory effect (TWSME). In some embodiments, a second shape memory is set for a SM portion diameter larger than the SM portion crimped (e.g. first shape memory) diameter. In some embodiments, the second shape memory leads to additional expansion of SM portion. A potential benefit of a SM portion with a second shape memory is a reduced elastic recoil in the direction of decreasing stent diameter.

Exemplary Low Foreshortening Structure

In some embodiments, the structure has low foreshortening when transferring between a crimped to a deployed configuration: Referring back to FIG. 1A and FIG. 1B, a length, Lcrimp of the structure in a crimped configuration (illustrated in FIG. 1A) is substantially the same as a length Ldply of the structure in a deployed configuration (illustrated in FIG. 1B). In some embodiments, (Lcrimp−Ldply)/

Lcrimp is less than 2%, less than 1%, less than 0.5%. A potential advantage of low foreshortening is the ability to accurately control a position of a deployed stent by positioning of the crimped stent. As noted above, such structures may also be used for stents without strain induced behavior (e.g., not meeting FIG. 6).

Referring back, FIG. 24 shows a structure with low foreshortening in a deployed configuration. In some embodiments, the structure 2490 includes one or more rigid struts orientated axially 2416. In some embodiments, radial expansion of the structure is through unbending and/or stretching of flexible, weaker and/or joint sections 2418. In some embodiments, struts 2416 are not substantially deformed by radial expansion and/or crimping and maintain a substantially constant length. In some embodiments, constant length of rigid struts 2416 substantially maintains the structure length in the crimped and deployed configurations.

In some embodiments, flexible sections 2418 and rigid struts 2416 are connected to each at connection points 2417. In some embodiments, a distance between connection points does not change during crimping and/or expanding/deployment of the structure. In an exemplary embodiment of the invention, it is noted that when deploying a stent axial shortening can occur due to differences in diameter between different segments and/or due to axial bending. In an exemplary embodiment of the invention, flexible interconnections 2414 are provided, for example, in the form of diamonds, but alternatively in the form of curved sections, which can deform to accommodate such differences in radius.

Figure 31:
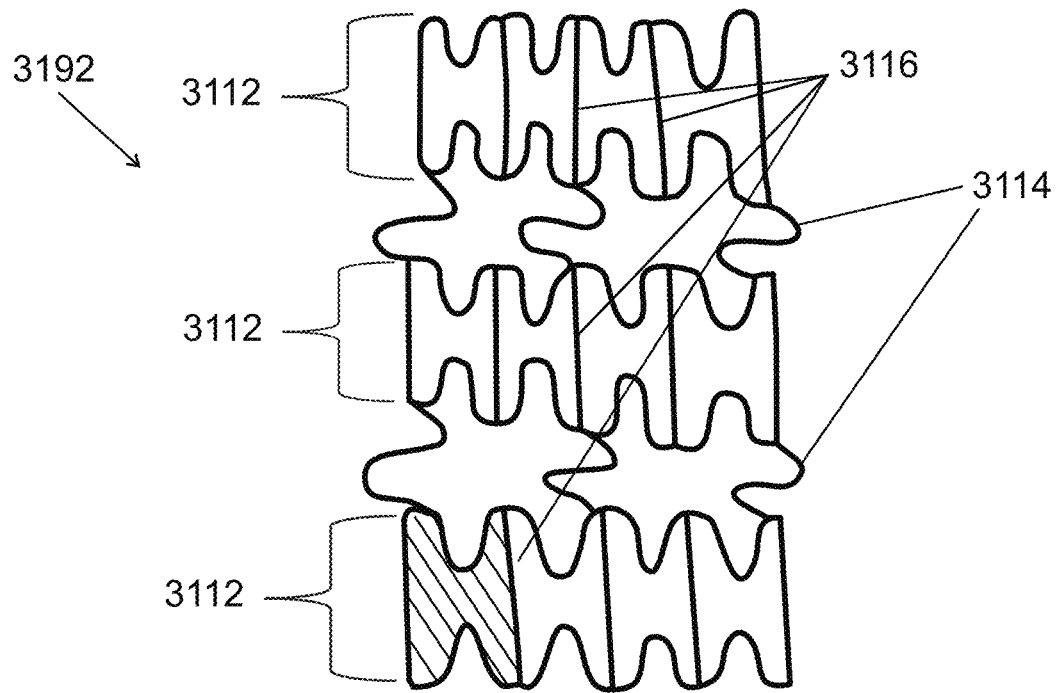
FIG. 31 is a simplified schematic of a section of a structure including low foreshortening, according to some embodiments of the invention.
Figure 32:
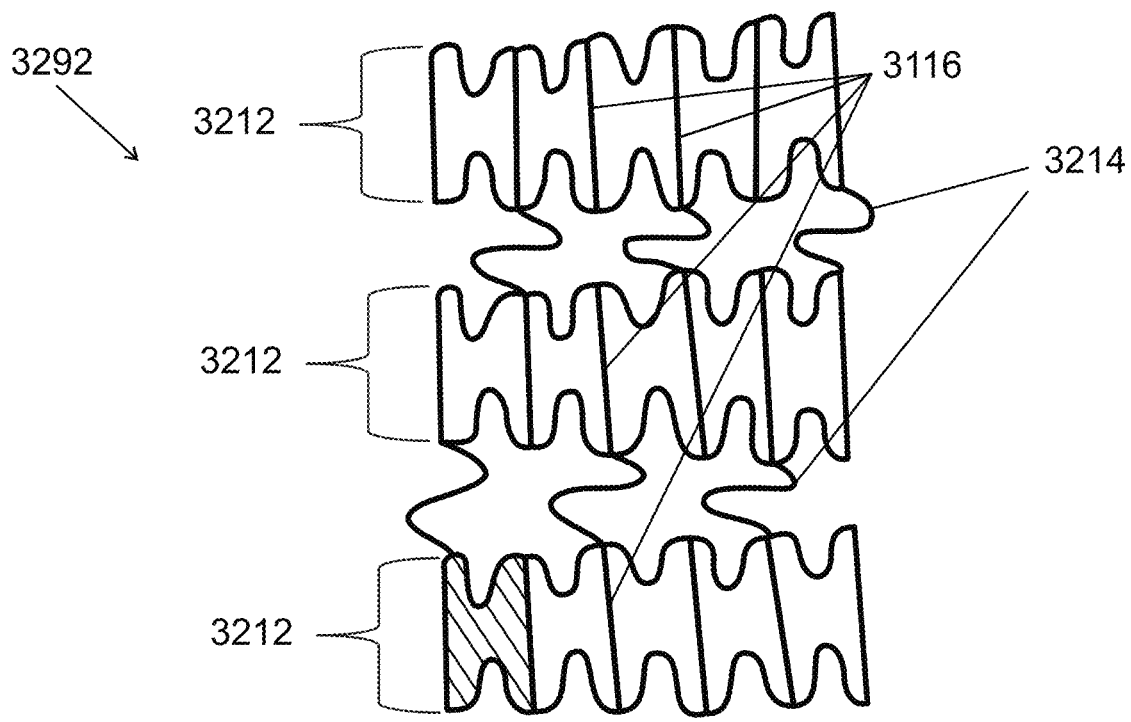
FIG. 32 is a simplified schematic of a section of a structure with low foreshortening, according to some embodiments of the invention.

FIG. 31 is a simplified schematic of a section of a structure 3192 including low foreshortening, according to some embodiments of the invention. FIG. 32 is a simplified schematic of a section 3292 of a structure with low foreshortening, according to some embodiments of the invention. In some embodiments, segments 3112, 3212 include rigid struts orientated axially 3116, 3216. In some embodiments, curved connectors (e.g. sinusoid) 3114 run along the structure axially. In some embodiments curved connectors (e.g. sinusoid) 3214 are staggered axially along the structure. FIG. 32 shows a design with possibly more flexibility than the design of FIG. 31, as the connectors are in adjacent rows rather than same rows as in FIG. 31.

Exemplary Kink Resistance

In some embodiments, the structure bends without significantly (e.g., 20%, 30%, 40% or more) reducing a structure cross sectional area at the bending point and/or the structure bends without closing the structure at a bend and/or substantially decreasing a structure cross sectional area at the bend.

In some embodiments, the structure includes deformable connectors where each connector is able to independently extend and/or retract in length. In an exemplary embodiment of the invention, such connectors extend at one side of the bend (and possibly due to flexibility thereof follow the curve) and contract (rather than bend inwards) at the inside of the bend. As noted above, such structures may also be used for stents without strain induced behavior (e.g., not meeting FIG. 6).

Figure 33:
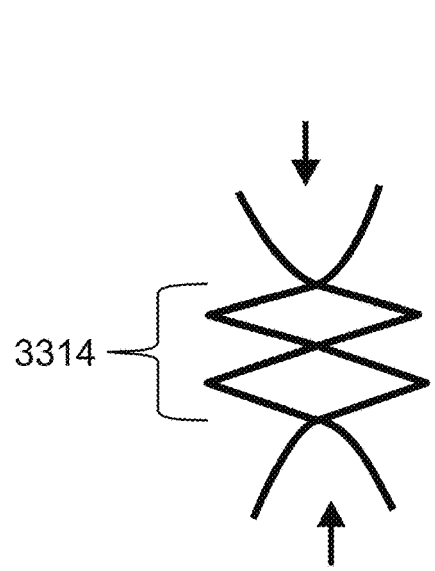
FIG. 33 is a simplified schematic of a contracted connector, according to some embodiments of the invention.
Figure 34:
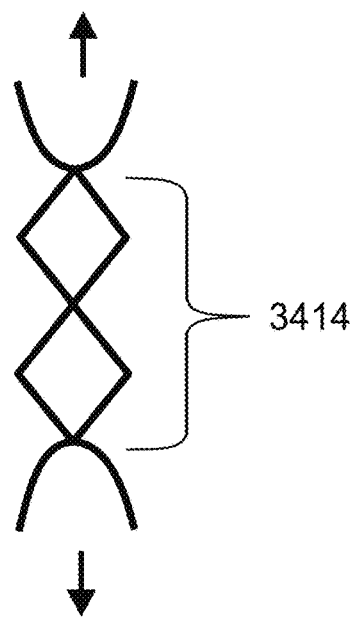
FIG. 34 is a simplified schematic of an extended connector, according to some embodiments of the invention.

FIG. 33 is a simplified schematic of a contracted connector 3314, according to some embodiments of the invention. FIG. 34 is a simplified schematic of an extended connector 3414, according to some embodiments of the invention. In the example shows, the structure is two vertex-to-vertex connected diamonds or parallelogram elements. However, smaller or greater number of elements could be provided. Optionally or alternatively, the elements may be rounded (e.g., ovoid).

Figure 35:
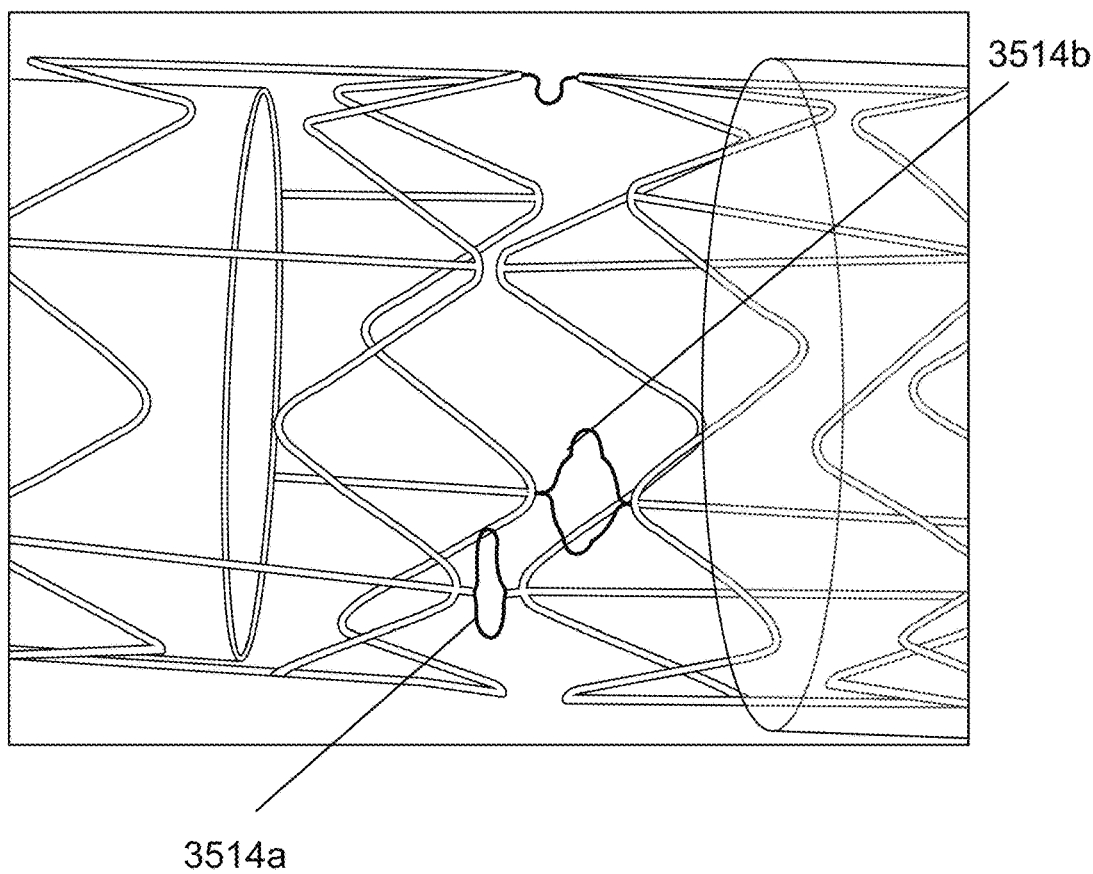
FIG. 35 is a photographic side view of an exemplary structure which has been bent, according to some embodiments of the invention.

FIG. 35 is a photographic side view of a third exemplary structure which has been bent, according to some embodiments of the invention. For example, in some embodiments, when the structure is bent one, or more connector 3514b will extend in length (e.g. those connectors on the outside of the bend) and/or one or more connector with contract in length 3514a (e.g. those connectors on the inside of the bend).

Figure 36:
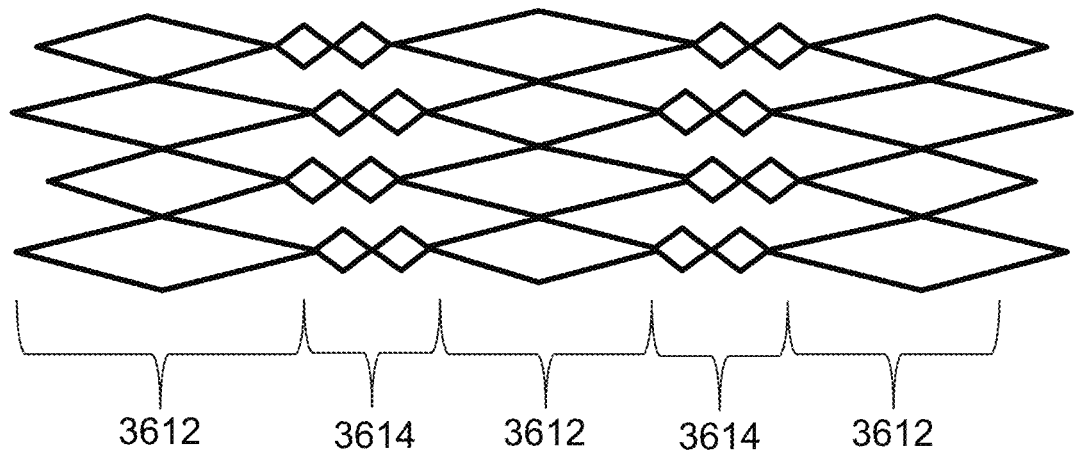
FIG. 36 is a simplified schematic of a section of a structure including kink resistance, according to some embodiment of the invention.

In some embodiments, connectors include rhombic shapes. FIG. 36 is a simplified schematic of a section of a structure including kink resistance, according to some embodiment of the invention. In some embodiments, segments 3612 are rhombic in shape. Connectors 3614 include two rhombic shapes.

Figure 37:
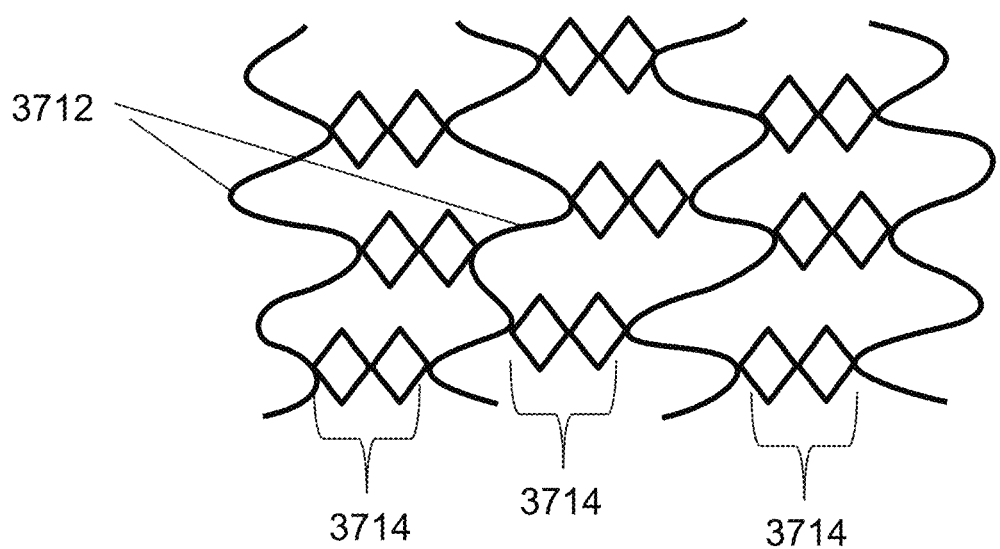
FIG. 37 is a simplified schematic of a section of a structure including kink resistance, according to some embodiments of the invention.

FIG. 37 is a simplified schematic of a section of a structure including kink resistance, according to some embodiments of the invention. Connectors 3114, including two rhombic shapes, connect segments 3712. In some embodiments, structures with rhombic connectors have closed cell structure. FIGS. 36 and 37 illustrates rhombic connectors for closed cell stent structures, wherein FIG. 26 an example of the connectors being adjacent (and not part of) radially resisting sub-structures is shown and in FIG. 37 the connectors may be part of a radially resisting sub-structure.

In an exemplary embodiment of the invention, the connectors are small relative to the segments, for example, in the crimped state, having a length of less than 50%, 30%, 10% or intermediate percentages of a neighboring segment. As noted above, segments need not be perfect cylindrical segments and may have other shapes as well, including ribbon shape and angled cylinder shaped (cylinder, where end faces are not perpendicular to cylinder angle).

In some embodiments, connectors prevent forces being transferred between segments. In some embodiments, an axial force (e.g. force tending to cause structure migration within the lumen) is at least partially absorbed by compression of connectors, for example, preventing and/or reducing stent migration.

In an exemplary embodiment of the invention, the connectors are weaker than the segments, for example, by a factor of at least 2, 3, 4 or more. However, as all or most deployment forces are radial, the connectors do not need to resist (during or after deployment) large forces.

A potential benefit of contractible and/or extendible connectors, which is also a potential advantage of polymer only connector/s, is a flexible connection between segments, for example, providing high stent flexibility (e.g. for deployment) and/or high conformability (e.g. to a lumen). A potential advantage of a stent with high conformability is a low movement of the deployed stent within the lumen (e.g., migration resistance).

Exemplary Non-Tubular Structures

In some embodiments, the structure is tubular in a crimped configuration and is expanded to a sphere-like (or other substantially closed) shape in a deployed configuration. In some embodiments, a SM portion shape memory is set to be a sphere-like shape. In some embodiments, a SM portion shape memory is set to be a body lumen shape or a part of body lumen shape, e.g. bladder, portion of the heart. In some embodiments, the structure has in crimped configuration small diameter cylindrical shape and, in a deployed configuration has a sphere-like shape, with elliptical distortion. In some embodiments, the deployed configuration is provided due to deployment of high compliance balloon and complies with a body duct. In some embodiments, a SM portion has normally closed shape in austenite state and the SM portion transforms into strain induced martensite upon balloon deployment. In some embodiments, the structure is removed by self-crimping. In some embodiments, self crimping is when the structure is heated to above Af'>body temperature>Af.

In some embodiments a self-expanding upon heating embodiment is used, so there is no need to provide a balloon inside the structure being deployed, however, slow deployment can be provided (e.g., using spurs of heated fluid with fluoroscopy for feedback).

Additional structures may be provided in accordance with some embodiments of the invention. For example, a beam, having a layer of SM material and a second layer of "second portion" material, may be deployed (e.g., by bending) as described herein, and once deployed, will resist crushing and crimping and can possibly self undeploy. This may be useful for hooks as well, whereby cooling may be used to straighten the hooks, while the two layer design being used to provide sufficient strength prior thereto. Optionally or alternatively, to a hook, a curved beam may be provided.

In such embodiments, such a beam can optionally be balanced at multiple deformation (e.g., "expansion") positions.

Another example of a structure is a ring or other curved or arcuate shape, optionally nearly or completely closed, which can be formed of two rings, each one of a different material.

Another example of a structure is a joint (e.g., a living hinge or a location of weaker material where stiffer struts meet). Such a joint can be locked into multiple positions and resist small amounts of deformation, with significant resilience.

As can be appreciated, such components (cylinder, sphere, beams, joints, etc.) and/or other components can be combined to provide arbitrary composite structures.

For brevity of description, most of the specification refers specifically to tubular shapes, however, the mechanisms, structure and treatments described herein should be understood to refer to other structures as well, such as beams.

Exemplary Additional Technologies

The designs described herein are generally compatible with many stent technologies.

In some embodiments, a structure includes one or more radiopaque marker, for example to assist in structure placement in a body lumen. Such a marker may be, for example, welded to the SM section and/or embedded in a polymer section.

In some embodiments, drug eluting is provided. In some embodiments, the polymer portion includes one or more drug eluting part. In some embodiments, the SM portion includes one or more drug eluting part. Optionally or alternatively, drug storage is in a layer or reservoirs between the two portions, or is provided in a third portion and/or as a coating layer.

In an exemplary embodiment of the invention, additional physiologically function layers, such as mesh for encouraging endothelial growth or a graft layer, are provided.

General

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

As used herein the term "about" refers to ±20%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1—Animal Experiment—Post Operative Stenting

Figure 70:
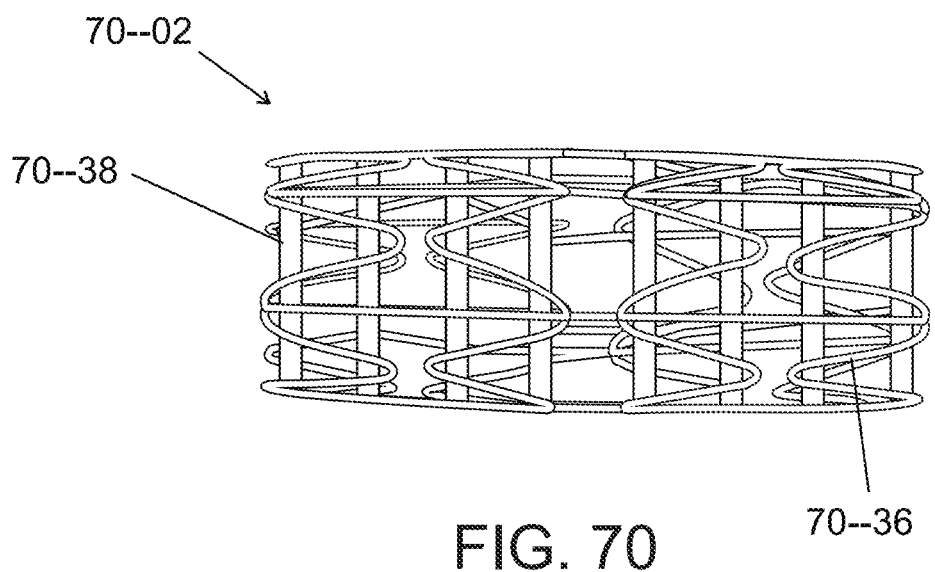
FIG. 70 is a side view of a stent removed after 28 days within a sheep ethmoid ostium, according to some embodiments of the invention.

FIG. 70 is a side view of a stent 7002 removed after 28 days within a sheep ethmoid ostium, according to some embodiments of the invention. Stent 7002 is approximately 20 mm long and with a crimped diameter of approximately 4 mm. Stent 7002 includes an inner portion including a nitinol portion 7036 held by a polymer portion 7038 made of Tecoflex™ EG-80A aliphatic polyether-based thermoplastic polyurethane polymer.

A sheep ethmoid ostium was wounded, in order to simulate FESS, by manual abrasion to create a superficial wound of about 2-3 mm long.

The stent illustrated in FIG. 70 was inserted through the nostril, positioned at the wound site and balloon expanded to a diameter which was measured using x-ray images to be approximately 8.3 mm. The stent was left in position for 28 days and then successfully removed by self-crimping onto a retrieval device by irrigating with cold saline solution.

FIGS. 71A-D show experimental results.

Figure 71A:
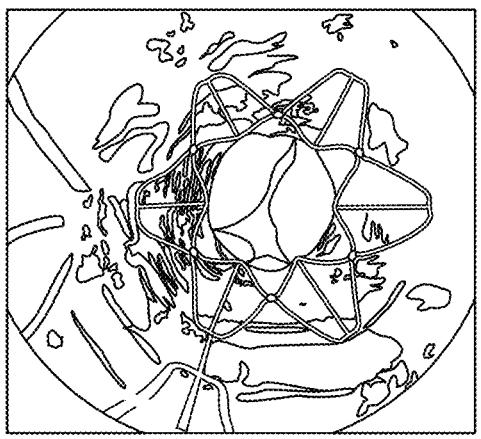
FIG. 71A is an endoscope image of the stent on the day of insertion, showing good conformability of the stent to ostium geometry, in accordance with some embodiments of the invention.

FIG. 71A is an endoscope image of the stent on the day of insertion, showing good conformability of the stent to ostium geometry.

Figure 71B:
FIG. 71B is an endoscope image of the stent on day 28, in accordance with some embodiments of the invention.

FIG. 71B is an endoscope image of the stent on day 28. The image was acquired prior to stent removal and shows that the stent has not become embedded in surrounding tissue (struts are visible through the stent, although the stent was covered by nasal discharge).

Figure 71C:
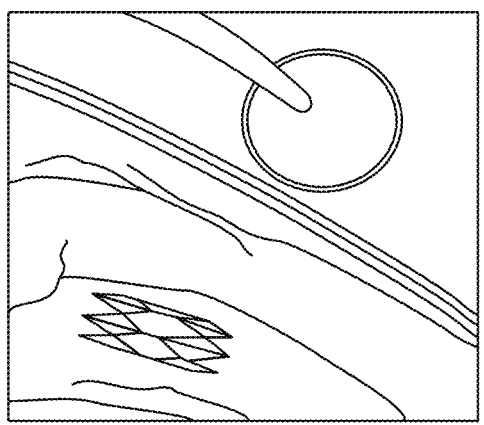
FIG. 71C is an x-ray image of the stent on day 28, in accordance with some embodiments of the invention.

FIG. 71C is an x-ray image of the stent on day 28.

Figure 71D:
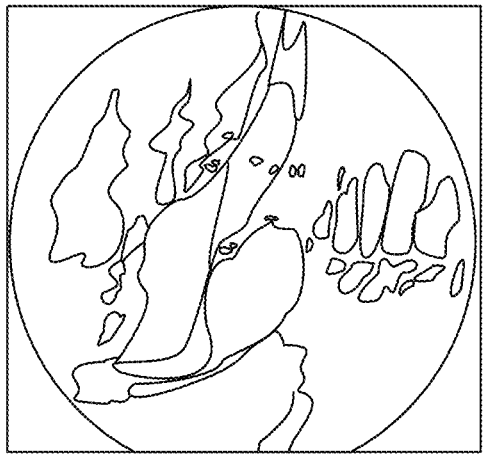
FIG. 71D is an endoscope image of the treated area on day 28 after stent removal, in accordance with some embodiments of the invention.

FIG. 71D is an endoscope image of the treated area on day 28 after stent removal. The image shows that the wound has healed and there is no inflammation in nasal tissue. Lack of inflammation and surface irritation indicates that the stent has not significantly migrated during treatment.

As illustrated in FIG. 70, the stent maintained structure integrity after 28 days of implantation.

What is claimed is:

1. A method of treatment of nasal conditions comprising:
delivering an expandable structure in a crimped configuration to a nasal lumen, wherein said expandable structure comprises:
a shape memory (SM) portion; and
a polymer portion where said polymer portion elastically resists expansion of said SM portion to define a plurality of different stable expanded configurations of said expandable structure;
expanding said expandable structure within said nasal lumen to a stable expanded configuration of said plurality of different stable expanded configurations;
allowing a radial deformation of said expandable structure, and elastically returning from said radial deformation to said stable expanded configuration, said expandable structure radially deforming elastically under forces of said nasal lumen on said expandable structure, a SM portion expanding force being higher than a polymer resistance force required to expand said polymer portion from said radial deformation; and
removing said expandable structure from said nasal lumen, after a time period, where removing comprises causing said expandable structure to self-crimp by reducing a SM resistance force to below a polymer elastic relaxation force.

2. The method according to claim 1, wherein said causing comprises changing a temperature of said expandable structure.

3. The method according to claim 2, wherein said changing a temperature comprises lowering a temperature.

4. The method according to claim 1, wherein said expandable structure substantially does not apply outwards pressure to said nasal lumen.

5. The method according to claim 1, wherein said nasal lumen is one of a sinus ostium, a portion of a nasal cavity between a turbinate and a septum, a surgically created lumen, and an ethmoid sinus cavity surgically created during ethmoidectomy.

6. The method according to claim 1, wherein said expanding is by application of an expanding force to said expandable structure and said expanding force is at most half of a force required to crush said expandable structure in said stable expanded configuration.

7. The method according to claim 1, wherein at least one of:
said delivering and said expanding, and said removing is carried out without general anesthetic.

8. The method according to claim 1, wherein said expandable structure releases medication into said nasal lumen.

9. The method according to claim 1;
wherein said expandable structure is stable for a range of diameters and for a range of diameters along an expandable structure length including:
a range of crimped diameters suitable for inserting the expandable structure into the nasal lumen; and
a range of deployed diameters suitable for supporting at least a portion of the nasal lumen;
wherein said expandable structure substantially does not apply outward pressure to the nasal lumen, and wherein said expandable structure has a preselected crush resistance for retaining a nasal lumen in an open configuration.

10. The method according to claim 9, wherein said expandable structure in said range of deployed diameters has a resistance to a crimping force acting to radially crimp the expandable structure equal to at least 100% of a force required to expand the expandable structure from said range of crimped diameters to said range of deployed diameters.

11. The method according to claim 9, wherein, for said range of deployed diameters, said expandable structure collapses, upon a reduction in temperature, to a diameter within said range of crimped diameters.

12. The method according to claim 9, wherein said expandable structure is configured for insertion into a nasal cavity through a nostril;
wherein at least part of an elastic element is located within said expandable structure;
wherein at least part of a balloon is within said elastic element and within said expandable structure; and wherein an input pipe is connected to said balloon wherein said balloon is inflated through said pipe;

wherein said elastic element resists expansion of said balloon;

wherein there is provided a second input pipe including an outlet, where fluid exiting said outlet irrigates a region adjacent to said balloon.

13. The method according to claim 9, wherein said polymer portion has a non-uniform cross section including:
a peripheral layer composed at least 30% of a second polymer, and
a frame composed at least 30% of a first polymer; said second polymer having a greater environmental durability than said first polymer and wherein said first polymer has a higher creep resistance than said second polymer.

14. The method according to claim 9, wherein said polymer portion has a non-uniform cross section including:
a peripheral layer, and
a frame;
wherein said frame comprises a first polymer and an average concentration of said first polymer in said frame is at least twice an average concentration of said first polymer in said peripheral layer;
wherein said peripheral layer comprises a second polymer and an average concentration of said second polymer in said peripheral layer is at least twice an average concentration of said second polymer in said frame;
wherein said second polymer has a greater environmental durability than said first polymer; and
wherein said first polymer has a higher creep resistance than said second polymer.

15. The method according to claim 9, wherein said polymer portion is configured to resist expansion of said SM portion, over a plurality of different expansion states of said SM portion; said polymer portion having a non-uniform cross section including:
a peripheral layer, and
a frame;
wherein said frame comprises a first polymer and an average concentration of said first polymer in said frame is at least twice an average concentration of said first polymer in said peripheral layer;
wherein said peripheral layer comprises a second polymer and an average concentration of said second polymer in said peripheral layer is at least twice an average concentration of said second polymer in said frame;
wherein said second polymer has a greater environmental durability than said first polymer;
wherein said first polymer has a higher creep resistance than said second polymer;
wherein said polymer portion is configured to apply a contracting force when said polymer portion is mechanically coupled to said SM portion; and
wherein said SM portion is pre-treated to have a decrease in SM portion expansion force as a function of a strain applied to said SM portion and to display a strain induced martensite behavior.

16. The method according to claim 15, wherein said polymer portion is formed by multi-layer coextrusion of at least a first layer including said peripheral layer and a second layer including said frame.

17. The method according to claim 15, wherein said second polymer has melt flow index (MFI) less than ⅔ of an MFI of said first polymer.

18. The method according to claim 15, wherein at least one of said peripheral layer and said frame maintains elasticity with a maximum residual strain of 30% after a 300% full strain.

19. The method according to claim 18, wherein at least one of said peripheral layer and said frame is configured for retaining said residual strain over at least 5 expand-collapse cycles to said full strain.

20. The method according to claim 15, further comprising a second peripheral layer and wherein said frame is disposed between said peripheral layer and said second peripheral layer.

21. The method according to claim 15, wherein said peripheral layer is composed at least 50% of a polymer having a greater environmental durability than said second polymer.

22. The method according to claim 15, wherein said expandable structure is stable, over a plurality of different expansion states.

23. The method according to claim 1, wherein said polymer portion is elastic upon expansion of less than a minimum expansion time period; and
wherein, for an expansion to an expanded configuration for a time period of more than said minimum expansion time period, said expandable structure remains in said stable expanded configuration.

24. The method according to claim 1, wherein said expandable structure is stable for a range of diameters and for varying diameters along an expandable structure length.

25. The method according to claim 1, wherein said expanding includes expanding via a deployment device, said expandable structure including at least one drug eluting part.

26. The method according to claim 25, wherein said deployment device comprises a balloon.

27. The method according to claim 25, wherein said SM portion includes said at least one drug eluting part.

28. The method according to claim 25, wherein said polymer portion includes said at least one drug eluting part.

29. The method according to claim 25, wherein said expandable structure includes:
at least one of a layer and at least one reservoir between said SM portion and said polymer portion, containing said drug eluting part.

30. The method according to claim 25, wherein said expandable structure includes:
at least one of a third portion and a coating layer containing said drug eluting part.

31. The method according to claim 25, wherein said at least one drug eluting part is provided between said SM portion and said polymer portion.

32. The method according to claim 25,
wherein said at least one drug eluting part includes at least one drug eluting coating.

33. The method according to claim 25, wherein said at least one drug eluting part includes at least one drug eluting layer.

34. The method according to claim 1, wherein said includes at least one of:
at least one reservoir between said SM portion and said polymer portion; and
a drug eluting layer.

35. The method according to claim 1, wherein, in said stable expanded configuration, a SM portion expanding force is less than a force required to expand said polymer portion.

36. The method according to claim 35, wherein, in said stable expanded configuration, said SM portion resistance force is larger than said polymer elastic relaxation force.

37. The method according to claim 1, wherein said radial deformation of the expandable structure loads the SM portion and said SM portion expanding force acting to expand said SM portion, is in reaction to the loading.

* * * * *